US008163488B2

(12) United States Patent
Lofton-Day et al.

(10) Patent No.: US 8,163,488 B2

(45) Date of Patent: Apr. 24, 2012

(54) METHODS AND NUCLEIC ACIDS FOR ANALYSIS OF COLON PROLIFERATIVE DISORDERS

(75) Inventors: Catherine Lofton-Day, Seattle, WA (US); Matthias Ebert, Muenchen (DE)

(73) Assignee: Epigenomics AG, Berlin (DE)

( * ) Notice: Subject to any disclaimer, the term of this patent is extended or adjusted under 35 U.S.C. 154(b) by 780 days.

(21) Appl. No.: 10/562,089

(22) PCT Filed: Jun. 23, 2004

(86) PCT No.: PCT/US2004/020279

§ 371 (c)(1), (2), (4) Date: Jan. 28, 2008

(87) PCT Pub. No.: WO2005/001140

PCT Pub. Date: Jan. 6, 2005

(65) Prior Publication Data

US 2009/0047666 A1 Feb. 19, 2009

Related U.S. Application Data

(63) Continuation-in-part of application No. 10/603,138, filed on Jun. 23, 2003, now abandoned.

(51) Int. Cl.
*C12Q 1/68* (2006.01)
*C12P 19/34* (2006.01)

(52) U.S. Cl. ..................... 435/6.11; 435/6.14; 435/91.1; 436/64

(58) Field of Classification Search ........................ None
See application file for complete search history.

(56) References Cited

U.S. PATENT DOCUMENTS

| | | | |
|---|---|---|---|
| 5,565,552 | A | 10/1996 | Magda et al. |
| 5,567,810 | A | 10/1996 | Weis et al. |
| 5,574,142 | A | 11/1996 | Meyer, Jr. et al. |
| 5,585,481 | A | 12/1996 | Arnold, Jr. et al. |
| 5,587,371 | A | 12/1996 | Sessler et al. |
| 5,597,696 | A | 1/1997 | Linn et al. |
| 5,786,146 | A | 7/1998 | Herman et al. |
| 5,958,773 | A | 9/1999 | Monia et al. |
| 6,251,594 | B1 | 6/2001 | Gonzalgo et al. |
| 6,265,171 | B1 | 7/2001 | Herman et al. |
| 6,331,393 | B1 | 12/2001 | Laird et al. |

FOREIGN PATENT DOCUMENTS

| | | |
|---|---|---|
| WO | WO 95/00669 | 1/1995 |
| WO | WO 95/15373 | 6/1995 |
| WO | WO 97/46705 | 12/1997 |
| WO | WO 99/28498 | 6/1999 |
| WO | WO 00/26401 | 5/2000 |
| WO | WO 01/75172 | 10/2001 |

OTHER PUBLICATIONS

Ester et al. (Cancer Research, 2001, vol. 61, pp. 3225-3229).*
Cottrell, Clinical Biochem, 2004, vol. 37, p. 595-604.*
Ehrlich, Oncogene, 2002 vol. 21, pp. 5400-5413.*
U.S. Appl. No. 10/603,138, Jun. 23, 2003, Lofton-Day et al.
Bachman et al., "Methylation-associated Silencing of the Tissue Inhibitor of Metalloproteinase-3 Gene Suggests a Suppressor Role in Kidney, Brain, and Other Human Cancers," Cancer Research, Feb. 15, 1999, vol. 59.
Database, "H. sapiens CpG island DNA genomic Msel fragment, clone 97b5, forward read cpg97b5.ftla," XP002312906, retrieved from EBI accession No. EM HUM:HS97B5F, Oct. 23, 1995 (1 page).
Eads et al., "CpG Island Hypermethylation in Human Colorectal Tumors Is Not Associated with DNA Methyltransferase Overexpression," Cancer Research, May 15, 1999, pp. 2302-2306, vol. 59.
Eads et al., "Epigenetic Patterns in the Progression of Esophageal Adenocarcinoma," Cancer Research, Apr. 15, 2001, pp. 3410-3418, vol. 61.
Eads et al., "Fields of Aberrant CpG Island Hypermethylation in Barrett's Esophagus and Associated Adenocarcinoma," Cancer Research, Sep. 15, 2000, pp. 5021-5026, vol. 60.
Feil et al., "Methylation analysis on individual chromosomes: improved protocol for bisulphite genomic sequencing," Nucleic Acids Research, 1994, pp. 695-696, vol. 22, No. 4.
Frommer et al., "A genomic sequencing protocol that yields a positive display of 5-methylcytosine residues in individual DNA strands," The Proceedings of the National Academy of Sciences, Mar. 1992, pp. 1827-1831, vol. 89.
Gonzalgo et al., "Identification and Characterization of Differentially Methylated Regions of Genomic DNA by Methylation-sensitive Arbitrarily Primed PCR," Cancer Research, Feb. 15, 1997, pp. 594-599, vol. 57.
Gonzalgo et al., Rapid quantitation of methylation differences at specific sites using methylation-sensitive single nucleotide primer extension (Ms-SNuPE), Nucleic Acids Research, 1997, pp. 2529-2531, vol. 25, No. 12.
Grigg et al., "Sequencing 5-Methylcytosine Residues in Genomic DNA," BioEssays, Jun. 1994, pp. 431-436, vol. 16, No. 6.
Gut et al, "DNA and Matrix Assisted Laser Desorption Ionization Mass Spectrometry," Molecular Biology: Current Innovations and Future Trends, 1995, pp. 147-157, Horizon Scientific Press, Wymondham, United Kingdom.
Gut et al., "A procedure for selection DNA alkylation and detection by mass spectrometry," Nucleic Acids Research, 1995, pp. 1367-1373, vol. 23, No. 8.
Heid et al., "Real Time Quantitative PCR," Genome Research, 1996, pp. 986-994, vol. 6.
Herman et al., "Inactivation of the CDKN2/p16/MTS1 Gene Is Frequently Associated with Aberrant DNA Methylation in All Common Human Cancer," Cancer Research, Oct. 15, 1995, pp. 4525-4530, vol. 55.
Herman et al., "Methylation-specific PCR: a novel PCR assay for methylation status of CpG islands," The Proceedings of the National Academy of Sciences, Sep. 1996, pp. 9821-9826, vol. 93.

(Continued)

*Primary Examiner* — Sarae Bausch

(74) *Attorney, Agent, or Firm* — DLA Piper LLP (US)

(57) ABSTRACT

The invention provides methods, nucleic acids and kits for detecting colon cell proliferative disorders. The invention discloses genomic sequences the methylation patterns of which have utility for the improved detection of and differentiation between said class of disorders, thereby enabling the improved diagnosis and treatment of patients.

16 Claims, 5 Drawing Sheets

OTHER PUBLICATIONS

Hiltunen et al., "Hypermethylation of the APC (Adenomatous Polyposis Coli) Gene Promoter Region in Human Colorectal Carcinoma," The International Journal of Cancer, 1997, pp. 644-648, vol. 70.
Karas et al., "Laser Desorption Ionization of Proteins with Molecular Masses Exceeding 10 000 Daltons," Analytical Chemistry, Oct. 15, 1988, pp. 2299-2301, vol. 60, No. 20.
Martin et al., "Genomic sequencing indicates a correlation between DNA hypomethylation in the 5' region of the pS2 gene and its expression in human breast cancer cell lines," Gene, 1995, pp. 261-265, vol. 157.
Olek et al., "A modified and improved method for bisulphite based cytosine methylation analysis," Nucleic Acids Research, 1996, pp. 5064-5066, vol. 24, No. 24.
Olek et al., "The pre-implantation ontogeny of the H19 methylation imprint," Nature Genetics, Nov. 1997, pp. 275-276, vol. 17.
Rein et al., "Identifying 5-methylcytosine and related modifications in DNA genomes," Nucleic Acids Research, 1998, pp. 2255-2264, vol. 26, No. 10.
Sadri et al., "Rapid analysis of DNA methylation using new restriction enzyme sites created by bisulfite modification," Nucleic Acids Research, 1996, pp. 5058-5059, vol. 24, No. 24.
Sanger et al., "DNA Sequencing with chain-terminating inhibitors," The Proceedings of the National Academy of Sciences, Dec. 1977, pp. 5463-5468, vol. 74, No. 12.
Toyota et al., "CpG island methylator phenotype in colorectal cancer," The Proceedings of the National Academy of Sciences, Jul. 1999, pp. 8681-8686, vol. 96.
Toyota et al., "Identification of Differentially Methylated Sequences in Colorectal Cancer by Methylated CpG Island Amplification," Cancer Research, May 15, 1999, pp. 2307-2312, vol. 59.
Van Der Krol et al., "Modulation of Eukaryotic Gene Expression by Complementary RNA or DNA Sequences," BioTechniques, 1988, pp. 958-976, vol. 6, No. 10.
Van Rijnsoever et al., "Characterisation of colorectal cancers showing hypermethylation at multiple CpG islands," Gut, 2002, pp. 797-802, vol. 51.
Xiong et al., "Cobra: a sensitive and quantitative DNA methylation assay," Nucleic Acids Research, 1997, pp. 2532-2534, vol. 25, No. 12.
Yan et al., "CpG Island Arrays: an Application toward Deciphering Epigenetic Signatures of Breast Cancer," Clinical Cancer Research, Apr. 2000, pp. 1432-1438, vol. 6.
Young et al., "HPP1: A transmembrane protein-encoding gene commonly methylated in colorectal polyps and cancers," The Proceedings of the National Academy of Sciences, Jan. 2, 2001, pp. 265-270, vol. 98, No. 1.
Yu et al., "Specific Inhibition of PCR by Non-Extendable Oligonucleotides Using a 5' to 3' Exonuclease-Deficient DNA Polymerase," BioTechniques, 1997, pp. 714-720, vol. 23, No. 4.
Zeschnigk et al., "Imprinted segments in the human genome: different DNA methylation pattersn in the Prader-Willi/ Angelman syndrome region as determined by the genomic sequencing method," Human Molecular Genetics, 1997, pp. 387-395, vol. 6, No. 3.
Zeschnigk et al., "A single-tube PCR test for the diagnosis of Angelman and Prader-Willi syndrome based on allelic methylation differences at the SNRPN locus," European Journal of Human Genetics, Mar.-Apr. 1997, pp. 94-98, vol. 5, No. 2.
Zon, "Oligonucleotide Analogues as Potential Chemotherapeutic Agents," Pharmaceutical Research, 1988, pp. 539-549, Vol. 5, No. 9.

* cited by examiner

A

B 60
50
40
30
20
10
0 primary tumor metastasis

SEQUENCE LISTING

```
<160> NUMBER OF SEQ ID NOS: 76

<210> SEQ ID NO 1
<211> LENGTH: 2470
<212> TYPE: DNA
<213> ORGANISM: Homo Sapiens

<400> SEQUENCE: 1

aaagatgatt aaaagtttaa ttgttcatct gaagagttga ttttttttatt cctgtaataa      60

agggtacttt tagcagtctc tgctcatctt gcccatccgg ctctttttgt ggttgtgtaa     120

ggttataact tctgtgtctc agtaaacttg tgcatgccca tttttttctc tgttactacc     180

ttttctctta ttttgtttta ttattttgat gtaaaattac ctgttaattt tatttgaaat     240

gagaaatttt aaggttcaca ttattcaaat tctgtcagat ccctacctct gtcatatggt     300

ttataatgtg ctgggtattt tcagacctgc ttattaaaaa gatgtaaaac aaaataatga     360

tcactcctgt ggatttttcc tttatttttg agatgtctcc tttggctgca ttacttcttc     420

accccttgcc cattgatcag aggaggggtc ttaactatgg gtgaacccta tatcttactg     480

aagaggttat gttacatgta tattttcata atataactta catttacata gtacttttat     540
```

```
ttttagcata ccttttttta ttaatcctaa taatatcact gtaagttatg ttgaagcaga    600

ttgtaagtgt tcatttacaa attgtgaaat gaattaaaat gaaagggcaa agattaaatc    660

atgaccaggc ctgaaattaa cacacaagac tcaatttttt tcaaccaaag acttttgtag    720

gtgatccctg cctgcaggac tccccttcct cctcagatgt cattggattg taccaggttt    780

actgtagatt ctagccgttg tagaactaac tagatctaag atgagtcccc tgatttcctt    840

tggtagagtc ttccaattgc tgaactccaa tattgtcgtg actagccagt gttacaacct    900

gtctgcctta ttttgtgtaa tggatttcat attacagagg catttttta atgtcaagat    960

gtttaagtat tgcttaagtg caaactactt aatacttttt agctattaag taattaagat   1020

aggcaggatt ttatttgttc caaaatgatt tgacctaaac taaaaagaga atgtggatct   1080

cctgaatctt acttggttaa tcttaatata actcctagca ttctataatt cttcctaaag   1140

tcctcttacc tggctatctt ttgtatcttc tttgtctctc ctcttctttc ccagtcataa   1200

taactgccag actctgcttc atttctcttt gacagtctct actcctaagg tcatccattc   1260

tctttaggta tcttttggcc tcagtttgag cacagcagat cccaagacca catatgccat   1320

agcataggct attatagtca acctttgaa taaatgtgat tgaactttat gttagtaatt   1380

cttatttacc atcttcctat caaaaaggct taaagtcttc atttaatgct ctccttcatg   1440

tccattttgt taaatgattg ccttttaatg acatcttaga acttcagaac tatttcacca   1500

tggaggatgt gtaagattag ccttttatca aataaaaagt gtgaaatgga atatgtaatc   1560

tcattaatcc attctggctc taaaattctg tgactatcag ataaaattca gaaataaaat   1620

agtattacta atataaataa atttttatca taattatatt tcctaagttt tgcctgtaag   1680

aatgggtaaa atatctttaa aaccttgaag aaattattac ttgatagaaa gtttaatcca   1740

tctgtgagaa ggcaaatgta ttcagacaca actaaagttc tctcttctat tttaatttca   1800

tttatcttga actaagactc cactgtttca tcctcttaga tgctgctact tgaacaatat   1860

tgttttgaga ccaaaaacta gcatattaac acaattcttc ttaaacgtct taagagtttt   1920

gtttccttta cccctttctt taaaaacaag cagccactaa attttttagt agtgaatttc   1980

aaaatccttt ttaaccttat aggtccaagg gtagccaagg atggctgcag cttcatatga   2040

tcagttgtta aagcaagttg aggcactgaa gatggagaac tcaaatcttc gacaagagct   2100

agaagataat tccaatcatc ttacaaaact ggaaactgag gcatctaata tgaaggtatc   2160

aagactgtga cttttaattg tagtttatcc atttttattc agtattccct cttgtaaact   2220

tgaggtaaga cactttactt aaaagtgtat tttaaattaa gcaataatat gtaaactctt   2280

tcttgcaaaa gttagcattt atatttttaa ataagatata ttgaattcat tcagtgaatc   2340

atataaagaa aataagtgta aaactccaat ggctagttag ttcttagttc tttttaagat   2400

taaagagaag agaccaaata tagcatcact gtactgaggc aaggttttct gtgtagttca   2460

tagaaactag                                                          2470
```

<210> SEQ ID NO 2
<211> LENGTH: 2229
<212> TYPE: DNA
<213> ORGANISM: Homo Sapiens

<400> SEQUENCE: 2

```
tctttcctcg gcgctggctg gtgcgggttg gggtcaggtg gagaagccgc tctttgttaa     60

ggtgacagaa cgtgctgggg gtgggggccg gggccagggc cggtgcaact agggggccgc    120

tgccctttcc tggacacagt ggaagcttct tccgcatcac caaatttttg tcatcctttc    180
```

```
tgagggacct gcttccaggc agcacgcaag ttgttgtccc gggtttactc cgcacccctc    240
tactgggtga ggaaggagca tcttgaatgg agatgggggt gtccccggtt tatacatctg    300
cagagaagag gtgtgccggg ctgcacctct ggaggccgcg gtaactgata ttagagaaga    360
ccccggttgc agctgggaag gctcactggc tggaaagagg tgcctcctcc ttccagcaaa    420
gggccctgtt tggaagggct gcttctcacc tgtctagtgg caccacagga cggtcggctt    480
ccactcgaat tcccccggac ggtatcatca catagccggg tcctcgcagt gttggtttcc    540
caatccgatg actgtcacct cggtgaggac ctgtgctgat ggccggagaa ccctgcgctg    600
cgggcgcaca tggccaggtg gcgcctggca ggcgacgtcc gggtgcagga cggcgctctt    660
accgccccac cccaaaccgt tgcctgggcc taggtccttc ggcttcctga acaggggttt    720
ggggggctaa ggacgctgag gctccggggg caggaagttc tctctggtta agcgttctct    780
cttctctccg gcatacactc ccctacccac ccacctcgcc taccctcggg gcgagaggct    840
caccaaggca gggcgcgccc cccccatgaa tcatcccaag gcctctgagc cgcgggggct    900
ccgggcaact atccccctcc tctcctggcc tcaggcaccc cagtccaggg gtctgcagag    960
aagcccgaag cccggacaaa cgcgccggac gtcaacaacc tctcatccct ggcagcagca   1020
aaggccaata tatttccatt tcttatttca gtttgccacc aaaacaaagc tgcgcgcggc   1080
tgagggcagg aaggcgctga gaccgagaag aagggacgtc ccggagaaag tgcgcccagc   1140
tgatcttaga aaccagagtc ctccgggact tcgccgagat ttctgtaggg gcgttttaat   1200
ctgttttcct actgcgtgcc ggcgtcgcag cgcgtgcggc tcagggcttg gtgactccgg   1260
cttagcccgg cggtcgcggc gaggttcctg gcgcagccgc ttggaacttc gcattagaat   1320
cgggaccgcg caaatgccct ggctgaagtg tcaccctatt caagaaacac tgctgtcagg   1380
aacaaaatgg ggtccccggt gctccgaagt atcttctgaa attttcttaa aacaacttac   1440
aaaaaatgtt tttgctttaa cgttttacaa cgtttaagga aacatgtaaa tggtctgttt   1500
ctttatcgag atggtcgtcc taactaacag tgtacacata cataacaatt cttccaactt   1560
tcctcctcag agctaagcac ttcactatat gtaaattata ataaagaaaa gattgtgcaa   1620
gatcatgcaa gtcgattgac ttaaaatatt gagttttaat ccaggccctc tgtttttcta   1680
tttaacaact tttgtgtttg gaccagactg gtgaagcagg ctatggaaat taacaaagta   1740
aaaaattaaa agcatcttcc ttcgccatcc ctccctccaa aattaaacaa cagtcgcccc   1800
ttcctgagca ggcttcagtc ccaggctcga gttttcctgc gatcacccca cagtcaccca   1860
cagcagctgt tgctgcttct gtcgggtttt cgtttctgcc ttctttgggt cgtctcttgt   1920
atacaaaaca caccccagtt ctctaactaa attcaaatac gaccccggca gaatttacac   1980
atttcgtggt gcatggattg tgtcggtgca ggggaaataa ataccctctg gtatttaacc   2040
actgagtcta attcgaaaaa tcgggactgg gcccctaggc ggcaccccag gggctccaac   2100
ctggcccgcg cctccccaga ccttggcgct gagagcgctg cttttgcggg tgggtggacg   2160
gagaggtaac aatctgcttt caacaaaaac ctgtcgccac cgaatcgaaa gcgaaaggga   2220
agggagaag                                                           2229
```

<210> SEQ ID NO 3
<211> LENGTH: 7833
<212> TYPE: DNA
<213> ORGANISM: Homo Sapiens

<400> SEQUENCE: 3

```
gtctttggtg agatatgtgt tttacaagtt ttaatggaga aaaatgtaag tattttacct     60
```

```
cctgaaactt ggctatttga gtaatgagaa aatagtcact ttccccagga cagtggttct    120
caatcatggc tatgtgtttc tccaggaaaa ctttaaaaat atatatatac caatgcttct    180
gtgtcacttc tagggattcc aagtctttga atacgaactc tgcatcagta ttctttaatt    240
atccaggtga ttgtgatgtg aaatcatgac tgagccccac tgctctaaga tgaaataaac    300
tttcctcagc actgaaatca caaacttaaa ctaccaaaat taattaaggg catgggaatc    360
aataaggcat agggaagctt ttacattata aaattatttc tttaaatcac agctcattgt    420
ttatatgtta tttgccattg tagaaaaggg tgaaaaaata gcaaatttaa ttactctcag    480
tttgaaaaat tatccagaaa tgaagatgac gactctgaaa cattgtcaat atcatttgac    540
ctataaataa tgttctaata catttactac acactgatag atactttttc atatgaatat    600
tatacattaa aactaaggca ataatgcatt tagaacattc tatctatatc tatgtatctt    660
aagtaggcta gaaattaaga tatgagttat taagtatgag atgttaaggt gtggggttag    720
aaattatact gtacttcatt atcaataatc aacatatact tcaatatcac atacatttaa    780
ctttaatttg tacatcttta actattttta attatgtgta taaatataag tacacacatc    840
tttatgtatt tatttattca tacctccatt cacttattta tataggggat ccccccaaat    900
ccactaccat taaaccatac atttttattt taatctttag aacaagccca ggaggcaggt    960
attgttatta ctcacatttt acaaatgagg aaattgtcta cagtcacaaa gttactgtgt   1020
cagacatatt agaagcttaa tacatatttg gtgaacatat gcataaaaac agagagacag   1080
acatgtacaa cagctcatct ttacactgag taaaagcttt taacctgtct cagaaacctc   1140
tctgtgaaaa ctgagcaaaa atcgaggtat cctttcattt gtcatatagg tataggtggt   1200
accttacttc tccaacaagg atgaatattg aaatgtggat cccaaggccc aactccagat   1260
tttctgaatc cctgatagtg ggacttggaa tttgtctatt gtttcaaagt ttctcaagga   1320
attcatatga tcaaccaggt tcagaaatca ctggatctta ttgccgaagt ttgagaatta   1380
aagtttgggc cttactgcgg ctccacagaa agggcaaatg aagtatcatg gacagaactg   1440
atacgttccc agttagtttc ccctctcaga agctaacagg cagcaataca gcagaaatta   1500
gtgacttatg tcttgtgctc tgaagtcagg cagaatttca cagagtccca gcagtgtcac   1560
tgacgagatt tgtttcttgg ggcaagttgc ctgatgcttt caaagccata ttccttttat   1620
ataaaatgag ataatattct ttgtctcata ggggtgtttt aaagattaaa taaaaataac   1680
atgttctatc ctacatggca caatgcctga cacctaagaa gcaaaggata catcttacct   1740
ttattgaagc aatcagaaag tatgaaatca tgaaggagat aagagttctg attggcagtg   1800
tatcttattt tcccaggttc atttatttat cttaaactat tcttgttgga gaataactcc   1860
caagcccccct acttaagctg tgagtaatct cacactttat aatgatgttc tttccatgag   1920
aaaaaaaaat gttcttaagt tttctggaga aaatatatct gcactatttc tactgaaaaa   1980
tctaacaact ggactctgct cctctgcatc aattctagag tgtatatgcc acaaataaag   2040
tgttctagct caagaagatt gaaagtaaat atggtatagt attttaaaat aagaattttg   2100
caaatacatg gtatgattgt gtcatattac tagcaatcat atgatacgca atgcaaagta   2160
cagttcatag acttaaattt aattctaata agtaaactga ttttgccttg ctggggaaaa   2220
gttaaagcac taatccaatt gctaatgcag tcttgtctac ttctttggta cctagtgaca   2280
agtctaaata atgtatatat ttttatttac atattcagta atacaattct ctgctcaatg   2340
agtgatgttc ttctgccact tggtggtgct tgccagtttc agaatttgtt tcttggtggc   2400
actataacac taagtacaga gtaagtgcaa caaaattgca gcattcccat tgaaaaggct   2460
```

```
ttgcttcaaa ctgtttaata atttaaagga cctctgtgga agcaaccgca tttgttaacc   2520
agttacaacc agtaattaac tcctttggag ttttaactta cttttggcaa aacgtcttag   2580
gaagagcata tattattaga aagtatgcca aaaatttact tagcagaaaa ttcaaaaaca   2640
gttttcctct gctaagaggt tctctaaaat tctacttaca tagccaaact ctgaaatcct   2700
agcaggtcct gtttcattat cataattact gcataaacac ttttaaggac tttgccttta   2760
gtttcaagca tgacttattt tcataagcct gattagttac cacaccagcc ttgctatgga   2820
aaatgacatg ttctcattct ctgctgtaga gttgttaaat cttgatctat atttatgttg   2880
ccttctctgc tgaaagcctg tagcgaaaga aatttctaat tccttgtttt gcaatattag   2940
ttggcagctc tatctaatgg gtattctgtt tccttaaaga atttagctgc tctgtctaga   3000
agccgatttt ctgatgcctc caacgtctgg tctaattgat ctgttttaat ggagtcttcg   3060
tcggtgagga gcgagatgcc accgactaga atgctgggat ctgctgctta attgccagga   3120
gtgagagaca ctgagattca gaaatctttg gaggtgggag gggagaggga cagtctcgga   3180
cggaggcgga gatgtaagat aaagggatgg atttcacaca ggaaaaaaaa aaagatttcg   3240
ttgaggcact gaggtgctgc acgatcacat ctctcaaagg agaagttaaa aagcaaggaa   3300
gtgggaggag gttggaggtt aaagtactta aaaggattac tcgggtacaa tttgtttttc   3360
tgctggtgtc tgcaaaggat agatagtccc gttttcaaag tatatgaatg cctcttttaa   3420
gtgattggga atggacacta attgcctgtt aaatgttatc aaatgctctc ctaaattcag   3480
gggacacaga aagaggggca caaaaggaga atttaaatag aaaaagggag gatccggagg   3540
cttttgaaag cggggggaga agaaggagga gggataacag agaggaatag agaaggagag   3600
cggagagaag ataaacaaaa acaaaaacag gaatcactga ataatcacac accaaaaaga   3660
aagctcttcc ctatggggca tccaaaacac tgagactgca atagtgaccc cggtcatgga   3720
agaaagatgt tcctctccac ccttgtcccc gaaagctctt ggtcccgtta ctggcgacta   3780
aaattccatt aggctaaaga gtgtgtctaa ctgcctgaag aatgcagcag acggaaggcg   3840
ggtcccgcta tgccgtttgc ccttcccgct ggagagaatg aaagaaacgc gcagagccag   3900
agactcctgc cgagttagac cttctctcgt cgccccaggt caccggccat ccggcaaaga   3960
cccgagtaag gaacgcaggg tcactgcctg ggccaacaaa tggagcccgc tctccccttc   4020
ccggacgccg ctgcccggcc gatgctcccg gcaacccacc cgcggcgtat gcagaggagc   4080
ctttctcttt ctctcagacc acttgtcccg accaatctga ccttccaaac acatctgacc   4140
gcacctccca ggtggacaca ctaataggct acgggctgga gaggagcggg tgatgaggag   4200
agggattcaa acctgcgaac gcttgggctg ggtcggagct gcggggggcc tgggaggaga   4260
gaggggagaa gagagaagga aggagagcgc ctgccgggat ggctgagctg cctcggcgag   4320
cagccttggg gttgcacgct cttgtgggag atgctgctgt tgcttccagg tcggcaagag   4380
cggttctaac accatcgcct ctcaccctct ttcctgtaaa tccctagaga aacgtccctg   4440
gcctctccgc cgcgacattc ccagcctgca tccccctaca gcctaggcgg cgcgctcccg   4500
cacgctggag cgccggtcgc cagcaggacg ccctctcccg cgccgactcg cccctctctg   4560
ccctgctgct gctgctcctc tgacacctcc gcccccacca tctccagctc ggagagacgc   4620
cacccagccg cggcccgcac tcgcggcccg gggtcacgcg cggaagaggg gcgctagtcc   4680
ggaccccgcc ttcggtaggg ggcgtcctgg agcggagagt gaggcgaatg gtatatgagt   4740
gtgcgggtag cccaccctga agcccgagct tctcatttga gccatgcccc gcctagcccc   4800
actcgggcca gcgcctggcg agcgagccca tctgtggctt ccgcggccgc ctcctccttg   4860
```

```
catccttgca cctactcgtc gacccctccc tcccgggacc tgcatcctgc tccaccaatc   4920
agagcccgac tgcctcttcc cacgtgaccc cgggcgggct gaggacctgc tgcttcccaa   4980
acgccagagg gatgcgggcg gcagagctcg agaggcggct gccgggctgc ggggcgcctt   5040
gactctccct ccaccctgcc tcctcgggct ccactcgtct gcccctggac tcccgtctcc   5100
tcctgtcctc cggcttccca gagctccctc cttatggcag cagcttcccg cgtctccggc   5160
gcagcttctc agcggacgac cctctcgctc cggggctgag cccagtccct ggatgttgct   5220
gaaactctcg agatcatgcg cgggtttggc tgctgcttcc ccgccgggtg ccactgccac   5280
cgccgccgcc tctgctgccg ccgtccgcgg gatgctcagt agcccgctgc ccggcccccg   5340
cgatcctgtg ttcctcggaa gccgtttgct gctgcagagt tgcacgaact agtcatggtg   5400
ctgtgggagt ccccgcggca gtgcagcagc tggacacttt gcgagggctt ttgctggctg   5460
ctgctgctgc ccgtcatgct actcatcgta gcccgcccgg tgaagctcgc tgctttccct   5520
acctccttaa gtgactgcca aacgcccacc ggctggaatt gctctggtaa gtccagaacc   5580
cccgtccccg accctttaac tccgcagaag aacacgcgta tccagcacag accagcctac   5640
cctagcgcgc ctcctcagcc cctcacctcc tactgcccta gaccccctaat accacccacc   5700
tctatccaga gaaacaaggg gaactgttgc aggcccgggg gtgaggggtg gttctgggat   5760
gggcagaaag tgcaggtgta gcaggaaacc tttgcatgct tgcgcttaca ttggagctgc   5820
gaggattttg agaaatatta aacgggatgg ttttctgggt tcactgtttt gaaagagcac   5880
caatcctagg ggaaacactg aaacagaagc tttgtcatca ttaaagaaaa aagtcttact   5940
aggatgagga agaaataact ttatgagaaa gaatgagcga gaaagcaata aatcaaatgg   6000
tgactgcagg ggaatcgctg attcctggca aaggtgccat gaggtcgcac tggtctcccg   6060
ttgaagacca ggtcacacag attctagagg agctgggttt caatagaatt tctctctctc   6120
tctctctctc tctctctctc tctctctctc tctctctatc tatctatctc tctctctctc   6180
tcattccctt ctctcctagg cggcaaaaga cattggtttt gcagtccaga tatgcccctc   6240
tctttgcttc cctaagcttc aaggtagtac aggggagttg agaaaaagaa cactttgcgg   6300
gtctcccagg ccggagtggg catgactgag gctggtcagg ctccatgtag gcgagccgag   6360
ggcggaaccg acttcagtgg gcgctgactc ctccatttct ggacaggctt ctgtggagtg   6420
ggtcaggcac tcttcttgct cgctcgggtt ccttcagatt ctgacggcga acgcttggca   6480
ggcttcgctc tgctgaagct tcctaattaa atagggccag aggatgggag ttgctgcact   6540
cctagctggc atagcattcg gtttgacagc ctgtagtata gggtgtatgt aatttttcat   6600
cttctgtgaa tataattttg ctgtagttaa atctggctct gaataaagtg tctttcaaag   6660
atgtatataa gctgaagtgt atgtaacttt agagaggagg gaatgaccaa ctgtaactca   6720
gggtgaaagc ctgtatagtt cctagttatt actgatgtaa atgccaaaag gaaaattatt   6780
atgcatcatt ctaatttatc ctttacaaag acaagttgag atatgcaacc ctattagatt   6840
tgggtcaata gattgttctc ttttttggca gtttctaaat ttggcatttt aataaaactc   6900
aacatgtttc tataacttct tgattcatgc gtacatgtgt gttgtttttg aaagaataag   6960
tttcactttg ctattgccta atcacttttt agatgcttta ttatggtaat aattatgagc   7020
ctgcaaaaac aatttttgga aatgttgatg gctttgtagt ccaacacaga ctggtttgct   7080
tcattcctag cccttgcatt gttttaggaa ataactaact taaatgtgaa gttgacattt   7140
gcaatcaaga aattacatat ttaccagata ttttaaaggg gactgcataa actaaagaga   7200
ataaactggt tttgcagata ggttgtcaag aacttggcac cccgcttcca cccctgttaa   7260
```

```
cttagaggtg atcaatcttc atttgagcca aacagaccat cacagaaaac actgtgcctg   7320

tttatcttta ttattgaggc tttgtttcct ctttgtctgg atacatttca aataaggggt   7380

tgtttcagtc gttgaagcaa aagaacaatt aaagatgggg aaatggtaaa agggtattca   7440

gagatcatca ctagctcttt tccaaaatgt ggagttttgt ggtcataaat attgtccacc   7500

taatgagcaa aaaataaaaa taaaaaaaaa acaggaagca aatgttaagc tttcattcac   7560

cactgtcagt attaacgcaa gctttaaaaa atagcactat cagaaaagga tactaaagga   7620

gaattgacta gaaaagaatt gtggaaaatg gaaacgaata ttgatcactt aactagattt   7680

tgaggttatc agtagacagt gaccttgcag tacagctata gttgttggat ttaaaattta   7740

ggacaagtat tttaaagctt caaagtagtg cttttttttg ttaaaaatct gtaagatgtt   7800

ttaatgactg gagtgttctc tttgaatttg agg                                  7833
```

<210> SEQ ID NO 4
<211> LENGTH: 5666
<212> TYPE: DNA
<213> ORGANISM: Homo Sapiens

<400> SEQUENCE: 4

```
aaaattagaa cttttacctc cttgcgcttg ttatactctt tagtgctgtt taacttttct     60

ttgtaagtga gggtggtgga gggtgcccat aatcttttca gggagtaagt tcttcttggt    120

ctttctttct ttctttcttt cttttttttct tgagaccaag tttcgctctt gtctcccagg   180

ctggagtgca atggcgcgat ctcggctcac tgcaacctcc gccttctcct gggttcaagc    240

gattctccta catcagcctc cgagtagctg ggattacagg catgcgccac caagccccgc    300

taattttgta ttttttagta gagacagggt ttcgccatgt tggtcaggct tgtctcgaac    360

tcctggcctc aggtgatccg cctgtctcgg cctcccagaa tgctgggatt atagacgtga    420

gccaccgcat ccggactttc cttttatgta atagtgataa ttctatccaa agcatttttt    480

tttttttttg agtcggagtc tcattctgtc acccaggctg gagggtggtg gcgcgatctc    540

ggcttactgc aacctctgcc tcccgggttc aagcgattct cctgcctcag cctcctgagt    600

agctggaatt acacacgtgc gccaccatgg ccagctaatt tttgtatttt tagtagagac    660

ggggtgtcac cattttggcc aagctggcct cgaactcctg acctcaggtg atctgcccgc    720

ctcggcttcc caaagtgctg ggattacagg tgtgagccac cgcgtcctgc tccaaagcat    780

tttctttcta tgcctcaaaa caagattgca agccagtcct caaagcggat aattcaagag    840

ctaacaggta ttagcttagg atgtgtggca ctgttcttaa ggcttatatg tattaataca    900

tcatttaaac tcacaacaac ccctataaag caggggggcac tcatattccc ttcccccttt   960

ataattacga aaaatgcaag gtattttcag taggaaagag aaatgtgaga agtgtgaagg   1020

agacaggaca gtatttgaag ctggtctttg gatcactgtg caactctgct tctagaacac   1080

tgagcacttt ttctggtcta ggaattatga ctttgagaat ggagtccgtc cttccaatga   1140

ctccctcccc attttcctat ctgcctacag gcagaattct cccccgtccg tattaaataa   1200

acctcatctt ttcagagtct gctcttatac caggcaatgt acacgtctga gaaacccttg   1260

ccccagacag ccgttttaca cgcaggaggg gaaggggagg ggaaggagag agcagtccga   1320

ctctccaaaa ggaatccttt gaactagggt ttctgactta gtgaaccccg cgctcctgaa   1380

aatcaagggt tgagggggta gggggacact ttctagtcgt acaggtgatt tcgattctcg   1440

gtggggctct cacaactagg aaagaatagt tttgcttttt cttatgatta aaagaagaag   1500

ccatactttc cctatgacac caaacacccc gattcaattt ggcagttagg aaggttgtat   1560
```

```
cgcggaggaa ggaaacgggg cgggggcgga tttcttttta acagagtgaa cgcactcaaa   1620
cacgcctttg ctggcaggcg ggggagcgcg gctgggagca gggaggccgg agggcggtgt   1680
ggggggcagg tggggaggag cccagtcctc cttccttgcc aacgctggct ctggcgaggg   1740
ctgcttccgg ctggtgcccc cgggggagac ccaacctggg gcgacttcag ggtgccaca    1800
ttcgctaagt gctcggagtt aatagcacct cctccgagca ctcgctcacg gcgtcccctt   1860
gcctggaaag ataccgcggt ccctccagag gatttgaggg acagggtcgg agggggctct   1920
tccgccagca ccggaggaag aaagaggagg ggctggctgg tcaccagagg gtggggcgga   1980
ccgcgtgcgc tcggcggctg cggagagggg gagagcaggc agcgggcggc ggggagcagc   2040
atggagccgg cggcggggag cagcatggag ccttcggctg actggctggc cacggccgcg   2100
gcccggggtc gggtagagga ggtgcgggcg ctgctggagg cgggggcgct gcccaacgca   2160
ccgaatagtt acggtcggag gccgatccag gtgggtagag ggtctgcagc gggagcaggg   2220
gatggcgggc gactctggag gacgaagttt gcaggggaat tggaatcagg tagcgcttcg   2280
attctccgga aaaaggggag gcttcctggg gagttttcag aaggggtttg taatcacaga   2340
cctcctcctg gcgacgccct gggggcttgg gaagccaagg aagaggaatg aggagccacg   2400
cgcgtacaga tctctcgaat gctgagaaga tctgaagggg ggaacatatt tgtattagat   2460
ggaagtatgc tctttatcag atacaaaatt tacgaacgtt tgggataaaa agggagtctt   2520
aaagaaatgt aagatgtgct gggactactt agcctccaat tcacagatac ctggatggag   2580
cttatctttc ttactaggag ggattatcag tggaaatctg tggtgtatgt tggaataaat   2640
atcgaatata aattttgatc gaaattattc agaagcggcc gggcgcggtg cctcacgcct   2700
tgtaatccct tcactttggg agatcaaggc ggggggaatc acctgaggtc gggagttcga   2760
gaccagcctg gccaacaggt gaaacctcgc ctctactaaa aatacaaaaa gtagccgggg   2820
gtggtggcag gcgcctgtaa tcccagctac tcgggaggtt gaggcaggag aatcgcttga   2880
acccgggagg ctgaggttgt agtgaacagc gagatggagc cacttcactc cagcctgggt   2940
gacagagtga gactttgtcg aaagaaagaa agagagaaag agagagagaa aaattattca   3000
gaagcaacta catattgtgt ttatttttaa ctgagtaggg caaataaata tatgtttgct   3060
gtaggaactt aggaaataat gagccacatt catgtgatca ttccagaggt aatatgtagt   3120
taccattttg ggaatatctg ctaacatttt tgctctttta ctatctttag cttacttgat   3180
atagtttatt tgtgataaga gttttcaatt cctcattttt gaacagaggt gtttctcctc   3240
tccctactcc tgttttgtga gggagttagg ggaggattta aaagtaatta atacatgggt   3300
aacttagcat ctctaaaatt ttgccaacag cttgaacccg ggagtttggc tttgtagtcc   3360
tacaatatct tagaagagac cttatttgtt taaaaacaaa aaggaaaaag aaaagtggat   3420
agttttgaca atttttaatg gagaagggag aagaacatgt agaaaagggg aaatgatgtt   3480
ggcttagaat cctaactaca ttggtgttta atataggaac atttatttat ataacatttt   3540
aaagtactaa attcatatta gtatattatc aaatggatat attatcaaat gggtttaagc   3600
atcctacaca ttttaattca attgattcat tttctttttg ctttggattt ctatcatgat   3660
ttaaatattt acatatgggt tactttttag atttttcata ctatgaaata taagaaaaac   3720
ctttaaggct agttttatga ccaagacgaa ggacttcatt gaatacacaa aacaataaat   3780
atactgcaac attttgtctt tctttttgta gctgcaattt ggtttgctta tactttctct   3840
ttgtctcttt gaaaactgag tcagtttcac tttctcagga caggatttaa taaccataat   3900
ataatttagt ataattcctt gatttaggca aattatgcaa tttgtgttta gtatgaaatg   3960
```

```
tacctaaaaa taagtaactc ctctttaaca ccaccatcct caaactaata taacaaataa   4020
cagttatcct aaaataaatt gtctacttcc accatgcagc actcaaattt taaggttgct   4080
atgactgcag acagtatttt aaaattcctc tctggaaatg gctttgtttc caagatgatt   4140
taggaaccaa agaggtgacc atctcttgtt taatgaactc tcaaatcata aacctgggaa   4200
gtgttttagt ttcctactgc tgctgttaca aattatcaca aatgtgttag ctaaaacaaa   4260
cacaaaatta ttattttaca gttctagaga tcagaagtca aaaatgggtc cacaaggttt   4320
cattcctttt ggaaactcta aggggcaatc tgtttccttg tcttttccag cttctagtga   4380
ccatcaaatt ccttggctca tggtctctgt attttctctg tggcctgtgc ttccattctt   4440
gtatcttctc tctgactgtg accctctaat aaaaacactt ggggttatgt tgggcccacc   4500
ctgaaaattc tggataatct ccctcaagac cattaattaa atcacatctg caaagcctct   4560
tttgccacat aagttaatgt attaaaagtt tttgaggatt aggacataga cattgggggt   4620
ggggggcat tattcagcct accacaggaa ggaattttag ggttaattaa actagccttc   4680
ttattttata cttgaagaaa ttgaagtttt ggaattggag agcattatgc taaatgaaat   4740
aagccaaaca cagaaagaca aatatcacat gttctcactt atctgtgaaa tataaaacaa   4800
ttacattctt agcagtaaag agtagaatgg tggttactag agctgggggg tgggaggaat   4860
ggggagatgg taatcaagat ataaagcctc agttaagatg ggaggaataa gtttgattgt   4920
tttttttgag atgtgtttca tagcatgatg aatatagcta aatagtaaat cccaaatgct   4980
ctcatttgac aaaaatgtca aatatttgag atgatggata ggttacttag cttgacttaa   5040
taattcccca ttgtgttcaa agatcataac ttcatattgt accacataaa tatatacaac   5100
tgtactatcc caatatataa ttttaaaact aatataatga aaaagaaatt gaagttcaac   5160
attcccagaa gctaagtgta acttaaaagt tttgtgagaa tttgttttaa caaacaaaca   5220
agttttctct ttttaacaat taccacattc tgcgcttgga tatacagcag tgaacaaaaa   5280
aaaaaaaaaa aaaaaaaatc tccaggccta acataatttc aggaagaaat ttcagtagtt   5340
gtatctcagg ggaaatacag gaagttagcc tggagtaaaa gtcagtctgt ccctgcccct   5400
ttgctatttt gcccgtgcct cacagtgctc tctgcctgtg acgacagctc cgcagaagtt   5460
cggaggatat aatggaattc attgtgtact gaagaatgga tagagaactc aagaaggaaa   5520
ttggaaactg gaagcaaatg taggggtaat tagacacctg ggcttgtgt gggggtctgc   5580
ttggcggtga gggggctcta cacaagcttc ctttccgtca tgccggcccc caccctggct   5640
ctgaccattc tgttctctct ggcagg                                         5666
```

<210> SEQ ID NO 5
<211> LENGTH: 2470
<212> TYPE: DNA
<213> ORGANISM: Artificial Sequence
<220> FEATURE:
<223> OTHER INFORMATION: chemically treated genomic DNA (Homo sapiens)

<400> SEQUENCE: 5

```
aaagatgatt aaaagtttaa ttgtttattt gaagagttga ttttttatt tttgtaataa   60
agggtatttt tagtagtttt tgtttatttt gtttattcgg tttttttgt ggttgtgtaa   120
ggttataatt tttgtgtttt agtaaatttg tgtatgttta tttttttttt tgttattatt   180
ttttttttta ttttgtttta ttattttgat gtaaaattat ttgttaattt tatttgaaat   240
gagaaatttt aaggtttata ttatttaaat tttgttagat ttttattttt gttatatggt   300
ttataatgtg ttgggtattt ttagatttgt ttattaaaaa gatgtaaaat aaaataatga   360
```

-continued

```
ttatttttgt ggattttttt tttatttttg agatgttttt tttggttgta ttattttttt    420
atttttgtt tattgattag aggaggggtt ttaattatgg gtgaatttta tattttattg    480
aagaggttat gttatatgta tatttttata atataattta tatttatata gtatttttat    540
ttttagtata ttttttttta ttaattttaa taatattatt gtaagttatg ttgaagtaga    600
ttgtaagtgt ttatttataa attgtgaaat gaattaaaat gaaagggtaa agattaaatt    660
atgattaggt ttgaaattaa tatataagat ttaatttttt ttaattaaag atttttgtag    720
gtgatttttg tttgtaggat tttttttttt ttttagatgt tattggattg tattaggttt    780
attgtagatt ttagtcgttg tagaattaat tagatttaag atgagttttt tgattttttt    840
tggtagagtt ttttaattgt tgaattttaa tattgtcgtg attagttagt gttataattt    900
gtttgtttta ttttgtgtaa tggattttat attatagagg tatttttttta atgttaagat    960
gtttaagtat tgtttaagtg taaattattt aatatttttt agttattaag taattaagat   1020
aggtaggatt ttatttgttt taaaatgatt tgatttaaat taaaaagaga atgtggattt   1080
tttgaatttt atttggttaa ttttaatata atttttagta ttttataatt ttttttaaag   1140
ttttttttatt tggttatttt ttgtattttt tttgtttttt tttttttttt ttagttataa   1200
taattgttag attttgtttt attttttttt gatagttttt atttttaagg ttatttattt   1260
tttttaggta ttttttggtt ttagtttgag tatagtagat tttaagatta tatatgttat   1320
agtataggtt attatagtta attttttgaa taaatgtgat tgaattttat gttagtaatt   1380
tttatttatt atttttttat taaaaaggtt taaagttttt atttaatgtt tttttttatg   1440
tttattttgt taaatgattg tttttttaatg atattttaga attttagaat tattttatta   1500
tggaggatgt gtaagattag ttttttatta aataaaaagt gtgaaatgga atatgtaatt   1560
ttattaattt attttggttt taaaattttg tgattattag ataaaattta gaaataaaat   1620
agtattatta atataaataa atttttatta taattatatt ttttaagttt tgtttgtaag   1680
aatgggtaaa atatttttaa aattttgaag aaattattat ttgatagaaa gtttaattta   1740
tttgtgagaa ggtaaatgta tttagatata attaaagttt ttttttttat tttaatttta   1800
tttattttga attaagattt tattgtttta ttttttttaga tgttgttatt tgaataatat   1860
tgttttgaga ttaaaaatta gtatattaat ataatttttt ttaaacgttt taagagtttt   1920
gtttttttta tttttttttt taaaaataag tagttattaa attttttagt agtgaatttt   1980
aaaatttttt ttaattttat aggtttaagg gtagttaagg atggttgtag ttttatatga   2040
ttagttgtta aagtaagttg aggtattgaa gatggagaat ttaaattttc gataagagtt   2100
agaagataat tttaattatt ttataaaatt ggaaattgag gtatttaata tgaaggtatt   2160
aagattgtga tttttaattg tagtttattt atttttattt agtatttttt tttgtaaatt   2220
tgaggtaaga tattttattt aaaagtgtat tttaaattaa gtaataatat gtaaattttt   2280
ttttgtaaaa gttagtattt atatttttaa ataagatata ttgaatttat ttagtgaatt   2340
atataaagaa aataagtgta aaattttaat ggttagttag tttttagttt tttttaagat   2400
taaagagaag agattaaata tagtattatt gtattgaggt aaggtttttt gtgtagttta   2460
tagaaattag                                                           2470
```

<210> SEQ ID NO 6
<211> LENGTH: 2470
<212> TYPE: DNA
<213> ORGANISM: Artificial Sequence
<220> FEATURE:
<223> OTHER INFORMATION: chemically treated genomic DNA (Homo sapiens)

<400> SEQUENCE: 6

```
ttagttttta tgaattatat agaaaatttt gttttagtat agtgatgtta tatttggttt     60
ttttttttta attttaaaaa gaattaagaa ttaattagtt attggagttt tatatttatt    120
tttttatat gatttattga atgaatttaa tatattttat ttaaaaatat aaatgttaat    180
ttttgtaaga aagagtttat atattattgt ttaatttaaa atatattttt aagtaaagtg    240
ttttatttta agtttataag agggaatatt gaataaaaat ggataaatta taattaaaag    300
ttatagtttt gatattttta tattagatgt tttagttttt agttttgtaa gatgattgga    360
attatttttt agtttttgtc gaagatttga gtttttttatt tttagtgttt taatttgttt    420
taataattga ttatatgaag ttgtagttat ttttggttat ttttggattt ataaggttaa    480
aaaggatttt gaaatttatt attaaaaaat ttagtggttg tttgttttta aagaaagggg    540
taaaggaaat aaaattttta agacgtttaa gaagaattgt gttaatatgt tagtttttgg    600
ttttaaaata atattgttta agtagtagta tttaagagga tgaaatagtg gagttttagt    660
ttaagataaa tgaaattaaa atagaagaga gaattttagt tgtgtttgaa tatatttgtt    720
tttttataga tggattaaat tttttattaa gtaataattt ttttaaggtt ttaaagatat    780
tttatttatt tttataggta aaatttagga aatataatta tgataaaaat ttatttatat    840
tagtaatatt attttatttt tgaattttat ttgatagtta tagaatttta gagttagaat    900
ggattaatga gattatatat tttattttat atttttttatt tgataaaagg ttaattttat    960
atatttttta tggtgaaata gttttgaagt tttaagatgt tattaaaagg taattattta   1020
ataaaatgga tatgaaggag agtattaaat gaagatttta agtttttttg ataggaagat   1080
ggtaaataag aattattaat ataaagttta attatattta tttaaaaggt tgattataat   1140
agtttatgtt atggtatatg tggttttggg atttgttgtg tttaaattga ggttaaaaga   1200
tatttaaaga gaatggatga ttttaggagt agagattgtt aaagagaaat gaagtagagt   1260
ttggtagtta ttatgattgg gaaagaagag gagagataaa gaagatataa aagatagtta   1320
ggtaagagga ttttaggaag aattatagaa tgttaggagt tatattaaga ttaattaagt   1380
aagatttagg agatttatat ttttttttta gtttaggtta aattattttg gaataaataa   1440
aattttgttt attttaatta tttaatagtt aaaaagtatt aagtagtttg tatttaagta   1500
atatttaaat attttgatat taaaaaaatg tttttgtaat atgaaattta ttatataaaa   1560
taaggtagat aggttgtaat attggttagt tacgataata ttggagttta gtaattggaa   1620
gattttatta aaggaaatta ggggatttat tttagattta gttagtttta taacggttag   1680
aatttatagt aaatttggta taatttaatg atatttgagg aggaagggga gttttgtagg   1740
tagggattat ttataaaagt ttttggttga aaaaaattga gttttgtgtg ttaattttag   1800
gtttggttat gatttaattt ttgttttttt attttaattt attttataat ttgtaaatga   1860
atatttataa tttgttttaa tataatttat agtgatatta ttaggattaa taaaaaaagg   1920
tatgttaaaa ataaaagtat tatgtaaatg taagttatat tatgaaaata tatatgtaat   1980
ataatttttt tagtaagata tagggtttat ttatagttaa gatttttttt ttgattaatg   2040
ggtaaggggt gaagaagtaa tgtagttaaa ggagatattt taaaaataaa ggaaaaattt   2100
ataggagtga ttattatttt gttttatatt tttttaataa gtaggtttga aaatatttag   2160
tatattataa attatatgat agaggtaggg atttgataga atttgaataa tgtgaatttt   2220
aaaatttttt attttaaata aaattaatag gtaattttat attaaaataa taaaataaaa   2280
taagagaaaa ggtagtaata gagaaaaaaa tgggtatgta taagtttatt gagatataga   2340
```

agttataatt ttatataatt ataaaaagag tcggatgggt aagatgagta gagattgtta 2400
aaagtatttt ttattatagg aataaaaaaa ttaattttt agatgaataa ttaaattttt 2460
aattattttt 2470

<210> SEQ ID NO 7
<211> LENGTH: 2229
<212> TYPE: DNA
<213> ORGANISM: Artificial Sequence
<220> FEATURE:
<223> OTHER INFORMATION: chemically treated genomic DNA (Homo sapiens)

<400> SEQUENCE: 7 tttttttcg gcgttggttg gtgcgggttg gggttaggtg gagaagtcgt tttttgttaa 60
ggtgatagaa cgtgttgggg gtgggggtcg gggttagggt cggtgtaatt agggggtcgt 120
tgtttttttt tggatatagt ggaagttttt ttcgtattat taaatttttg ttattttttt 180
tgagggattt gtttttaggt agtacgtaag ttgttgtttc gggtttattt cgtatttttt 240
tattgggtga ggaaggagta ttttgaatgg agatgggggt gttttcggtt tatatatttg 300
tagagaagag gtgtgtcggg ttgtattttt ggaggtcgcg gtaattgata ttagagaaga 360
tttcggttgt agttgggaag gtttattggt tggaaagagg tgtttttttt ttttagtaaa 420
gggttttgtt tggaagggtt gtttttttatt tgtttagtgg tattatagga cggtcggttt 480
ttattcgaat tttttcggac ggtattatta tatagtcggg ttttcgtagt gttggttttt 540
taattcgatg attgttattt cggtgaggat ttgtgttgat ggtcggagaa ttttgcgttg 600
cgggcgtata tggttaggtg gcgtttggta ggcgacgttc gggtgtagga cggcgttttt 660
atcgttttat tttaaatcgt tgtttgggtt taggtttttc ggtttttga ataggggttt 720 ggggggttaa ggacgttgag gtttcggggg taggaagttt tttttggtta agcgtttttt 780 tttttttcg gtatatattt ttttatttat ttatttcgtt tattttcggg gcgagaggtt 840
tattaaggta gggcgcgttt tttttatgaa ttattttaag gtttttgagt cgcgggggtt 900
tcgggtaatt attttttttt ttttttggtt ttaggtattt tagtttaggg gtttgtagag 960
aagttcgaag ttcggataaa cgcgtcggac gttaataatt ttttattttt ggtagtagta 1020
aaggttaata tatttttatt ttttatttta gtttgttatt aaaataaagt tgcgcgcggt 1080
tgagggtagg aaggcgttga gatcgagaag aagggacgtt tcggagaaag tgcgtttagt 1140
tgattttaga aattagagtt tttcgggatt tcgtcgagat tttttgtagg gcgttttaat 1200 ttgtttttttt attgcgtgtc ggcgtcgtag cgcgtgcggt ttagggtttg gtgatttcgg 1260
tttagttcgg cggtcgcggc gaggtttttg gcgtagtcgt ttggaatttc gtattagaat 1320
cgggatcgcg taaatgtttt ggttgaagtg ttattttatt taagaaatat tgttgttagg 1380
aataaaatgg ggttttcggt gtttcgaagt attttttgaa atttttttaa aataatttat 1440
aaaaaatgtt tttgttttaa cgttttataa cgtttaagga aatatgtaaa tggtttgttt 1500
ttttatcgag atggtcgttt taattaatag tgtatatata tataataatt tttttaattt 1560
ttttttttag agttaagtat tttattatat gtaaattata ataaagaaaa gattgtgtaa 1620
gattatgtaa gtcgattgat ttaaaatatt gagttttaat ttaggttttt tgttttttta 1680
tttaataatt tttgtgtttg gattagattg gtgaagtagg ttatggaaat taataaagta 1740
aaaaattaaa agtatttttt ttcgttattt ttttttttaa aattaaataa tagtcgtttt 1800
tttttgagta ggttttagtt ttaggttcga gtttttttgc gattatttta tagttattta 1860
tagtagttgt tgttgttttt gtcgggtttt cgtttttgtt ttttttgggt cgtttttttgt 1920

```
atataaaata tattttagtt ttttaattaa atttaaatac gatttcggta gaatttatat   1980

atttcgtggt gtatggattg tgtcggtgta ggggaaataa atattttttg gtatttaatt   2040

attgagttta attcgaaaaa tcgggattgg gtttttaggc ggtattttag gggttttaat   2100

ttggttcgcg ttttttttaga ttttggcgtt gagagcgttg tttttgcggg tgggtggacg   2160

gagaggtaat aatttgtttt taataaaaat ttgtcgttat cgaatcgaaa gcgaaaggga   2220

agggagaag                                                            2229
```

<210> SEQ ID NO 8
<211> LENGTH: 2229
<212> TYPE: DNA
<213> ORGANISM: Artificial Sequence
<220> FEATURE:
<223> OTHER INFORMATION: chemically treated genomic DNA (Homo sapiens)

<400> SEQUENCE: 8

```
ttttttttt ttttttcgtt ttcgattcgg tggcgatagg tttttgttga aagtagattg     60

ttattttttc gtttatttat tcgtaaaagt agcgttttta gcgttaaggt ttggggaggc    120

gcgggttagg ttggagtttt tggggtgtcg tttaggggtt tagtttcgat ttttcgaatt    180

agatttagtg gttaaatatt agagggtatt tatttttttt gtatcgatat aatttatgta    240

ttacgaaatg tgtaaatttt gtcggggtcg tatttgaatt tagttagaga attggggtgt    300

gttttgtata taagagacga tttaaagaag gtagaaacga aaattcgata gaagtagtaa    360

tagttgttgt gggtgattgt ggggtgatcg taggaaaatt cgagtttggg attgaagttt    420

gtttaggaag gggcgattgt tgtttaattt tggagggagg gatggcgaag gaagatgttt    480

ttaatttttt attttgttaa tttttatagt ttgttttatt agtttggttt aaatataaaa    540

gttgttaaat agaaaaatag agggtttgga ttaaaattta atattttaag ttaatcgatt    600

tgtatgattt tgtataattt tttttttatt ataatttata tatagtgaag tgtttagttt    660

tgaggaggaa agttggaaga attgttatgt atgtgtatat tgttagttag gacgattatt    720

tcgataaaga aatagattat ttatatgttt ttttaaacgt tgtaaaacgt taaagtaaaa    780

atatttttttg taagttgttt taagaaaatt ttagaagata tttcggagta tcggggattt    840

tattttgttt ttgatagtag tgttttttga atagggtgat atttagtta gggtatttgc     900

gcggtttcga ttttaatgcg aagttttaag cggttgcgtt aggaatttcg tcgcgatcgt    960

cgggttaagt cggagttatt aagttttgag tcgtacgcgt tgcgacgtcg gtacgtagta   1020

ggaaaataga ttaaaacgtt ttatagaaaa tttcggcgaa gtttcggagg attttggttt   1080

ttaagattag ttgggcgtat ttttttcggg acgttttttt ttttcggttt tagcgttttt   1140

ttgtttttag tcgcgcgtag ttttgttttg gtggtaaatt gaaataagaa atggaaatat   1200

attggttttt gttgttgtta gggatgagag gttgttgacg ttcggcgcgt ttgttcgggt   1260

ttcgggtttt tttgtagatt tttggattgg ggtgtttgag gttaggagag gagggggata   1320

gttgttcgga gttttcgcgg tttagaggtt ttgggatgat ttatgggggg ggcgcgtttt   1380

gttttggtga gtttttcgtt tcgagggtag gcgaggtggg tgggtagggg agtgtatgtc   1440

ggagagaaga gagaacgttt aattagagag aattttttgt tttcggagtt ttagcgtttt   1500

tagtttttta aatttttgtt taggaagtcg aaggatttag gtttaggtaa cggtttgggg   1560

tggggcggta agagcgtcgt tttgtattcg gacgtcgttt gttaggcgtt atttggttat   1620

gtgcgttcgt agcgtagggt ttttcggtta ttagtatagg tttttatcga ggtgatagtt   1680

atcggattgg gaaattaata ttgcgaggat tcggttatgt gatgatatcg ttcgggggaa   1740
```

```
ttcgagtgga agtcgatcgt tttgtggtgt tattagatag gtgagaagta gttttttttaa   1800
atagggtttt ttgttggaag gaggaggtat ttttttttag ttagtgagtt tttttagttg   1860
taatcggggt tttttttaat attagttatc gcggttttta gaggtgtagt tcggtatatt   1920
tttttttgt agatgtataa atcggggata tttttatttt tatttaagat gttttttttt   1980
tatttagtag aggggtgcgg agtaaattcg ggataataat ttgcgtgttg tttggaagta   2040
ggttttttag aaaggatgat aaaaatttgg tgatgcggaa gaagttttta ttgtgtttag   2100
gaaagggtag cggtttttta gttgtatcgg ttttggtttc ggtttttatt tttagtacgt   2160
tttgttattt taataaagag cggttttttt atttgatttt aattcgtatt agttagcgtc   2220
gaggaaaga                                                            2229
```

<210> SEQ ID NO 9
<211> LENGTH: 7833
<212> TYPE: DNA
<213> ORGANISM: Artificial Sequence
<220> FEATURE:
<223> OTHER INFORMATION: chemically treated genomic DNA (Homo sapiens)

<400> SEQUENCE: 9

```
gtttttggtg agatatgtgt tttataagtt ttaatggaga aaaatgtaag tattttattt     60
tttgaaattt ggttatttga gtaatgagaa aatagttatt ttttttagga tagtggtttt    120
taattatggt tatgtgtttt tttaggaaaa ttttaaaaat atatatatat taatgttttt    180
gtgttatttt tagggatttt aagtttttga atacgaattt tgtattagta tttttttaatt   240
atttaggtga ttgtgatgtg aaattatgat tgagttttat tgttttaaga tgaaataaat    300
ttttttttagt attgaaatta taaatttaaa ttattaaaat taattaaggg tatgggaatt   360
aataaggtat agggaagttt ttatattata aaattatttt tttaaattat agtttattgt    420
ttatatgtta tttgttattg tagaaaaggg tgaaaaaata gtaaatttaa ttatttttag    480
tttgaaaaat tatttagaaa tgaagatgac gatttgaaa tattgttaat attatttgat     540
ttataaataa tgttttaata tatttattat atattgatag atattttttt atatgaatat    600
tatatattaa aattaaggta ataatgtatt tagaatattt tatttatatt tatgtatttt    660
aagtaggtta gaaattaaga tatgagttat taagtatgag atgttaaggt gtggggttag    720
aaattatatt gtattttatt attaataatt aatatatatt ttaatattat atatatttaa    780
ttttaatttg tatattttta attattttta attatgtgta taaatataag tatatatatt    840
tttatgtatt tatttattta tatttttatt tatttattta tataggggat tttttttaaat   900
ttattattat taaattatat atttttatttt taatttttag aataagttta ggaggtaggt   960
attgttatta tttatatttt ataaatgagg aaattgttta tagttataaa gttattgtgt   1020
tagatatatt agaagtttaa tatatatttg gtgaatatat gtataaaaat agagagatag   1080
atatgtataa tagtttattt ttatattgag taaaagtttt taatttgttt tagaaatttt   1140
tttgtgaaaa ttgagtaaaa atcgaggtat tttttttattt gttatatagg tatagtggt    1200
atttttattt tttaataagg atgaatattg aaatgtggat tttaaggttt aattttagat   1260
tttttgaatt tttgatagtg ggatttggaa tttgtttatt gttttaaagt tttttaagga    1320
atttatatga ttaattaggt ttagaaatta ttggatttta ttgtcgaagt ttgagaatta    1380
aagtttgggt tttattgcgg ttttatagaa agggtaaatg aagtattatg gatagaattg    1440
atacgttttt agttagtttt ttttttagaa agttaatagg tagtaatata gtagaaatta    1500
gtgatttatg ttttgtgttt tgaagttagg tagaatttta tagagtttta gtagtgttat    1560
```

```
tgacgagatt tgttttttgg ggtaagttgt ttgatgtttt taaagttata ttttttttat   1620

ataaaatgag ataatatttt ttgttttata ggggtgtttt aaagattaaa taaaaataat   1680

atgttttatt ttatatggta taatgtttga tatttaagaa gtaaaggata tattttattt   1740

ttattgaagt aattagaaag tatgaaatta tgaaggagat aagagttttg attggtagtg   1800

tattttattt ttttaggttt atttatttat tttaaattat ttttgttgga gaataatttt   1860

taagtttttt atttaagttg tgagtaattt tatattttat aatgatgttt tttttatgag   1920

aaaaaaaaat gtttttaagt tttttggaga aaatatattt gtattatttt tattgaaaaa   1980

tttaataatt ggattttgtt tttttgtatt aattttagag tgtatatgtt ataaataaag   2040

tgttttagtt taagaagatt gaaagtaaat atggtatagt attttaaaat aagaattttg   2100

taaatatatg gtatgattgt gttatattat tagtaattat atgatacgta atgtaaagta   2160

tagtttatag atttaaattt aattttaata agtaaattga ttttgttttg ttggggaaaa   2220

gttaaagtat taatttaatt gttaatgtag ttttgtttat ttttttggta tttagtgata   2280

agtttaaata atgtatatat ttttatttat atatttagta atataatttt ttgtttaatg   2340

agtgatgttt ttttgttatt tggtggtgtt tgttagtttt agaatttgtt ttttggtggt   2400

attataatat taagtataga gtaagtgtaa taaaattgta gtatttttat tgaaaaggtt   2460

ttgttttaaa ttgtttaata atttaaagga tttttgtgga agtaatcgta tttgttaatt   2520

agttataatt agtaattaat ttttttggag ttttaattta tttttggtaa aacgttttag   2580

gaagagtata tattattaga aagtatgtta aaaatttatt tagtagaaaa tttaaaaata   2640

gttttttttt gttaagaggt tttttaaaat tttatttata tagttaaatt ttgaaatttt   2700

agtaggtttt gttttattat tataattatt gtataaatat ttttaaggat tttgttttta   2760

gttttaagta tgatttattt ttataagttt gattagttat tatattagtt ttgttatgga   2820

aaatgatatg tttttatttt ttgttgtaga gttgttaaat tttgatttat atttatgttg   2880

tttttttgt tgaaagtttg tagcgaaaga aatttttaat tttttgtttt gtaatattag   2940

ttggtagttt tatttaatgg gtattttgtt tttttaaaga atttagttgt tttgtttaga   3000

agtcgatttt ttgatgtttt taacgtttgg tttaattgat ttgttttaat ggagttttcg   3060

tcggtgagga gcgagatgtt atcgattaga atgttgggat ttgttgttta attgttagga   3120

gtgagagata ttgagattta gaaatttttg gaggtgggag gggagaggga tagtttcgga   3180

cggaggcgga gatgtaagat aaagggatgg attttatata ggaaaaaaaa aaagatttcg   3240

ttgaggtatt gaggtgttgt acgattatat tttttaaagg agaagttaaa aagtaaggaa   3300

gtgggaggag gttggaggtt aaagtattta aaaggattat tcgggtataa tttgtttttt   3360

tgttggtgtt tgtaaaggat agatagtttc gtttttaaag tatatgaatg ttttttttaa   3420

gtgattggga atggatatta attgtttgtt aaatgttatt aaatgttttt ttaaatttag   3480

gggatataga aagaggggta taaaaggaga atttaaatag aaaaagggag gattcggagg   3540

tttttgaaag cgggggggaga agaaggagga gggataatag agaggaatag agaaggagag   3600

cggagagaag ataaataaaa ataaaaatag gaattattga ataattatat attaaaaaga   3660

aagttttttt ttatggggta tttaaaatat tgagattgta atagtgattt cggttatgga   3720

agaaagatgt ttttttttat ttttgttttc gaaagttttt ggtttcgtta ttggcgatta   3780

aaattttatt aggttaaaga gtgtgtttaa ttgtttgaag aatgtagtag acggaaggcg   3840

ggtttcgtta tgtcgtttgt ttttttcgtt ggagagaatg aaagaaacgc gtagagttag   3900

agatttttgt cgagttagat ttttttcgt cgttttaggt tatcggttat tcggtaaaga   3960
```

```
ttcgagtaag gaacgtaggg ttattgtttg ggttaataaa tggagttcgt ttttttttt    4020
tcggacgtcg ttgttcggtc gatgttttcg gtaatttatt cgcggcgtat gtagaggagt   4080
ttttttttt tttttagatt atttgtttcg attaatttga ttttttaaat atatttgatc    4140
gtatttttta ggtggatata ttaataggtt acgggttgga gaggagcggg tgatgaggag   4200
agggatttaa atttgcgaac gtttgggttg ggtcggagtt gcggggggtt tgggaggaga   4260
gaggggagaa gagagaagga aggagagcgt ttgtcgggat ggttgagttg tttcggcgag   4320
tagttttggg gttgtacgtt tttgtgggag atgttgttgt tgtttttagg tcggtaagag   4380
cggttttaat attatcgttt tttatttttt tttttgtaaa tttttagaga aacgtttttg   4440
gtttttttcgt cgcgatattt ttagtttgta ttttttttata gtttaggcgg cgcgtttcg   4500
tacgttggag cgtcggtcgt tagtaggacg ttttttttcg cgtcgattcg ttttttttg    4560
ttttgttgtt gttgtttttt tgatattttc gtttttatta tttttagttc ggagagacgt   4620
tatttagtcg cggttcgtat tcgcggttcg gggttacgcg cggaagaggg gcgttagttc   4680
ggatttcgtt ttcggtaggg ggcgttttgg agcggagagt gaggcgaatg gtatatgagt   4740
gtgcgggtag tttattttga agttcgagtt ttttatttga gttatgtttc gtttagtttt   4800
attcgggtta gcgtttggcg agcgagttta tttgtggttt tcgcggtcgt ttttttttg    4860
tatttttgta tttattcgtc gatttttttt tttcgggatt tgtattttgt tttattaatt   4920
agagttcgat tgtttttttt tacgtgattt cgggcgggtt gaggatttgt tgtttttttaa  4980
acgttagagg gatgcgggcg gtagagttcg agaggcggtt gtcgggttgc ggggcgtttt   5040
gatttttttt ttattttgtt ttttcgggtt ttattcgttt gtttttggat tttcgttttt   5100
ttttgttttt cggtttttta gagttttttt tttatggtag tagtttttcg cgttttcggc   5160
gtagtttttt agcggacgat tttttcgttt cggggttgag tttagttttt ggatgttgtt   5220
gaaattttcg agattatgcg cgggtttggt tgttgttttt tcgtcgggtg ttattgttat   5280
cgtcgtcgtt tttgttgtcg tcgttcgcgg gatgtttagt agttcgttgt tcggttttcg   5340
cgattttgtg tttttcggaa gtcgtttgtt gttgtagagt tgtacgaatt agttatggtg   5400
ttgtgggagt tttcgcggta gtgtagtagt tggatatttt gcgagggttt ttgttggttg   5460
ttgttgttgt tcgttatgtt atttatcgta gttcgttcgg tgaagttcgt tgtttttttt   5520
atttttttaa gtgattgtta aacgtttatc ggttggaatt gttttggtaa gtttagaatt   5580
ttcgttttcg atttttttaat ttcgtagaag aatacgcgta tttagtatag attagtttat  5640
tttagcgcgt tttttagtt ttttattttt tattgtttta gatttttaat attatttatt    5700
tttatttaga gaaataaggg gaattgttgt aggttcgggg gtgaggggtg gttttgggat   5760
gggtagaaag tgtaggtgta gtaggaaatt tttgtatgtt tgcgtttata ttggagttgc   5820
gaggattttg agaaatatta aacgggatgg tttttgggt ttattgtttt gaaagagtat    5880
taattttagg ggaaatattg aaatagaagt tttgttatta ttaaagaaaa aagttttatt   5940
aggatgagga agaaataatt ttatgagaaa gaatgagcga gaaagtaata aattaaatgg   6000
tgattgtagg ggaatcgttg atttttggta aaggtgttat gaggtcgtat tggtttttcg   6060
ttgaagatta ggttatatag attttagagg agttgggttt taatagaatt ttttttttt    6120
ttttttttt ttttttttt ttttttttt tttttttatt tatttatttt ttttttttt       6180
ttattttttt ttttttttagg cggtaaaaga tattggtttt gtagtttaga tatgtttttt  6240
tttttgtttt tttaagtttt aaggtagtat aggggagttg agaaaaagaa tattttgcgg   6300
gtttttttagg tcggagtggg tatgattgag gttggttagg ttttatgtag gcgagtcgag  6360
```

ggcggaatcg attttagtgg gcgttgattt ttttattttt ggataggttt ttgtggagtg 6420
ggttaggtat tttttttgtt cgttcgggtt tttttagatt ttgacggcga acgtttggta 6480
ggtttcgttt tgttgaagtt ttttaattaa atagggttag aggatgggag ttgttgtatt 6540
tttagttggt atagtattcg gtttgatagt ttgtagtata gggtgtatgt aatttttttat 6600 tttttgtgaa tataattttg ttgtagttaa atttggtttt gaataaagtg ttttttaaag 6660
atgtatataa gttgaagtgt atgtaatttt agagaggagg gaatgattaa ttgtaattta 6720
gggtgaaagt ttgtatagtt tttagttatt attgatgtaa atgttaaaag gaaaattatt 6780
atgtattatt tttaatttatt ttttataaag ataagttgag atatgtaatt ttattagatt 6840
tgggttaata gattgttttt tttttggta gtttttaaat ttggtatttt aataaaattt 6900
aatatgtttt tataattttt tgatttatgc gtatatgtgt gttgtttttg aaagaataag 6960
ttttattttg ttattgttta attatttttt agatgtttta ttatggtaat aattatgagt 7020
ttgtaaaaat aatttttgga aatgttgatg gttttgtagt ttaatataga ttggtttgtt 7080
ttatttttag tttttgtatt gttttaggaa ataattaatt taaatgtgaa gttgatattt 7140
gtaattaaga aattatatat ttattagata ttttaaaggg gattgtataa attaaagaga 7200
ataaattggt tttgtagata ggttgttaag aatttggtat ttcgttttta tttttgttaa 7260
tttagaggtg attaattttt atttgagtta aatagattat tatagaaaat attgtgtttg 7320
tttattttta ttattgaggt tttgtttttt ttttgtttgg atatatttta aataaggggt 7380
tgttttagtc gttgaagtaa aagaataatt aaagatgggg aaatggtaaa agggtattta 7440
gagattatta ttagtttttt tttaaaatgt ggagttttgt ggttataaat attgtttatt 7500
taatgagtaa aaaataaaaa taaaaaaaaa ataggaagta aatgttaagt ttttatttat 7560
tattgttagt attaacgtaa gttttaaaaa atagtattat tagaaaagga tattaaagga 7620
gaattgatta gaaaagaatt gtggaaaatg gaaacgaata ttgattattt aattagattt 7680
tgaggttatt agtagatagt gattttgtag tatagttata gttgttggat ttaaaattta 7740
ggataagtat tttaaagttt taaagtagtg ttttttttttg ttaaaaattt gtaagatgtt 7800
ttaatgattg gagtgttttt tttgaatttg agg 7833

<210> SEQ ID NO 10
<211> LENGTH: 7833
<212> TYPE: DNA
<213> ORGANISM: Artificial Sequence
<220> FEATURE:
<223> OTHER INFORMATION: chemically treated genomic DNA (Homo sapiens)

<400> SEQUENCE: 10
ttttaaattt aaagagaata ttttagttat taaaatattt tatagatttt taataaaaaa 60
aagtattatt ttgaagtttt aaaatatttg ttttaaattt taaatttaat aattatagtt 120
gtattgtaag gttattgttt attgataatt ttaaaattta gttaagtgat taatattcgt 180
ttttattttt tataattttt ttttagttaa tttttttttta gtattttttt ttgatagtgt 240
tattttttaa agtttgcgtt aatattgata gtggtgaatg aaagtttaat atttgttttt 300
tgtttttttt ttatttttat tttttgttta ttaggtggat aatatttatg attataaaat 360
tttatatttt ggaaaagagt tagtgatgat ttttgaatat ttttttatta ttttttttatt 420 tttaattgtt tttttgtttt aacgattgaa ataatttttt atttgaaatg tatttagata 480
aagaggaaat aaagttttaa taataaagat aaataggtat agtgtttttt gtgatggttt 540
gtttggttta aatgaagatt gattattttt aagttaatag gggtggaagc ggggtgttaa 600

-continued

```
gtttttgata atttatttgt aaaattagtt tatttttttt agtttatgta gttttttttta    660

aaatatttgg taaatatgta attttttgat tgtaaatgtt aattttatat ttaagttagt    720

tatttttttaa aataatgtaa gggttaggaa tgaagtaaat tagtttgtgt tggattataa    780

agttattaat atttttaaaa attgtttttg taggtttata attattatta taataaagta    840

tttaaaaagt gattaggtaa tagtaaagtg aaatttattt ttttaaaaat aatatatatg    900

tacgtatgaa ttaagaagtt atagaaatat gttgagtttt attaaaatgt taaatttaga    960

aattgttaaa aaagagaata atttattgat ttaaatttaa tagggttgta tattttaatt   1020

tgtttttgta aaggataaat tagaatgatg tataataatt tttttttgg tatttatatt   1080

agtaataatt aggaattata taggttttta ttttgagtta tagttggtta tttttttttt   1140

tttaaagtta tatatatttt agtttatata tatttttgaa agatatttta tttagagtta   1200

gatttaatta tagtaaaatt atatttatag aagatgaaaa attatatata ttttatatta   1260

taggttgtta aatcgaatgt tatgttagtt aggagtgtag taatttttat tttttggttt   1320

tatttaatta ggaagtttta gtagagcgaa gtttgttaag cgttcgtcgt tagaatttga   1380

aggaattcga gcgagtaaga agagtgtttg atttatttta tagaagtttg tttagaaatg   1440

gaggagttag cgtttattga agtcggtttc gttttcggtt cgtttatatg gagtttgatt   1500

agttttagtt atgtttattt cggtttggga gattcgtaaa gtgttttttt ttttaatttt   1560

tttgtattat tttgaagttt agggaagtaa agagaggggt atatttggat tgtaaaatta   1620

atgtttttg tcgtttagga gagaagggaa tgagagagag agagagatag atagatagag   1680

agagagagag agagagagag agagagagag agagagagag agaaatttta ttgaaattta   1740

gtttttttag aatttgtgtg atttggtttt taacgggaga ttagtgcgat tttatggtat   1800

ttttgttagg aattagcgat ttttttgtag ttattatttg atttattgtt ttttcgttta   1860

tttttttta taaagttatt ttttttttat tttagtaaga ttttttttt taatgatgat   1920

aaagtttttg ttttagtgtt ttttttagga ttggtgtttt tttaaaatag tgaatttaga   1980

aaattatttc gtttaatatt ttttaaaatt ttcgtagttt taatgtaagc gtaagtatgt   2040

aaaggttttt tgttatattt gtatttttg tttattttag aattattttt tattttcggg   2100

tttgtaatag ttttttttgt ttttttggat agaggtgggt ggtattaggg gtttagggta   2160

gtaggaggtg aggggttgag gaggcgcgtt agggtaggtt ggtttgtgtt ggatacgcgt   2220

gttttttttgc ggagttaaag ggtcggggac gggggttttg gatttattag agtaatttta   2280

gtcggtgggc gtttggtagt tatttaagga ggtagggaaa gtagcgagtt ttatcgggcg   2340

ggttacgatg agtagtatga cggggtagtag tagtagttag taaaagtttt cgtaaagtgt   2400

ttagttgttg tattgtcgcg gggattttta tagtattatg attagttcgt gtaattttgt   2460

agtagtaaac ggttttcgag gaatatagga tcgcgggggt cgggtagcgg gttattgagt   2520

atttcgcgga cggcggtagt agaggcggcg gcggtggtag tggtattcgg cggggaagta   2580

gtagttaaat tcgcgtatga tttcgagagt tttagtaata tttagggatt gggtttagtt   2640

tcggagcgag agggtcgttc gttgagaagt tgcgtcggag acgcgggaag ttgttgttat   2700

aaggagggag ttttgggaag tcggaggata ggaggagacg ggagtttagg ggtagacgag   2760

tggagttcga ggaggtaggg tggagggaga gttaaggcgt ttcgtagttc ggtagtcgtt   2820

tttcgagttt tgtcgttcgt atttttttgg cgtttgggaa gtagtaggtt tttagttcgt   2880

tcggggttac gtgggaagag gtagtcgggt tttgattggt ggagtaggat gtaggtttcg   2940

ggagggaggg gtcgacgagt aggtgtaagg atgtaaggag gaggcggtcg cggaagttat   3000
```

-continued

```
agatgggttc gttcgttagg cgttggttcg agtggggtta ggcggggtat ggtttaaatg   3060
agaagttcgg gttttagggt gggttattcg tatatttata tattattcgt tttatttttc   3120
gttttaggac gtttttatc gaaggcgggg ttcggattag cgttttttt tcgcgcgtga    3180
tttcgggtcg cgagtgcggg tcgcggttgg gtggcgtttt ttcgagttgg agatggtggg   3240
ggcggaggtg ttagaggagt agtagtagta gggtagagag gggcgagtcg gcgcgggaga   3300
gggcgttttg ttggcgatcg gcgttttagc gtgcgggagc gcgtcgttta ggttgtaggg   3360
ggatgtaggt tgggaatgtc gcggcggaga ggttagggac gtttttttag ggatttatag   3420
gaaagagggt gagaggcgat ggtgttagaa tcgtttttgt cgatttggaa gtaatagtag   3480
tatttttat aagagcgtgt aattttaagg ttgttcgtcg aggtagttta gttatttcgg    3540
taggcgtttt ttttttttt ttttttttt ttttttttt ttaggttttt cgtagtttcg     3600
atttagttta agcgttcgta ggtttgaatt ttttttta ttattcgttt tttttagtt      3660
cgtagtttat tagtgtgttt atttgggagg tgcggttaga tgtgtttgga aggttagatt   3720
ggtcgggata agtggtttga gagaaagaga aaggtttttt tgtatacgtc gcgggtgggt   3780
tgtcgggagt atcggtcggg tagcggcgtt cgggaagggg agagcgggtt ttatttgttg   3840
gtttaggtag tgattttgcg ttttttattc gggtttttgt cggatggtcg gtgatttggg   3900
gcgacgagag aaggtttaat tcggtaggag tttttggttt tgcgcgtttt ttttattttt   3960
tttagcggga agggtaaacg gtatagcggg attcgttttt cgtttgttgt atttttttagg  4020
tagttagata tattttttag tttaatggaa ttttagtcgt tagtaacggg attaagagtt   4080
ttcggggata agggtggaga ggaatatttt tttttatga tcggggttat tattgtagtt    4140
ttagtgtttt ggatgtttta tagggaagag ttttttttt ggtgtgtgat tatttagtga    4200
tttttgtttt tgtttttgtt tattttttt tcgtttttt tttttatttt tttttgttat     4260
ttttttttt ttttttttt tcgtttttaa aagttttcgg attttttttt tttttattta     4320
aattttttt ttgtgttttt tttttgtgt tttttgaatt taggagagta tttgataata     4380
tttaatatggt aattagtgtt tatttttaat tatttaaaag aggtatttat atattttgaa  4440
aacgggatta tttattttt gtagatatta gtagaaaaat aaattgtatt cgagtaattt    4500
ttttaagtat tttaatttt aattttttt tatttttttg ttttttaatt tttttttga      4560
gagatgtgat cgtgtagtat tttagtgttt taacgaaatt tttttttttt ttttgtgtga   4620
aatttatttt tttattttat attttcgttt tcgttcgaga ttgttttttt ttttttttat   4680
ttttaaagat ttttgaattt tagtgttttt tatttttggt aattaagtag tagattttag   4740
tattttagtc ggtggtattt cgtttttat cgacgaagat tttattaaaa tagattaatt    4800
agattagacg ttggaggtat tagaaaatcg gtttttagat agagtagtta aattttttaa   4860
ggaaatagaa tatttattag atagagttgt taattaatat tgtaaaataa ggaattagaa   4920
atttttttcg ttataggttt ttagtagaga aggtaatata aatatagatt aagatttaat   4980
aattttatag tagagaatga gaatatgtta tttttttatag taaggttggt gtggtaatta  5040
attaggttta tgaaaataag ttatgtttga aattaaaggt aaagttttta aaagtgttta   5100
tgtagtaatt atgataatga aataggattt gttaggattt tagagtttgg ttatgtaagt   5160
agaattttag agaatttttt agtagaggaa aattgttttt gaattttttg ttaagtaaat   5220
ttttggtata ttttttaata atatatgttt tttttaagac gttttgttaa aagtaagtta   5280
aaattttaaa ggagttaatt attggttgta attggttaat aaatgcggtt gtttttatag   5340
aggtttttta aattattaaa tagtttgaag taaagttttt ttaatgggaa tgttgtaatt   5400
```

```
ttgttgtatt tattttgtat ttagtgttat agtgttatta agaaataaat tttgaaattg   5460
gtaagtatta ttaagtggta gaagaatatt atttattgag tagagaattg tattattgaa   5520
tatgtaaata aaaatatata tattatttag atttgttatt aggtattaaa gaagtagata   5580
agattgtatt agtaattgga ttagtgtttt aatttttttt tagtaaggta aaattagttt   5640
atttattaga attaaattta agtttatgaa ttgtattttg tattgcgtat tatatgattg   5700
ttagtaatat gatataatta tattatgtat ttgtaaaatt tttattttaa aatattatat   5760
tatatttatt tttaattttt ttgagttaga atattttatt tgtggtatat atattttaga   5820
attgatgtag aggagtagag tttagttgtt agattttttta gtagaaatag tgtagatata   5880
tttttttttag aaaatttaag aatatttttt ttttttatgg aaagaatatt attataaagt   5940
gtgagattat ttatagttta agtagggggt ttgggagtta ttttttaata agaatagttt   6000
aagataaata aatgaatttg ggaaaataag atatattgtt aattagaatt tttatttttt   6060
ttatgatttt atatttttttg attgttttaa taaaggtaag atgtattttt tgttttttag   6120
gtgttaggta ttgtgttatg taggatagaa tatgttattt ttatttaatt tttaaaatat   6180
ttttatgaga taaagaatat tattttattt tatataaaag gaatatggtt ttgaaagtat   6240
taggtaattt gttttaagaa ataaatttcg ttagtgatat tgttgggatt ttgtgaaatt   6300
ttgtttgatt ttagagtata agatataagt tattaatttt tgttgtattg ttgtttgtta   6360
gtttttgaga ggggaaatta attgggaacg tattagtttt gtttatgata ttttatttgt   6420
tttttttgtg gagtcgtagt aaggtttaaa ttttaatttt taaatttcgg taataagatt   6480
tagtgatttt tgaatttggt tgattatatg aatttttttga gaaattttga aataatagat   6540
aaattttaag ttttattatt agggatttag aaaatttgga gttgggtttt gggatttata   6600
ttttaatatt tatttttgtt ggagaagtaa ggtattattt atatttatat gataaatgaa   6660
aggatatttc gatttttgtt tagtttttat agagaggttt ttgagatagg ttaaaagttt   6720
ttatttagtg taaagatgag ttgttgtata tgtttgtttt tttgttttta tgtatatgtt   6780
tattaaatat gtattaagtt tttaatatgt ttgatatagt aattttgtga ttgtagataa   6840
tttttttatt tgtaaaatgt gagtaataat aatatttgtt ttttgggttt gttttaaaga   6900
ttaaaataaa aatgtatggt ttaatggtag tggatttggg gggatttttt atataaataa   6960
gtgaatggag gtatgaataa ataaatatat aaagatgtgt gtatttatat ttatatatat   7020
aattaaaaat agttaaagat gtataaatta aagttaaatg tatgtgatat tgaagtatat   7080
gttgattatt gataatgaag tatagtataa tttttaattt tatattttaa tattttatat   7140
ttaataattt atattttaat ttttagttta tttaagatat atagatatag atagaatgtt   7200
ttaaatgtat tattgtttta gttttaatgt ataatattta tatgaaaaag tatttattag   7260
tgtgtagtaa atgtattaga atattattta taggttaaat gatattgata atgttttaga   7320
gtcgttattt ttatttttgg ataatttttt aaattgagag taattaaatt tgttattttt   7380
ttatttttttt ttataatggt aaataatata taaataatga gttgtgattt aaagaaataa   7440
ttttataatg taaaagtttt tttatgtttt attgattttt atgtttttaa ttaattttgg   7500
tagtttaagt ttgtgatttt agtgttgagg aaagtttatt ttattttaga gtagtggggt   7560
ttagttatga ttttatatta taattatttg gataattaaa gaatattgat gtagagttcg   7620
tatttaaaga tttggaattt ttagaagtga tatagaagta ttggtatata tatattttta   7680
aagttttttt ggagaaatat atagttatga ttgagaatta ttgttttggg gaaagtgatt   7740
atttttttat tatttaaata gttaagtttt aggaggtaaa atatttatat ttttttttat   7800
```

taaaatttgt aaaatatata ttttattaaa gat 7833

<210> SEQ ID NO 11
<211> LENGTH: 5666
<212> TYPE: DNA
<213> ORGANISM: Artificial Sequence
<220> FEATURE:
<223> OTHER INFORMATION: chemically treated genomic DNA (Homo sapiens)

<400> SEQUENCE: 11
aaaattagaa tttttatttt tttgcgtttg ttatattttt tagtgttgtt taattttttt 60
ttgtaagtga gggtggtgga gggtgtttat aattttttta gggagtaagt tttttttggt 120
tttttttttt tttttttttt tttttttttt tgagattaag tttcgttttt gtttttttagg 180 ttggagtgta atggcgcgat ttcggtttat tgtaatttc gtttttttttt gggtttaagc 240 gattttttta tattagtttt cgagtagttg ggattatagg tatgcgttat taagtttcgt 300
taattttgta ttttttagta gagatagggt ttcgttatgt tggttaggtt tgtttcgaat 360
ttttggtttt aggtgattcg tttgtttcgg tttttttagaa tgttgggatt atagacgtga 420
gttatcgtat tcggattttt tttttatgta atagtgataa ttttatttaa agtatttttt 480
tttttttttg agtcggagtt ttattttgtt atttaggttg gagggtggtg gcgcgatttc 540
ggtttattgt aatttttgtt tttcgggttt aagcgatttt tttgttttag tttttttgagt 600 agttggaatt atatacgtgc gttattatgg ttagttaatt tttgtatttt tagtagagac 660
ggggtgttat tattttggtt aagttggttt cgaatttttg attttaggtg atttgttcgt 720
ttcggttttt taaagtgttg ggattatagg tgtgagttat cgcgttttgt tttaaagtat 780 tttttttta tgttttaaaa taagattgta agttagtttt taaagcggat aatttaagag 840
ttaataggta ttagtttagg atgtgtggta ttgtttttaa ggtttatatg tattaatata 900
ttatttaaat ttataataat ttttataaag tagggggtat ttatattttt tttttttttt 960
ataattacga aaaatgtaag gtatttttag taggaaagag aaatgtgaga agtgtgaagg 1020
agataggata gtatttgaag ttggttttttg gattattgtg taattttgtt tttagaatat 1080
tgagtatttt ttttggttta ggaattatga ttttgagaat ggagttcgtt tttttaatga 1140
tttttttttt atttttttat ttgtttatag gtagaatttt ttttcgttcg tattaaataa 1200
attttatttt tttagagttt gtttttatat taggtaatgt atacgtttga gaaatttttg 1260
ttttagatag tcgttttata cgtaggaggg gaaggggagg ggaaggagag agtagttcga 1320 tttttttaaaa ggaatttttt gaattagggt ttttgattta gtgaatttcg cgtttttgaa 1380
aattaagggt tgaggggggta gggggatatt ttttagtcgt ataggtgatt tcgattttcg 1440
gtggggtttt tataattagg aaagaatagt tttgtttttt tttatgatta aaagaagaag 1500
ttatattttt tttatgatat taaatatttc gatttaattt ggtagttagg aaggttgtat 1560
cgcggaggaa ggaaacgggg cgggggcgga tttttttttta atagagtgaa cgtatttaaa 1620
tacgtttttg ttggtaggcg ggggagcgcg gttgggagta gggaggtcgg agggcggtgt 1680 gggggtagg tggggaggag tttagttttt tttttttgtt aacgttggtt ttggcgaggg 1740
ttgttttcgg ttggtgtttt cgggggagat ttaatttggg gcgattttag gggtgttata 1800
ttcgttaagt gttcggagtt aatagtattt ttttcgagta ttcgtttacg gcgttttttt 1860
gtttggaaag atatcgcggt tttttttagag gatttgaggg atagggtcgg agggggtttt 1920
ttcgttagta tcggaggaag aaagaggagg ggttggttgg ttattagagg gtggggcgga 1980
tcgcgtgcgt tcggcggttg cggagagggg gagagtaggt agcgggcggc ggggagtagt 2040

-continued

```
atggagtcgg cggcggggag tagtatggag ttttcggttg attggttggt tacggtcgcg   2100
gttcggggtc gggtagagga ggtgcgggcg ttgttggagg cgggggcgtt gtttaacgta   2160
tcgaatagtt acggtcggag gtcgatttag gtgggtagag ggtttgtagc gggagtaggg   2220
gatggcgggc gattttggag gacgaagttt gtaggggaat tggaattagg tagcgtttcg   2280
atttttcgga aaaaggggag gtttttttggg gagtttttag aaggggtttg taattataga   2340
ttttttttttg gcgacgtttt gggggtttgg gaagttaagg aagaggaatg aggagttacg   2400
cgcgtataga tttttcgaat gttgagaaga tttgaagggg ggaatatatt tgtattagat   2460
ggaagtatgt tttttattag atataaaatt tacgaacgtt tgggataaaa agggagtttt   2520
aaagaaatgt aagatgtgtt gggattattt agtttttaat ttatagatat ttggatggag   2580
tttatttttt ttattaggag ggattattag tggaaatttg tggtgtatgt tggaataaat   2640
atcgaatata aattttgatc gaaattattt agaagcggtc gggcgcggtg ttttacgttt   2700
tgtaattttt ttattttggg agattaaggc ggggggaatt atttgaggtc gggagttcga   2760
gattagtttg gttaataggt gaaatttcgt ttttattaaa aatataaaaa gtagtcgggg   2820
gtggtggtag gcgtttgtaa ttttagttat tcgggaggtt gaggtaggag aatcgtttga   2880
attcgggagg ttgaggttgt agtgaatagc gagatggagt tattttattt tagtttgggt   2940
gatagagtga gattttgtcg aaagaaagaa agagagaaag agagagagaa aaattattta   3000
gaagtaatta tatattgtgt ttatttttaa ttgagtaggg taaataaata tatgtttgtt   3060
gtaggaattt aggaaataat gagttatatt tatgtgatta ttttagaggt aatatgtagt   3120
tattattttg ggaatatttg ttaatatttt tgttttttta ttatttttag tttatttgat   3180
atagtttatt tgtgataaga gtttttaatt ttttattttt gaatagaggt gttttttttt   3240
tttttatttt tgttttgtga gggagttagg ggaggattta aaagtaatta atatatgggt   3300
aatttagtat ttttaaaatt ttgttaatag tttgaattcg ggagtttggt tttgtagttt   3360
tataatattt tagaagagat tttatttgtt taaaaataaa aaggaaaaag aaaagtggat   3420
agttttgata atttttaatg gagaagggag aagaatatgt agaaaagggg aaatgatgtt   3480
ggtttagaat tttaattata ttggtgttta atataggaat atttatttat ataatatttt   3540
aaagtattaa atttatatta gtatattatt aaatggatat attattaaat gggtttaagt   3600
attttatata ttttaattta attgatttat tttttttttg ttttggattt ttattatgat   3660
ttaaatattt atatatgggt tatttttttag atttttttata ttatgaaata taagaaaaat   3720
ttttaaggtt agttttatga ttaagacgaa ggattttatt gaatatataa aataataaat   3780
atattgtaat attttgtttt tttttttgta gttgtaattt ggtttgttta tatttttttt   3840
ttgttttttt gaaaattgag ttagttttat ttttttagga taggatttaa taattataat   3900
ataatttagt ataatttttt gatttaggta aattatgtaa tttgtgttta gtatgaaatg   3960
tatttaaaaa taagtaattt tttttaata ttattatttt taaattaata taataaataa   4020
tagttatttt aaaataaatt gtttattttt attatgtagt atttaaattt taaggttgtt   4080
atgattgtag atagtatttt aaaatttttt tttggaaatg gttttgtttt taagatgatt   4140
taggaattaa agaggtgatt attttttgtt taatgaattt ttaaattata aatttgggaa   4200
gtgttttagt tttttattgt tgttgttata aattattata aatgtgttag ttaaaataaa   4260
tataaaatta ttattttata gttttagaga ttagaagtta aaaatgggtt tataaggttt   4320
tatttttttt ggaaatttta aggggtaatt tgttttttttg ttttttttag tttttagtga   4380
ttattaaatt ttttggttta tggtttttgt attttttttg tggtttgtgt ttttattttt   4440
```

```
gtattttttt tttgattgtg atttttttaat aaaaatattt ggggttatgt tgggtttatt   4500
ttgaaaattt tggataattt tttttaagat tattaattaa attatatttg taaagttttt   4560
tttgttatat aagttaatgt attaaaagtt tttgaggatt aggatataga tattgggggt   4620
gggggggtat tatttagttt attataggaa ggaattttag ggttaattaa attagttttt   4680
ttattttata tttgaagaaa ttgaagtttt ggaattggag agtattatgt taaatgaaat   4740
aagttaaata tagaaagata aatattatat gtttttattt atttgtgaaa tataaaataa   4800
ttatattttt agtagtaaag agtagaatgg tggttattag agttgggggg tgggaggaat   4860
ggggagatgg taattaagat ataaagtttt agttaagatg ggaggaataa gtttgattgt   4920
tttttttgag atgtgtttta tagtatgatg aatatagtta aatagtaaat tttaaatgtt   4980
tttatttgat aaaaatgtta aatatttgag atgatggata ggttatttag tttgatttaa   5040
taatttttta ttgtgtttaa agattataat tttatattgt attatataaa tatatataat   5100
tgtattattt taatatataa ttttaaaatt aatataatga aaaagaaatt gaagtttaat   5160
atttttagaa gttaagtgta atttaaaagt tttgtgagaa tttgttttaa taaataaata   5220
agttttttttt ttttaataat tattatattt tgcgtttgga tatatagtag tgaataaaaa   5280
aaaaaaaaaa aaaaaaaatt tttaggttta atataatttt aggaagaaat tttagtagtt   5340
gtattttagg ggaaatatag gaagttagtt tggagtaaaa gttagtttgt ttttgttttt   5400
ttgttatttt gttcgtgttt tatagtgttt tttgtttgtg acgatagttt cgtagaagtt   5460
cggaggatat aatggaattt attgtgtatt gaagaatgga tagagaattt aagaaggaaa   5520
ttggaaattg gaagtaaatg taggggtaat tagatatttg gggtttgtgt gggggtttgt   5580
ttggcggtga gggggtttta tataagtttt tttttcgtta tgtcggtttt tattttggtt   5640
ttgattattt tgttttttttt ggtagg                                        5666
```

```
<210> SEQ ID NO 12
<211> LENGTH: 5666
<212> TYPE: DNA
<213> ORGANISM: Artificial Sequence
<220> FEATURE:
<223> OTHER INFORMATION: chemically treated genomic DNA (Homo sapiens)

<400> SEQUENCE: 12
```

```
tttgttagag agaatagaat ggttagagtt agggtggggg tcggtatgac ggaaaggaag     60
tttgtgtaga gttttttttat cgttaagtag atttttatat aagttttagg tgtttaatta    120
tttttatatt tgtttttagt ttttaatttt tttttgagt tttttattta tttttttagta    180
tataatgaat tttattatat ttttcgaatt tttgcggagt tgtcgttata ggtagagagt    240
attgtgaggt acgggtaaaa tagtaaaggg gtagggatag attgattttt attttaggtt    300
aatttttttgt attttttttg agatataatt attgaaattt tttttttgaaa ttatgttagg    360
tttggagatt tttttttttt tttttttttt tgtttattgt tgtatattta agcgtagaat    420
gtggtaattg ttaaaaagag aaaatttgtt tgtttgttaa aataaatttt tataaaattt    480
ttaagttata tttagttttt gggaatgttg aattttaatt tttttttttat tatattagtt    540
ttaaaattat atattgggat agtatagttg tatatattta tgtggtataa tatgaagtta    600
tgatttttga atataatggg gaattattaa gttaagttaa gtaatttatt tattatttta    660
aatatttgat atttttgtta aatgagagta tttgggattt attatttagt tatatttatt    720
atgttatgaa atatatttta aaaaaaataa ttaaatttat tttttttatt ttaattgagg    780
ttttatattt tgattattat tttttattt tttttatttt ttagttttag taattattat    840
```

```
tttatttttt attgttaaga atgtaattgt tttatatttt atagataagt gagaatatgt    900
gatatttgtt tttttgtgtt tggtttattt tatttagtat aatgtttttt aattttaaaa    960
ttttaatttt tttaagtata aaataagaag gttagtttaa ttaattttaa aatttttttt   1020
tgtggtaggt tgaataatgt ttttttattt ttaatgttta tgttttaatt tttaaaaatt   1080
tttaatatat taatttatgt ggtaaaagag gttttgtaga tgtgatttaa ttaatggttt   1140
tgagggagat tatttagaat ttttagggtg ggtttaatat aattttaagt gtttttatta   1200
gagggttata gttagagaga agatataaga atggaagtat aggttataga gaaaatatag   1260
agattatgag ttaaggaatt tgatggttat tagaagttgg aaaagataag gaaatagatt   1320
gtttttttaga gtttttaaaa ggaatgaaat tttgtggatt tatttttgat ttttgatttt   1380
tagaattgta aaataataat tttgtgtttg ttttagttaa tatatttgtg ataatttgta   1440
atagtagtag taggaaatta aaatattttt taggtttatg atttgagagt ttattaaata   1500
agagatggtt attttttttgg tttttaaatt attttggaaa taaagttatt tttagagagg   1560
aattttaaaa tattgtttgt agttatagta attttaaaat ttgagtgttg tatggtggaa   1620
gtagataatt tattttagga taattgttat ttgttatatt agtttgagga tggtggtgtt   1680
aaagaggagt tatttatttt taggtatatt ttatattaaa tataaattgt ataatttgtt   1740
taaattaagg aattatatta aattatatta tggttattaa attttgtttt gagaaagtga   1800
aattgattta gtttttaaag agataaagag aaagtataag taaattaaat tgtagttata   1860
aaaagaaaga taaaatgttg tagtatattt attgttttgt gtatttaatg aagtttttcg   1920
ttttggttat aaaattagtt ttaaaggttt tttttatatt ttatagtatg aaaaatttaa   1980
aaagtaattt atatgtaaat atttaaatta tgatagaaat ttaaagtaaa aagaaaatga   2040
attaattgaa ttaaaatgtg taggatgttt aaatttattt gataatatat ttatttgata   2100
atatattaat atgaatttag tattttaaaa tgttatataa ataaatgttt ttatattaaa   2160
tattaatgta gttaggattt taagttaata ttattttttt ttttttatat gttttttttt   2220
ttttttttatt aaaaattgtt aaaattattt attttttttt ttttttttttg tttttaaata   2280
aataaggttt tttttaagat attgtaggat tataaagtta aattttcggg tttaagttgt   2340
tggtaaaatt ttagagatgt taagttattt atgtattaat tatttttaaa ttttttttta   2400
atttttttat aaaataggag tagggagagg agaaatattt ttgtttaaaa atgaggaatt   2460
gaaaattttt attataaata aattatatta agtaagttaa agatagtaaa agagtaaaaa   2520
tgttagtaga tatttttaaa atggtaatta tatattattt ttggaatgat tatatgaatg   2580
tggtttatta ttttttaagt ttttatagta aatatatatt tatttgtttt atttagttaa   2640
aaataaatat aatatgtagt tgtttttgaa taattttttt ttttttttttt tttttttttt   2700
ttttttcgat aaagttttat tttgttattt aggttggagt gaagtggttt tatttcgttg   2760
tttattataa ttttagtttt tcgggtttaa gcgatttttt tgttttaatt tttcgagtag   2820
ttgggattat aggcgtttgt tattattttc ggttattttt tgtattttta gtagaggcga   2880
ggttttattt gttggttagg ttggtttcga attttcgatt ttaggtgatt tttttcgttt   2940
tgatttttta aagtgaaggg attataaggc gtgaggtatc gcgttcggtc gtttttgaat   3000
aatttcgatt aaaatttata ttcgatattt attttaatat atattataga tttttattga   3060
taattttttt tagtaagaaa gataagtttt atttaggtat ttgtgaattg gaggttaagt   3120
agttttagta tattttatat tttttaaga tttttttttt attttaaacg ttcgtaaatt   3180
ttgtatttga taaagagtat atttttattt aatataaata tgtttttttt tttagatttt   3240
```

```
tttagtattc gagagatttg tacgcgcgtg gtttttttatt tttttttttt ggttttttaa   3300

gtttttaggg cgtcgttagg aggaggtttg tgattataaa ttttttttga aaatttttta   3360

ggaagttttt tttttttcg gagaatcgaa gcgttatttg attttaattt ttttgtaaat   3420

ttcgtttttt agagtcgttc gttatttttt gttttcgttg tagatttttt atttatttgg   3480

atcggttttc gatcgtaatt attcggtgcg ttgggtagcg ttttcgtttt tagtagcgtt   3540

cgtatttttt ttattcgatt tcgggtcgcg gtcgtggtta gttagttagt cgaaggtttt   3600

atgttgtttt tcgtcgtcgg ttttatgttg tttttcgtcg ttcgttgttt gttttttttt   3660

ttttcgtagt cgtcgagcgt acgcggttcg ttttattttt tggtgattag ttagtttttt   3720

tttttttttt tttcggtgtt ggcggaagag ttttttttcga ttttgttttt taaatttttt   3780

ggagggatcg cggtattttt ttaggtaagg ggacgtcgtg agcgagtgtt cggaggaggt   3840

gttattaatt tcgagtattt agcgaatgtg gtatttttga agtcgtttta ggttgggttt   3900

ttttcggggg tattagtcgg aagtagtttt cgttagagtt agcgttggta aggaaggagg   3960

attgggtttt tttttatttg tttttttatat cgtttttcgg tttttttgtt tttagtcgcg   4020

tttttttcgtt tgttagtaaa ggcgtgtttg agtgcgttta ttttgttaaa aagaaattcg   4080

ttttcgtttc gttttttttt ttcgcgatat aattttttta attgttaaat tgaatcgggg   4140

tgtttggtgt tatagggaaa gtatggtttt tttttttaat tataagaaaa agtaaaatta   4200

ttttttttta gttgtgagag ttttatcgag aatcgaaatt atttgtacga ttagaaagtg   4260

tttttttatt tttttaattt ttgattttta ggagcgcggg gtttattaag ttagaaattt   4320

tagtttaaag gatttttttt ggagagtcgg attgtttttt tttttttttt tttttttttt   4380

tttgcgtgta aaacggttgt ttggggtaag ggtttttttag acgtgtatat tgtttggtat   4440

aagagtagat tttgaaaaga tgaggtttat ttaatacgga cgggggagaa ttttgtttgt   4500

aggtagatag gaaaatgggg agggagttat tggaaggacg gattttattt ttaaagttat   4560

aatttttaga ttagaaaaag tgtttagtgt tttagaagta gagttgtata gtgatttaaa   4620

gattagtttt aaatattgtt ttgttttttt tatatttttt atattttttt tttttattga   4680

aaatattttg tatttttcgt aattataaag ggggaaggga atatgagtgt tttttgtttt   4740

ataggggttg ttgtgagttt aaatgatgta ttaatatata taagttttaa gaatagtgtt   4800

atatatttta agttaatatt tgttagtttt tgaattattc gttttgagga ttggtttgta   4860

attttgtttt gaggtataga aagaaaatgt tttggagtag gacgcggtgg tttatatttg   4920

taattttagt attttgggaa gtcgaggcgg gtagattatt tgaggttagg agttcgaggt   4980

tagtttggtt aaaatggtga tatttcgttt ttattaaaaa tataaaaatt agttggttat   5040

ggtggcgtac gtgtgtaatt ttagttattt aggaggttga ggtaggagaa tcgtttgaat   5100

tcgggaggta gaggttgtag taagtcgaga tcgcgttatt atttttttagt ttgggtgata   5160

gaatgagatt tcgatttaaa aaaaaaaaaa aatgttttgg atagaattat tattattata   5220

taaaaggaaa gttcggatgc ggtggtttac gtttataatt ttagtatttt gggaggtcga   5280

gataggcgga ttatttgagg ttaggagttc gagataagtt tgattaatat ggcgaaattt   5340

tgtttttatt aaaaaatata aaattagcgg ggtttggtgg cgtatgtttg taattttagt   5400

tattcggagg ttgatgtagg agaatcgttt gaatttagga gaaggcggag gttgtagtga   5460

gtcgagatcg cgttattgta ttttagtttg ggagataaga gcgaaatttg gttttaagaa   5520

aaaaagaaag aaagaaagaa agaaagatta agaagaattt attttttgaa aagattatgg   5580

gtattttttta ttatttttat ttataaagaa aagttaaata gtattaaaga gtataataag   5640
```

cgtaaggagg taaaagtttt aatttt 5666

<210> SEQ ID NO 13
<211> LENGTH: 2470
<212> TYPE: DNA
<213> ORGANISM: Artificial Sequence
<220> FEATURE:
<223> OTHER INFORMATION: chemically treated genomic DNA (Homo sapiens)

<400> SEQUENCE: 13
aaagatgatt aaaagtttaa ttgtttattt gaagagttga tttttttatt tttgtaataa 60
agggtatttt tagtagtttt tgtttatttt gtttatttgg tttttttttgt ggttgtgtaa 120 ggttataatt tttgtgtttt agtaaatttg tgtatgttta tttttttttt tgttattatt 180
ttttttttta ttttgtttta ttattttgat gtaaaattat ttgttaattt tatttgaaat 240
gagaaatttt aaggtttata ttatttaaat tttgttagat ttttattttt gttatatggt 300
ttataatgtg ttgggtattt ttagatttgt ttattaaaaa gatgtaaaat aaaataatga 360
ttatttttgt ggattttttt tttatttttg agatgttttt tttggttgta ttattttttt 420
atttttgttt tattgattag aggaggggtt ttaattatgg gtgaatttta tattttattg 480
aagaggttat gttatatgta tatttttata atataattta tatttatata gtatttttat 540
ttttagtata ttttttttta ttaattttaa taatattatt gtaagttatg ttgaagtaga 600
ttgtaagtgt ttatttataa attgtgaaat gaattaaaat gaaagggtaa agattaaatt 660
atgattaggt ttgaaattaa tatataagat ttaatttttt ttaattaaag atttttgtag 720
gtgatttttg tttgtaggat tttttttttt ttttagatgt tattggattg tattaggttt 780
attgtagatt ttagttgttg tagaattaat tagatttaag atgagttttt tgattttttt 840
tggtagagtt ttttaattgt tgaattttaa tattgttgtg attagttagt gttataattt 900
gtttgtttta ttttgtgtaa tggattttat attatagagg tatttttttta atgttaagat 960 gtttaagtat tgtttaagtg taaattattt aatatttttt agttattaag taattaagat 1020
aggtaggatt ttatttgttt taaaatgatt tgatttaaat taaaaagaga atgtggattt 1080
tttgaatttt atttggttaa ttttaatata atttttagta ttttataatt ttttttaaag 1140 ttttttttatt tggttatttt ttgtattttt tttgtttttt tttttttttt ttagttataa 1200
taattgttag attttgtttt attttttttt gatagttttt atttttaagg ttatttattt 1260
tttttaggta ttttttggtt ttagtttgag tatagtagat tttaagatta tatatgttat 1320
agtataggtt attatagtta attttttgaa taaatgtgat tgaattttat gttagtaatt 1380
tttatttatt atttttttat taaaaaggtt taaagttttt atttaatgtt ttttttttatg 1440 tttattttgt taaatgattg ttttttaatg atattttaga atttttagaat tattttatta 1500 tggaggatgt gtaagattag ttttttatta aataaaaagt gtgaaatgga atatgtaatt 1560
ttattaattt attttggttt taaaattttg tgattattag ataaaattta gaaataaaat 1620
agtattatta atataaataa atttttatta taattatatt ttttaagttt tgtttgtaag 1680
aatgggtaaa atatttttaa aattttgaag aaattattat ttgatagaaa gtttaattta 1740
tttgtgagaa ggtaaatgta tttagatata attaaagttt ttttttttat tttaatttta 1800
tttattttga attaagattt tattgtttta ttttttttaga tgttgttatt tgaataatat 1860
tgttttgaga ttaaaaatta gtatattaat ataatttttt ttaaatgttt taagagtttt 1920 gttttttttta ttttttttttt taaaaataag tagttattaa attttttagt agtgaatttt 1980
aaaatttttt ttaattttat aggtttaagg gtagttaagg atggttgtag ttttatatga 2040

```
ttagttgtta aagtaagttg aggtattgaa gatggagaat ttaaattttt gataagagtt   2100
agaagataat tttaattatt ttataaaatt ggaaattgag gtatttaata tgaaggtatt   2160
aagattgtga tttttaattg tagtttattt atttttattt agtatttttt tttgtaaatt   2220
tgaggtaaga tattttattt aaaagtgtat tttaaattaa gtaataatat gtaaattttt   2280
ttttgtaaaa gttagtattt atatttttaa ataagatata ttgaatttat ttagtgaatt   2340
atataaagaa aataagtgta aaattttaat ggttagttag tttttagttt tttttaagat   2400
taaagagaag agattaaata tagtattatt gtattgaggt aaggtttttt gtgtagttta   2460
tagaaattag                                                          2470
```

<210> SEQ ID NO 14
<211> LENGTH: 2470
<212> TYPE: DNA
<213> ORGANISM: Artificial Sequence
<220> FEATURE:
<223> OTHER INFORMATION: chemically treated genomic DNA (Homo sapiens)

<400> SEQUENCE: 14

```
ttagttttta tgaattatat agaaaatttt gttttagtat agtgatgtta tatttggttt     60
ttttttttta attttaaaaa gaattaagaa ttaattagtt attggagttt tatatttatt    120
tttttatat gatttattga atgaatttaa tatattttat ttaaaaatat aaatgttaat    180
ttttgtaaga aagagtttat atattattgt ttaatttaaa atatattttt aagtaaagtg    240
ttttatttta agtttataag agggaatatt gaataaaaat ggataaatta taattaaaag    300
ttatagtttt gatattttta tattagatgt tttagttttt agttttgtaa gatgattgga    360
attatttttt agtttttgtt gaagatttga gtttttttatt tttagtgttt taatttgttt    420
taataattga ttatatgaag ttgtagttat ttttggttat ttttggattt ataaggttaa    480
aaaggatttt gaaatttatt attaaaaaat ttagtggttg tttgtttttta aagaaagggg    540
taaaggaaat aaaattttta agatgtttaa gaagaattgt gttaatatgt tagtttttgg    600
ttttaaaata atattgttta agtagtagta tttaagagga tgaaatagtg gagttttagt    660
ttaagataaa tgaaattaaa atagaagaga gaattttagt tgtgtttgaa tatatttgtt    720
tttttataga tggattaaat tttttattaa gtaataattt ttttaaggtt ttaaagatat    780
tttatttatt ttttataggta aaatttagga aatataatta tgataaaaat ttatttatat    840
tagtaatatt attttatttt tgaattttat ttgatagtta tagaatttta gagttagaat    900
ggattaatga gattatatat tttattttat atttttattt tgataaaagg ttaattttat    960
atattttttta tggtgaaata gttttgaagt tttaagatgt tattaaaagg taattattta   1020
ataaaatgga tatgaaggag agtattaaat gaagatttta agttttttttg ataggaagat   1080
ggtaaataag aattattaat ataaagttta attatattta tttaaaaggt tgattataat   1140
agtttatgtt atggtatatg tggttttggg atttgttgtg tttaaattga ggttaaaaga   1200
tatttaaaga gaatggatga ttttaggagt agagattgtt aaagagaaat gaagtagagt   1260
ttggtagtta ttatgattgg gaaagaagag gagagataaa gaagatataa aagatagtta   1320
ggtaagagga ttttaggaag aattatagaa tgttaggagt tatattaaga ttaattaagt   1380
aagatttagg agatttatat ttttttttta gtttaggtta aattattttg gaataaataa   1440
aattttgttt attttaatta tttaatagtt aaaaagtatt aagtagtttg tatttaagta   1500
atatttaaat attttgatat taaaaaaatg tttttgtaat atgaaattta ttatataaaa   1560
taaggtagat aggttgtaat attggttagt tatgataata ttggagttta gtaattggaa   1620
```

```
gattttatta aaggaaatta ggggatttat tttagattta gttagtttta taatggttag   1680

aatttatagt aaatttggta taatttaatg atatttgagg aggaagggga gttttgtagg   1740

tagggattat ttataaaagt ttttggttga aaaaaattga gttttgtgtg ttaattttag   1800

gtttggttat gatttaattt ttgttttttt attttaattt attttataat ttgtaaatga   1860

atatttataa tttgttttaa tataatttat agtgatatta ttaggattaa taaaaaaagg   1920

tatgttaaaa ataaaagtat tatgtaaatg taagttatat tatgaaaata tatatgtaat   1980

ataatttttt tagtaagata tagggtttat ttatagttaa gatttttttt ttgattaatg   2040

ggtaaggggt gaagaagtaa tgtagttaaa ggagatattt taaaaataaa ggaaaaattt   2100

ataggagtga ttattatttt gttttatatt tttttaataa gtaggtttga aaatatttag   2160

tatattataa attatatgat agaggtaggg atttgataga atttgaataa tgtgaatttt   2220

aaaatttttt attttaaata aaattaatag gtaattttat attaaaataa taaaataaaa   2280

taagagaaaa ggtagtaata gagaaaaaaa tgggtatgta taagtttatt gagatataga   2340

agttataatt ttatataatt ataaaaagag ttggatgggt aagatgagta gagattgtta   2400

aaagtatttt ttattatagg aataaaaaaa ttaatttttt agatgaataa ttaaattttt   2460

aattattttt                                                          2470
```

<210> SEQ ID NO 15
<211> LENGTH: 2229
<212> TYPE: DNA
<213> ORGANISM: Artificial Sequence
<220> FEATURE:
<223> OTHER INFORMATION: chemically treated genomic DNA (Homo sapiens)

<400> SEQUENCE: 15

```
ttttttttttg gtgttggttg gtgtgggttg gggttaggtg gagaagttgt tttttgttaa     60

ggtgatagaa tgtgttgggg gtgggggttg gggttagggt tggtgtaatt agggggttgt    120

tgtttttttt tggatatagt ggaagttttt tttgtattat taaatttttg ttattttttt    180

tgagggattt gtttttaggt agtatgtaag ttgttgtttt gggtttattt tgtatttttt    240

tattgggtga ggaaggagta ttttgaatgg agatgggggt gtttttggtt tatatatttg    300

tagagaagag gtgtgttggg ttgtattttt ggaggttgtg gtaattgata ttagagaaga    360

ttttggttgt agttgggaag gtttattggt tggaaagagg tgtttttttt ttttagtaaa    420

gggttttgtt tggaagggtt gttttttatt tgtttagtgg tattatagga tggttggttt    480

ttatttgaat ttttttggat ggtattatta tatagttggg tttttgtagt gttggttttt    540

taatttgatg attgttattt tggtgaggat ttgtgttgat ggttggagaa ttttgtgttg    600

tgggtgtata tggttaggtg gtgtttggta ggtgatgttt gggtgtagga tggtgttttt    660

attgttttat tttaaattgt tgtttgggtt taggtttttt ggttttttga atagggggttt    720

ggggggttaa ggatgttgag gttttggggg taggaagttt tttttggtta agtgtttttt    780

ttttttttttg gtatatattt ttttatttat ttattttgtt tatttttggg gtgagaggtt    840

tattaaggta gggtgtgttt tttttatgaa ttattttaag gtttttgagt tgtgggggtt    900

ttgggtaatt attttttttt ttttttggtt ttaggtattt tagtttaggg gtttgtagag    960

aagtttgaag tttggataaa tgtgttggat gttaataatt ttttattttt ggtagtagta   1020

aaggttaata tatttttatt ttttatttta gtttgttatt aaaataaagt tgtgtgtggt   1080

tgagggtagg aaggtgttga gattgagaag aagggatgtt ttggagaaag tgtgtttagt   1140

tgattttaga aattagagtt ttttgggatt ttgttgagat tttttgtagg gtgttttaat   1200
```

ttgttttttt attgtgtgtt ggtgttgtag tgtgtgtggt ttagggtttg gtgattttgg 1260
tttagtttgg tggttgtggt gaggtttttg gtgtagttgt ttggaatttt gtattagaat 1320
tgggattgtg taaatgtttt ggttgaagtg ttattttatt taagaaatat tgttgttagg 1380
aataaaatgg ggtttttggt gttttgaagt attttttgaa attttttttaa aataatttat 1440 aaaaaatgtt tttgttttaa tgttttataa tgtttaagga aatatgtaaa tggtttgttt 1500
ttttattgag atggttgttt taattaatag tgtatatata tataataatt tttttaattt 1560
ttttttttag agttaagtat tttattatat gtaaattata ataaagaaaa gattgtgtaa 1620
gattatgtaa gttgattgat ttaaaatatt gagttttaat ttaggttttt tgttttttta 1680
tttaataatt tttgtgtttg gattagattg gtgaagtagg ttatggaaat taataaagta 1740
aaaaattaaa agtatttttt tttgttattt ttttttttaa aattaaataa tagttgtttt 1800
tttttgagta ggttttagtt ttaggtttga gtttttttgt gattatttta tagttattta 1860
tagtagttgt tgttgttttt gttgggtttt tgtttttgtt ttttttgggt tgttttttgt 1920
atataaaata tattttagtt ttttaattaa atttaaatat gattttggta gaatttatat 1980
attttgtggt gtatggattg tgttggtgta ggggaaataa atattttttg gtatttaatt 2040
attgagttta atttgaaaaa ttgggattgg gtttttaggt ggtattttag gggttttaat 2100
ttggtttgtg tttttttaga ttttggtgtt gagagtgttg tttttgtggg tgggtggatg 2160
gagaggtaat aatttgtttt taataaaaat ttgttgttat tgaattgaaa gtgaaaggga 2220
agggagaag 2229

<210> SEQ ID NO 16
<211> LENGTH: 2229
<212> TYPE: DNA
<213> ORGANISM: Artificial Sequence
<220> FEATURE:
<223> OTHER INFORMATION: chemically treated genomic DNA (Homo sapiens)

<400> SEQUENCE: 16 ttttttttt tttttttgtt tttgatttgg tggtgatagg tttttgttga aagtagattg 60
ttattttttt gtttatttat ttgtaaaagt agtgttttta gtgttaaggt ttggggaggt 120
gtgggttagg ttggagtttt tggggtgttg tttaggggtt tagttttgat tttttgaatt 180
agatttagtg gttaaatatt agagggtatt tatttttttt gtattgatat aatttatgta 240
ttatgaaatg tgtaaatttt gttggggttg tatttgaatt tagttagaga attggggtgt 300
gttttgtata taagagatga tttaaagaag gtagaaatga aaatttgata gaagtagtaa 360
tagttgttgt gggtgattgt ggggtgattg taggaaaatt tgagtttggg attgaagttt 420
gtttaggaag gggtgattgt tgtttaattt tggagggagg gatggtgaag gaagatgttt 480
ttaatttttt attttgttaa tttttatagt ttgttttatt agtttggttt aaatataaaa 540
gttgttaaat agaaaaatag agggtttgga ttaaaattta atattttaag ttaattgatt 600
tgtatgattt tgtataattt tttttttatt ataatttata tatagtgaag tgtttagttt 660
tgaggaggaa agttggaaga attgttatgt atgtgtatat tgttagttag gatgattatt 720
ttgataaaga aatagattat ttatatgttt ttttaaatgt tgtaaaatgt taaagtaaaa 780
atattttttg taagttgttt taagaaaatt ttagaagata ttttggagta ttggggattt 840
tattttgttt ttgatagtag tgttttttga atagggtgat attttagtta gggtatttgt 900
gtggttttga ttttaatgtg aagttttaag tggttgtgtt aggaattttg ttgtgattgt 960
tgggttaagt tggagttatt aagttttgag ttgtatgtgt tgtgatgttg gtatgtagta 1020

```
ggaaaataga ttaaaatgtt ttatagaaaa ttttggtgaa gttttggagg attttggttt   1080

ttaagattag ttgggtgtat tttttttggg atgttttttt tttttggttt tagtgttttt   1140

ttgtttttag ttgtgtgtag ttttgttttg gtggtaaatt gaaataagaa atggaaatat   1200

attggttttt gttgttgtta gggatgagag gttgttgatg tttggtgtgt ttgtttgggt   1260

tttgggtttt tttgtagatt tttggattgg ggtgtttgag gttaggagag gagggggata   1320

gttgtttgga gtttttgtgg tttagaggtt ttgggatgat ttatgggggg ggtgtgtttt   1380

gttttggtga gttttttgtt ttgagggtag gtgaggtggg tgggtagggg agtgtatgtt   1440

ggagagaaga gagaatgttt aattagagag aattttttgt ttttggagtt ttagtgtttt   1500

tagtttttta aatttttgtt taggaagttg aaggatttag gtttaggtaa tggtttgggg   1560

tggggtggta agagtgttgt tttgtatttg gatgttgttt gttaggtgtt atttggttat   1620

gtgtgtttgt agtgtagggt tttttggtta ttagtatagg tttttattga ggtgatagtt   1680

attggattgg gaaattaata ttgtgaggat ttggttatgt gatgatattg tttgggggaa   1740

tttgagtgga agttgattgt tttgtggtgt tattagatag gtgagaagta gtttttttaa   1800

atagggtttt ttgttggaag gaggaggtat tttttttag ttagtgagtt tttttagttg   1860

taattggggt tttttttaat attagttatt gtggttttta gaggtgtagt ttggtatatt   1920

ttttttttgt agatgtataa attggggata tttttatttt tatttaagat gttttttttt   1980

tatttagtag aggggtgtgg agtaaatttg ggataataat ttgtgtgttg tttggaagta   2040

ggttttttag aaaggatgat aaaaatttgg tgatgtggaa gaagttttta ttgtgtttag   2100

gaaagggtag tggtttttta gttgtattgg ttttggtttt ggtttttatt tttagtatgt   2160

tttgttattt taataaagag tggttttttt atttgatttt aatttgtatt agttagtgtt   2220

gaggaaaga                                                           2229
```

```
<210> SEQ ID NO 17
<211> LENGTH: 7833
<212> TYPE: DNA
<213> ORGANISM: Artificial Sequence
<220> FEATURE:
<223> OTHER INFORMATION: chemically treated genomic DNA (Homo sapiens)

<400> SEQUENCE: 17

gtttttggtg agatatgtgt tttataagtt ttaatggaga aaaatgtaag tattttattt     60

tttgaaattt ggttatttga gtaatgagaa aatagttatt ttttttagga tagtggtttt    120

taattatggt tatgtgtttt tttaggaaaa ttttaaaaat atatatatat taatgttttt    180

gtgttatttt tagggatttt aagtttttga atatgaattt tgtattagta ttttttaatt    240

atttaggtga ttgtgatgtg aaattatgat tgagttttat tgttttaaga tgaaataaat    300

ttttttagt attgaaatta taaatttaaa ttattaaaat taattaaggg tatgggaatt    360

aataaggtat agggaagttt ttatattata aaattatttt tttaaattat agtttattgt    420

ttatatgtta tttgttattg tagaaaaggg tgaaaaaata gtaaatttaa ttatttttag    480

tttgaaaaat tatttagaaa tgaagatgat gattttgaaa tattgttaat attatttgat    540

ttataaataa tgttttaata tatttattat atattgatag atattttttt atatgaatat    600

tatatattaa aattaaggta ataatgtatt tagaatattt tatttatatt tatgtatttt    660

aagtaggtta gaaattaaga tatgagttat taagtatgag atgttaaggt gtggggttag    720

aaattatatt gtattttatt attaataatt aatatatatt ttaatattat atatatttaa    780

ttttaatttg tatattttta attattttta attatgtgta taaatataag tatatatatt    840
```

```
tttatgtatt tatttattta tatttttatt tatttattta tataggggat ttttttaaat    900
ttattattat taaattatat atttttattt taatttttag aataagttta ggaggtaggt    960
attgttatta tttatatttt ataaatgagg aaattgttta tagttataaa gttattgtgt   1020
tagatatatt agaagtttaa tatatatttg gtgaatatat gtataaaaat agagagatag   1080
atatgtataa tagtttattt ttatattgag taaaagtttt taatttgttt tagaaatttt   1140
tttgtgaaaa ttgagtaaaa attgaggtat tttttttattt gttatatagg tataggtggt   1200
attttatttt tttaataagg atgaatattg aaatgtggat tttaaggttt aattttagat   1260
tttttgaatt tttgatagtg ggatttggaa tttgtttatt gttttaaagt tttttaagga   1320
atttatatga ttaattaggt ttagaaatta ttggatttta ttgttgaagt ttgagaatta   1380
aagtttgggt tttattgtgg ttttatagaa agggtaaatg aagtattatg gatagaattg   1440
atatgttttt agttagtttt tttttttaga agttaatagg tagtaatata gtagaaatta   1500
gtgatttatg ttttgtgttt tgaagttagg tagaatttta tagagtttta gtagtgttat   1560
tgatgagatt tgttttttgg ggtaagttgt ttgatgtttt taaagttata ttttttttat   1620
ataaaatgag ataatatttt ttgttttata ggggtgtttt aaagattaaa taaaaataat   1680
atgttttatt ttatatggta taatgtttga tatttaagaa gtaaaggata tattttattt   1740
ttattgaagt aattagaaag tatgaaatta tgaaggagat aagagttttg attggtagtg   1800
tattttattt ttttaggttt atttatttat tttaaattat ttttgttgga gaataatttt   1860
taagtttttt atttaagttg tgagtaattt tatattttat aatgatgttt tttttatgag   1920
aaaaaaaaat gtttttaagt tttttggaga aaatatattt gtattatttt tattgaaaaa   1980
tttaataatt ggattttgtt tttttgtatt aattttagag tgtatatgtt ataaataaag   2040
tgttttagtt taagaagatt gaaagtaaat atggtatagt attttaaaat aagaattttg   2100
taaatatatg gtatgattgt gttatattat tagtaattat atgatatgta atgtaaagta   2160
tagtttatag atttaaattt aattttaata agtaaattga ttttgttttg ttggggaaaa   2220
gttaaagtat taatttaatt gttaatgtag ttttgtttat ttttttggta tttagtgata   2280
agtttaaata atgtatatat ttttatttat atatttagta atataatttt ttgtttaatg   2340
agtgatgttt ttttgttatt tggtggtgtt tgttagtttt agaatttgtt ttttggtggt   2400
attataatat taagtataga gtaagtgtaa taaaattgta gtatttttat tgaaaaggtt   2460
ttgttttaaa ttgtttaata atttaaagga tttttgtgga agtaattgta tttgttaatt   2520
agttataatt agtaattaat ttttttggag ttttaattta tttttggtaa aatgttttag   2580
gaagagtata tattattaga aagtatgtta aaaatttatt tagtagaaaa tttaaaaata   2640
gttttttttt gttaagaggt tttttaaaat tttatttata tagttaaatt ttgaaatttt   2700
agtaggtttt gttttattat tataattatt gtataaatat ttttaaggat tttgttttta   2760
gttttaagta tgatttattt ttataagttt gattagttat tatattagtt ttgttatgga   2820
aaatgatatg tttttatttt ttgttgtaga gttgttaaat tttgatttat atttatgttg   2880
tttttttgt tgaaagtttg tagtgaaaga aatttttaat tttttgtttt gtaatattag   2940
ttggtagttt tatttaatgg gtattttgtt tttttaaaga atttagttgt tttgtttaga   3000
agttgatttt ttgatgtttt taatgtttgg tttaattgat ttgttttaat ggagtttttg   3060
ttggtgagga gtgagatgtt attgattaga atgttgggat ttgttgttta attgttagga   3120
gtgagagata ttgagattta gaaatttttg gaggtgggag gggagaggga tagttttgga   3180
tggaggtgga gatgtaagat aaagggatgg attttatata ggaaaaaaaa aaagattttg   3240
```

-continued

```
ttgaggtatt gaggtgttgt atgattatat tttttaaagg agaagttaaa aagtaaggaa   3300
gtgggaggag gttggaggtt aaagtattta aaaggattat ttgggtataa tttgtttttt   3360
tgttggtgtt tgtaaaggat agatagtttt gtttttaaag tatatgaatg ttttttttaa   3420
gtgattggga atggatatta attgtttgtt aaatgttatt aaatgttttt ttaaatttag   3480
gggatataga aagaggggta taaaaggaga atttaaatag aaaaagggag gatttggagg   3540
tttttgaaag tgggggggaga agaaggagga gggataatag agaggaatag agaaggagag   3600
tggagagaag ataaataaaa ataaaaatag gaattattga ataattatat attaaaaaga   3660
aagttttttt ttatggggta tttaaaatat tgagattgta atagtgattt tggttatgga   3720
agaaagatgt tttttttat ttttgttttt gaaagttttt ggttttgtta ttggtgatta   3780
aaattttatt aggttaaaga gtgtgtttaa ttgtttgaag aatgtagtag atggaaggtg   3840
ggttttgtta tgttgtttgt tttttttgtt ggagagaatg aaagaaatgt gtagagttag   3900
agatttttgt tgagttagat tttttttgt tgttttaggt tattggttat ttggtaaaga   3960
tttgagtaag gaatgtaggg ttattgtttg ggttaataaa tggagtttgt ttttttttt   4020
ttggatgttg ttgtttggtt gatgtttttg gtaatttatt tgtggtgtat gtagaggagt   4080
ttttttttt tttttagatt atttgttttg attaatttga ttttttaaat atatttgatt   4140
gtatttttta ggtggatata ttaataggtt atgggttgga gaggagtggg tgatgaggag   4200
agggatttaa atttgtgaat gtttgggttg ggttggagtt gtgggggggtt tgggaggaga   4260
gaggggagaa gagagaagga aggagagtgt ttgttgggat ggttgagttg ttttggtgag   4320
tagttttggg gttgtatgtt tttgtgggag atgttgttgt tgtttttagg ttggtaagag   4380
tggttttaat attattgttt tttattttt tttttgtaaa tttttagaga aatgtttttg   4440
gtttttttgt tgtgatattt ttagtttgta ttttttata gtttaggtgg tgtgtttttg   4500
tatgttggag tgttggttgt tagtaggatg ttttttttg tgttgatttg ttttttttg   4560
ttttgttgtt gttgtttttt tgatattttt gtttttatta tttttagttt ggagagatgt   4620
tatttagttg tggtttgtat ttgtggtttg gggttatgtg tggaagaggg gtgttagttt   4680
ggattttgtt tttggtaggg ggtgttttgg agtggagagt gaggtgaatg gtatatgagt   4740
gtgtgggtag tttattttga agtttgagtt ttttatttga gttatgtttt gtttagtttt   4800
atttgggtta gtgtttggtg agtgagttta tttgtggttt ttgtggttgt ttttttttg   4860
tatttttgta tttatttgtt gatttttttt ttttgggatt tgtattttgt tttattaatt   4920
agagtttgat tgttttttt tatgtgattt tgggtgggtt gaggatttgt tgttttttaa   4980
atgttagagg gatgtgggtg gtagagtttg agaggtggtt gttgggttgt ggggtgtttt   5040
gatttttttt ttattttgtt tttttgggtt ttatttgttt gtttttggat ttttgttttt   5100
ttttgttttt tggtttttta gagttttttt tttatggtag tagtttttg tgtttttggt   5160
gtagtttttt agtggatgat ttttttgttt tggggttgag tttagttttt ggatgttgtt   5220
gaaatttttg agattatgtg tgggtttggt tgttgttttt ttgttgggtg ttattgttat   5280
tgttgttgtt tttgttgttg ttgtttgtgg gatgtttagt agtttgttgt ttggtttttg   5340
tgattttgtg ttttttggaa gttgtttgtt gttgtagagt tgtatgaatt agttatggtg   5400
ttgtgggagt ttttgtggta gtgtagtagt tggatatttt gtgagggttt ttgttggttg   5460
ttgttgttgt ttgttatgtt atttattgta gtttgtttgg tgaagtttgt tgttttttt   5520
attttttaa gtgattgtta aatgtttatt ggttggaatt gttttggtaa gtttagaatt   5580
tttgtttttg attttttaat tttgtagaag aatatgtgta tttagtatag attagtttat   5640
```

```
tttagtgtgt ttttttagtt ttttattttt tattgtttta gatttttaat attatttatt   5700
tttatttaga gaaataaggg gaattgttgt aggtttgggg gtgaggggtg gttttgggat   5760
gggtagaaag tgtaggtgta gtaggaaatt tttgtatgtt tgtgtttata ttggagttgt   5820
gaggattttg agaaatatta aatgggatgg tttttgggt ttattgtttt gaaagagtat   5880
taattttagg ggaaatattg aaatagaagt tttgttatta ttaaagaaaa aagttttatt   5940
aggatgagga agaaataatt ttatgagaaa gaatgagtga gaaagtaata aattaaatgg   6000
tgattgtagg ggaattgttg atttttggta aaggtgttat gaggttgtat tggtttttttg  6060
ttgaagatta ggttatatag attttagagg agttgggttt taatagaatt ttttttttt   6120
ttttttttt ttttttttt ttttttttt tttttttatt tatttatttt ttttttttt   6180
ttattttttt ttttttttagg tggtaaaaga tattggtttt gtagtttaga tatgtttttt  6240
tttttgtttt tttaagtttt aaggtagtat aggggagttg agaaaaagaa tattttgtgg   6300
gtttttttagg ttggagtggg tatgattgag gttggttagg ttttatgtag gtgagttgag   6360
ggtggaattg attttagtgg gtgttgattt ttttattttt ggataggttt ttgtggagtg   6420
ggttaggtat tttttttgtt tgtttgggtt tttttagatt ttgatggtga atgtttggta   6480
ggttttgttt tgttgaagtt ttttaattaa atagggttag aggatgggag ttgttgtatt   6540
tttagttggt atagtatttg gtttgatagt ttgtagtata gggtgtatgt aattttttat   6600
tttttgtgaa tataatttttg ttgtagttaa atttggtttt gaataaagtg ttttttaaag  6660
atgtatataa gttgaagtgt atgtaatttt agagaggagg gaatgattaa ttgtaattta   6720
gggtgaaagt ttgtatagtt tttagttatt attgatgtaa atgttaaaag gaaaattatt   6780
atgtattatt ttaatttatt ttttataaag ataagttgag atatgtaatt ttattagatt   6840
tgggttaata gattgttttt ttttttggta gtttttaaat ttggtatttt aataaaattt   6900
aatatgtttt tataattttt tgatttatgt gtatatgtgt gttgtttttg aaagaataag   6960
ttttattttg ttattgttta attattttt agatgtttta ttatggtaat aattatgagt   7020
ttgtaaaaat aatttttgga aatgttgatg gttttgtagt ttaatataga ttggtttgtt   7080
ttatttttag tttttgtatt gttttaggaa ataattaatt taaatgtgaa gttgatattt   7140
gtaattaaga aattatatat ttattagata ttttaaaggg gattgtataa attaaagaga   7200
ataaattggt tttgtagata ggttgttaag aatttggtat tttgttttta tttttgttaa   7260
tttagaggtg attaattttt atttgagtta aatagattat tatagaaaat attgtgtttg   7320
tttattttta ttattgaggt tttgtttttt ttttgtttgg atatatttta aataaggggt   7380
tgttttagtt gttgaagtaa aagaataatt aaagatgggg aaatggtaaa agggtattta   7440
gagattatta ttagtttttt tttaaaatgt ggagttttgt ggttataaat attgtttatt   7500
taatgagtaa aaaataaaaa taaaaaaaaa ataggaagta aatgttaagt ttttatttat   7560
tattgttagt attaatgtaa gttttaaaaa atagtattat tagaaaagga tattaaagga   7620
gaattgatta gaaaagaatt gtggaaaatg gaaatgaata ttgattattt aattagattt   7680
tgaggttatt agtagatagt gattttgtag tatagttata gttgttggat ttaaaattta   7740
ggataagtat tttaaagttt taaagtagtg ttttttttg ttaaaaattt gtaagatgtt   7800
ttaatgattg gagtgttttt tttgaatttg agg                                7833
```

<210> SEQ ID NO 18
<211> LENGTH: 7833
<212> TYPE: DNA
<213> ORGANISM: Artificial Sequence
<220> FEATURE:
<223> OTHER INFORMATION: chemically treated genomic DNA (Homo sapiens)

<400> SEQUENCE: 18

```
ttttaaattt aaagagaata ttttagttat taaaatattt tatagatttt taataaaaaa      60
aagtattatt ttgaagtttt aaaatatttg ttttaaattt taaatttaat aattatagtt     120
gtattgtaag gttattgttt attgataatt ttaaaattta gttaagtgat taatatttgt     180
ttttattttt tataattttt ttttagttaa ttttttttta gtattttttt ttgatagtgt     240
tatttttaa agtttgtgtt aatattgata gtggtgaatg aaagtttaat atttgttttt     300
tgtttttttt ttatttttat tttttgttta ttaggtggat aatatttatg attataaaat     360
tttatatttt ggaaaagagt tagtgatgat ttttgaatat tttttatta tttttttatt     420
tttaattgtt tttttgtttt aatgattgaa ataatttttt atttgaaatg tatttagata     480
aagaggaaat aaagttttaa taataaagat aaataggtat agtgtttttt gtgatggttt     540
gtttggttta aatgaagatt gattattttt aagttaatag gggtggaagt ggggtgttaa     600
gtttttgata atttatttgt aaaattagtt tatttttttt agtttatgta gtttttttta     660
aaatatttgg taaatatgta attttttgat tgtaaatgtt aattttatat ttaagttagt     720
tatttttaa aataatgtaa gggttaggaa tgaagtaaat tagtttgtgt tggattataa     780
agttattaat atttttaaaa attgtttttg taggtttata attattatta taataaagta     840
tttaaaaagt gattaggtaa tagtaaagtg aaatttattt ttttaaaaat aatatatatg     900
tatgtatgaa ttaagaagtt atagaaatat gttgagtttt attaaaatgt taaatttaga     960
aattgttaaa aaagagaata atttattgat ttaaatttaa tagggttgta tattttaatt    1020
tgtttttgta aaggataaat tagaatgatg tataataatt ttttttttgg tatttatatt    1080
agtaataatt aggaattata taggttttta ttttgagtta tagttggtta tttttttttt    1140
tttaaagtta tatatatttt agtttatata tatttttgaa agatatttta tttagagtta    1200
gatttaatta tagtaaaatt atatttatag aagatgaaaa attatatata ttttatatta    1260
taggttgtta aattgaatgt tatgttagtt aggagtgtag taatttttat tttttggttt    1320
tatttaatta ggaagtttta gtagagtgaa gtttgttaag tgtttgttgt tagaatttga    1380
aggaatttga gtgagtaaga agagtgtttg atttatttta tagaagtttg tttagaaatg    1440
gaggagttag tgtttattga agttggtttt gtttttggtt tgtttatatg gagtttgatt    1500
agttttagtt atgtttattt tggtttggga gatttgtaaa gtgttttttt ttttaatttt    1560
tttgtattat tttgaagttt agggaagtaa agagaggggt atatttggat tgtaaaatta    1620
atgtttttttg ttgtttagga gagaagggaa tgagagagag agagagatag atagatagag    1680
agagagagag agagagagag agagagagag agagagagag agaaatttta ttgaaattta    1740
gtttttttag aatttgtgtg atttggtttt taatgggaga ttagtgtgat tttatggtat    1800
ttttgttagg aattagtgat ttttttgtag ttattatttg atttattgtt tttttgttta    1860
ttttttttta taaagttatt ttttttttat tttagtaaga tttttttttt taatgatgat    1920
aaagtttttg ttttagtgtt ttttttagga ttggtgtttt tttaaaatag tgaatttaga    1980
aaattatttt gtttaatatt ttttaaaatt tttgtagttt taatgtaagt gtaagtatgt    2040
aaaggttttt tgttatattt gtattttttg tttattttag aattattttt tatttttggg    2100
tttgtaatag tttttttttgt ttttttggat agaggtgggt ggtattaggg gtttagggta    2160
gtaggaggtg aggggttgag gaggtgtgtt agggtaggtt ggtttgtgtt ggatatgtgt    2220
gtttttttgt ggagttaaag ggttggggat gggggttttg gatttattag agtaatttta    2280
```

```
gttggtgggt gtttggtagt tatttaagga ggtagggaaa gtagtgagtt ttattgggtg   2340
ggttatgatg agtagtatga tgggtagtag tagtagttag taaaagtttt tgtaaagtgt   2400
ttagttgttg tattgttgtg gggattttta tagtattatg attagtttgt gtaattttgt   2460
agtagtaaat ggtttttgag gaatatagga ttgtgggggt tgggtagtgg gttattgagt   2520
atttgtgga tggtggtagt agaggtggtg gtggtggtag tggtatttgg tggggaagta   2580
gtagttaaat ttgtgtatga ttttgagagt tttagtaata tttagggatt gggtttagtt   2640
ttggagtgag agggttgttt gttgagaagt tgtgttggag atgtgggaag ttgttgttat   2700
aaggagggag ttttgggaag ttggaggata ggaggagatg ggagtttagg ggtagatgag   2760
tggagtttga ggaggtaggg tggagggaga gttaaggtgt tttgtagttt ggtagttgtt   2820
ttttgagttt tgttgtttgt attttttgg tgtttgggaa gtagtaggtt tttagtttgt   2880
ttggggttat gtgggaagag gtagttgggt tttgattggt ggagtaggat gtaggttttg   2940
ggagggaggg gttgatgagt aggtgtaagg atgtaaggag gaggtggttg tggaagttat   3000
agatgggttt gtttgttagg tgttggtttg agtggggtta ggtggggtat ggtttaaatg   3060
agaagtttgg gttttagggt gggttatttg tatatttata tattatttgt tttattttt   3120
gttttaggat gtttttattt gaaggtgggg tttggattag tgtttttttt ttgtgtgtga   3180
ttttgggttg tgagtgtggg ttgtggttgg gtggtgtttt tttgagttgg agatggtggg   3240
ggtggaggtg ttagaggagt agtagtagta gggtagagag gggtgagttg gtgtgggaga   3300
gggtgttttg ttggtgattg gtgttttagt gtgtgggagt gtgttgttta ggttgtaggg   3360
ggatgtaggt tgggaatgtt gtggtggaga ggttagggat gttttttag ggatttatag   3420
gaaagagggt gagaggtgat ggtgttagaa ttgtttttgt tgatttggaa gtaatagtag   3480
tatttttat aagagtgtgt aattttaagg ttgtttgttg aggtagttta gttatttgg   3540
taggtgtttt tttttttt ttttttttt ttttttttt ttaggttttt tgtagttttg   3600
atttagttta agtgtttgta ggtttgaatt tttttttta ttatttgttt tttttagtt   3660
tgtagtttat tagtgtgttt atttgggagg tgtggttaga tgtgtttgga aggttagatt   3720
ggttgggata agtggtttga gagaaagaga aaggtttttt tgtatatgtt gtgggtgggt   3780
tgttgggagt attggttggg tagtggtgtt tgggaagggg agagtgggtt ttatttgttg   3840
gtttaggtag tgattttgtg tttttatttt gggtttttgt tggatggttg gtgatttggg   3900
gtgatgagag aaggtttaat ttggtaggag tttttggttt tgtgtgtttt ttttattttt   3960
tttagtggga agggtaaatg gtatagtggg atttgttttt tgtttgttgt atttttagg   4020
tagttagata tattttttag tttaatggaa ttttagttgt tagtaatggg attaagagtt   4080
tttggggata agggtggaga ggaatatttt ttttttatga ttggggttat tattgtagtt   4140
ttagtgtttt ggatgtttta tagggaagag tttttttttt ggtgtgtgat tatttagtga   4200
tttttgtttt tgtttttgtt tattttttt ttgttttttt tttttatttt tttttgttat   4260
ttttttttt ttttttttt ttgtttttaa aagtttttgg atttttttt tttttattta   4320
aattttttt ttgtgttttt ttttttgtgt tttttgaatt taggagagta tttgataata   4380
tttaataggt aattagtgtt tatttttaat tatttaaaag aggtatttat atattttgaa   4440
aatgggatta tttattttt gtagatatta gtagaaaaat aaattgtatt tgagtaattt   4500
ttttaagtat tttaattttt aatttttttt tattttttg tttttttaatt tttttttga   4560
gagatgtgat tgtgtagtat tttagtgttt taatgaaatt tttttttttt ttttgtgtga   4620
aatttatttt tttattttat atttttgttt ttgtttgaga ttgttttttt ttttttttat   4680
```

```
ttttaaagat ttttgaattt tagtgttttt tatttttggt aattaagtag tagattttag   4740
tattttagtt ggtggtattt tgttttttat tgatgaagat tttattaaaa tagattaatt   4800
agattagatg ttggaggtat tagaaaattg gtttttagat agagtagtta aatttttttaa  4860
ggaaatagaa tatttattag atagagttgt taattaatat tgtaaaataa ggaattagaa   4920
atttttttg ttataggttt ttagtagaga aggtaatata aatatagatt aagatttaat    4980
aattttatag tagagaatga gaatatgtta ttttttatag taaggttggt gtggtaatta   5040
attaggttta tgaaaataag ttatgtttga aattaaaggt aaagttttta aaagtgttta   5100
tgtagtaatt atgataatga aataggattt gttaggattt tagagtttgg ttatgtaagt   5160
agaattttag agaatttttt agtagaggaa aattgttttt gaatttttttg ttaagtaaat  5220
ttttggtata tttttaata atatatgttt tttttaagat gttttgttaa aagtaagtta    5280
aaattttaaa ggagttaatt attggttgta attggttaat aaatgtggtt gtttttatag   5340
aggtttttta aattattaaa tagtttgaag taaagttttt ttaatgggaa tgttgtaatt   5400
ttgttgtatt tattttgtat ttagtgttat agtgttatta agaaataaat tttgaaattg   5460
gtaagtatta ttaagtggta gaagaatatt atttattgag tagagaattg tattattgaa   5520
tatgtaaata aaaatatata tattatttag atttgttatt aggtattaaa gaagtagata   5580
agattgtatt agtaattgga ttagtgtttt aattttttttt tagtaaggta aaattagttt  5640
atttattaga attaaattta agtttatgaa ttgtattttg tattgtgtat tatatgattg   5700
ttagtaatat gatataatta tattatgtat ttgtaaaatt tttattttaa aatattatat   5760
tatatttatt tttaattttt ttgagttaga atattttatt tgtggtatat atattttaga   5820
attgatgtag aggagtagag tttagttgtt agattttttta gtagaaatag tgtagatata  5880
ttttttttag aaaatttaag aatatttttt tttttatgg aaagaatatt attataaagt    5940
gtgagattat ttatagttta agtagggggt ttgggagtta tttttaata agaatagttt    6000
aagataaata aatgaatttg ggaaaataag atatattgtt aattagaatt tttatttttt   6060
ttatgatttt atattttttg attgttttaa taaaggtaag atgtattttt tgttttttag   6120
gtgttaggta ttgtgttatg taggatagaa tatgttattt ttatttaatt tttaaaatat   6180
ttttatgaga taaagaatat tattttattt tatataaaag gaatatggtt ttgaaagtat   6240
taggtaattt gttttaagaa ataaattttg ttagtgatat tgttgggatt ttgtgaaatt   6300
ttgtttgatt ttagagtata agatataagt tattaatttt tgttgtattg ttgtttgtta   6360
gtttttgaga ggggaaatta attgggaatg tattagtttt gtttatgata ttttatttgt   6420
tttttttgtg gagttgtagt aaggtttaaa ttttaatttt taaattttgg taataagatt   6480
tagtgatttt tgaatttggt tgattatatg aattttttga gaaattttga aataatagat   6540
aaattttaag ttttattatt agggatttag aaaatttgga gttgggtttt gggatttata   6600
ttttaatatt tatttttgtt ggagaagtaa ggtattattt atatttatat gataaatgaa   6660
aggatatttt gatttttgtt tagtttttat agagaggttt ttgagatagg ttaaaagttt   6720
ttatttagtg taaagatgag ttgttgtata tgtttgtttt tttgttttta tgtatatgtt   6780
tattaaatat gtattaagtt tttaatatgt ttgatatagt aattttgtga ttgtagataa   6840
tttttttatt tgtaaaatgt gagtaataat aatatttgtt ttttgggttt gttttaaaga   6900
ttaaaataaa aatgtatggt ttaatggtag tggatttggg gggatttttt atataaataa   6960
gtgaatggag gtatgaataa ataaatatat aaagatgtgt gtatttatat ttatatatat   7020
aattaaaaat agttaaagat gtataaatta aagttaaatg tatgtgatat tgaagtatat   7080
```

gttgattatt gataatgaag tatagtataa tttttaattt tatattttaa tattttatat 7140
ttaataattt atattttaat ttttagttta tttaagatat atagatatag atagaatgtt 7200
ttaaatgtat tattgtttta gttttaatgt ataatattta tatgaaaaag tatttattag 7260
tgtgtagtaa atgtattaga atattattta taggttaaat gatattgata atgttttaga 7320
gttgttattt ttatttttgg ataatttttt aaattgagag taattaaatt tgttattttt 7380
ttattttttt ttataatggt aaataatata taaataatga gttgtgattt aaagaaataa 7440
ttttataatg taaaagtttt tttatgtttt attgattttt atgtttttaa ttaattttgg 7500
tagtttaagt ttgtgatttt agtgttgagg aaagtttatt ttattttaga gtagtggggt 7560
ttagttatga ttttatatta taattatttg gataattaaa gaatattgat gtagagtttg 7620
tatttaaaga tttggaattt ttagaagtga tatagaagta ttggtatata tatattttta 7680
aagttttttt ggagaaatat atagttatga ttgagaatta ttgttttggg gaaagtgatt 7740
atttttttat tatttaaata gttaagtttt aggaggtaaa atatttatat ttttttttat 7800
taaaatttgt aaaatatata ttttattaaa gat 7833

<210> SEQ ID NO 19
<211> LENGTH: 5666
<212> TYPE: DNA
<213> ORGANISM: Artificial Sequence
<220> FEATURE:
<223> OTHER INFORMATION: chemically treated genomic DNA (Homo sapiens)

<400> SEQUENCE: 19
aaaattagaa ttttttattt tttgtgtttg ttatattttt tagtgttgtt taattttttt 60
ttgtaagtga gggtggtgga gggtgtttat aattttttta gggagtaagt tttttttggt 120 ttttttttt tttttttttt ttttttttt tgagattaag ttttgttttt gtttttttagg 180 ttggagtgta atggtgtgat tttggtttat tgtaattttt gttttttttt gggtttaagt 240 gatttttta tattagtttt tgagtagttg ggattatagg tatgtgttat taagttttgt 300
taattttgta ttttttagta gagatagggt tttgttatgt tggttaggtt tgttttgaat 360
ttttggtttt aggtgatttg tttgttttgg ttttttagaa tgttgggatt atagatgtga 420
gttattgtat ttggattttt tttttatgta atagtgataa ttttatttaa agtatttttt 480 ttttttttg agttggagtt ttattttgtt atttaggttg gagggtggtg gtgtgatttt 540
ggtttattgt aatttttgtt ttttgggttt aagtgatttt tttgttttag ttttttgagt 600
agttggaatt atatatgtgt gttattatgg ttagttaatt tttgtatttt tagtagagat 660
ggggtgttat tattttggtt aagttggttt tgaatttttg attttaggtg atttgtttgt 720
tttggttttt taaagtgttg ggattatagg tgtgagttat tgtgttttgt ttttaaagtat 780 tttttttta tgttttaaaa taagattgta agttagtttt taaagtggat aatttaagag 840
ttaataggta ttagtttagg atgtgtggta ttgtttttaa ggtttatatg tattaatata 900
ttatttaaat ttataataat ttttataaag tagggggtat ttatattttt tttttttttt 960
ataattatga aaaatgtaag gtatttttag taggaaagag aaatgtgaga agtgtgaagg 1020
agataggata gtatttgaag ttggtttttg gattattgtg taattttgtt tttagaatat 1080
tgagtatttt ttttggttta ggaattatga ttttgagaat ggagtttgtt tttttaatga 1140 ttttttttt atttttttat ttgtttatag gtagaatttt tttttgtttg tattaaataa 1200
attttatttt tttagagttt gtttttatat taggtaatgt atatgtttga gaaatttttg 1260
ttttagatag ttgttttata tgtaggaggg gaaggggagg ggaaggagag agtagtttga 1320

-continued

```
tttttaaaa ggaatttttt gaattagggt ttttgattta gtgaattttg tgtttttgaa   1380
aattaagggt tgagggggta gggggatatt ttttagttgt ataggtgatt ttgatttttg   1440
gtggggtttt tataattagg aaagaatagt tttgtttttt tttatgatta aaagaagaag   1500
ttatattttt tttatgatat taaatatttt gatttaattt ggtagttagg aaggttgtat   1560
tgtggaggaa ggaaatgggg tgggggtgga ttttttttta atagagtgaa tgtatttaaa   1620
tatgtttttg ttggtaggtg ggggagtgtg gttgggagta gggaggttgg agggtggtgt   1680
ggggggtagg tggggaggag tttagttttt ttttttgtt aatgttggtt ttggtgaggg   1740
ttgtttttgg ttggtgtttt tgggggagat ttaatttggg gtgattttag gggtgttata   1800
tttgttaagt gtttggagtt aatagtattt tttttgagta tttgtttatg gtgttttttt   1860
gtttggaaag atattgtggt ttttttagag gatttgaggg atagggttgg agggggtttt   1920
tttgttagta ttggaggaag aaagaggagg ggttggttgg ttattagagg gtggggtgga   1980
ttgtgtgtgt ttggtggttg tggagagggg gagagtaggt agtgggtggt ggggagtagt   2040
atggagttgg tggtggggag tagtatggag tttttggttg attggttggt tatggttgtg   2100
gtttggggtt gggtagagga ggtgtgggtg ttgttggagg tgggggtgtt gtttaatgta   2160
ttgaatagtt atggttggag gttgatttag gtgggtagag ggtttgtagt gggagtaggg   2220
gatggtgggt gattttggag gatgaagttt gtaggggaat tggaattagg tagtgttttg   2280
attttttgga aaaaggggag gttttttggg gagtttttag aaggggtttg taattataga   2340
tttttttttg gtgatgtttt gggggtttgg gaagttaagg aagaggaatg aggagttatg   2400
tgtgtataga ttttttgaat gttgagaaga tttgaagggg ggaatatatt tgtattagat   2460
ggaagtatgt tttttattag atataaaatt tatgaatgtt tgggataaaa agggagtttt   2520
aaagaaatgt aagatgtgtt gggattattt agtttttaat ttatagatat ttggatggag   2580
tttatttttt ttattaggag ggattattag tggaaatttg tggtgtatgt tggaataaat   2640
attgaatata aattttgatt gaaattattt agaagtggtt gggtgtggtg ttttatgttt   2700
tgtaattttt ttattttggg agattaaggt ggggggaatt atttgaggtt gggagtttga   2760
gattagtttg gttaataggt gaaattttgt ttttattaaa aatataaaaa gtagttgggg   2820
gtggtggtag gtgtttgtaa ttttagttat ttgggaggtt gaggtaggag aattgtttga   2880
atttgggagg ttgaggttgt agtgaatagt gagatggagt tattttattt tagtttgggt   2940
gatagagtga gattttgttg aaagaaagaa agagagaaag agagagagaa aaattattta   3000
gaagtaatta tatattgtgt ttatttttaa ttgagtaggg taaataaata tatgtttgtt   3060
gtaggaattt aggaaataat gagttatatt tatgtgatta ttttagaggt aatatgtagt   3120
tattattttg ggaatatttg ttaatatttt tgttttttta ttatttttag tttatttgat   3180
atagtttatt tgtgataaga gtttttaatt ttttattttt gaatagaggt gttttttttt   3240
tttttatttt tgttttgtga gggagttagg ggaggattta aaagtaatta atatatgggt   3300
aatttagtat ttttaaaatt ttgttaatag tttgaatttg ggagtttggt tttgtagttt   3360
tataatattt tagaagagat tttatttgtt taaaaataaa aaggaaaaag aaaagtggat   3420
agttttgata atttttaatg gagaagggag aagaatatgt agaaaagggg aaatgatgtt   3480
ggtttagaat tttaattata ttggtgttta atataggaat atttatttat ataatatttt   3540
aaagtattaa atttatatta gtatattatt aaatggatat attattaaat gggtttaagt   3600
attttatata ttttaattta attgatttat tttttttttg ttttggattt ttattatgat   3660
ttaaatattt atatatgggt tattttttag atttttata ttatgaaata taagaaaaat   3720
```

ttttaaggtt agttttatga ttaagatgaa ggattttatt gaatatataa aataataaat 3780
atattgtaat attttgtttt tttttttgta gttgtaattt ggtttgttta tattttttttt 3840 ttgttttttt gaaaattgag ttagttttat tttttttagga taggatttaa taattataat 3900
ataatttagt ataatttttt gatttaggta aattatgtaa tttgtgttta gtatgaaatg 3960
tatttaaaaa taagtaattt ttttttaata ttattatttt taaattaata taataaataa 4020
tagttatttt aaaataaatt gtttattttt attatgtagt atttaaattt taaggttgtt 4080
atgattgtag atagtatttt aaaatttttt tttggaaatg gttttgtttt taagatgatt 4140
taggaattaa agaggtgatt attttttgtt taatgaattt ttaaattata aatttgggaa 4200
gtgttttagt tttttattgt tgttgttata aattattata aatgtgttag ttaaaataaa 4260
tataaaatta ttattttata gttttagaga ttagaagtta aaaatgggtt tataaggttt 4320
tatttttttt ggaaatttta aggggtaatt tgttttttttg tttttttttag tttttagtga 4380 ttattaaatt ttttggttta tggtttttgt atttttttttg tggtttgtgt ttttattttt 4440
gtattttttt tttgattgtg atttttttaat aaaaatattt ggggttatgt tgggtttatt 4500
ttgaaaattt tggataattt tttttaagat tattaattaa attatatttg taaagttttt 4560
tttgttatat aagttaatgt attaaaagtt tttgaggatt aggatataga tattgggggt 4620
gggggggtat tatttagttt attataggaa ggaattttag ggttaattaa attagttttt 4680
ttattttata tttgaagaaa ttgaagtttt ggaattggag agtattatgt taaatgaaat 4740
aagttaaata tagaaagata aatattatat gtttttattt atttgtgaaa tataaaataa 4800
ttatattttt agtagtaaag agtagaatgg tggttattag agttgggggg tgggaggaat 4860
ggggagatgg taattaagat ataaagtttt agttaagatg ggaggaataa gtttgattgt 4920
tttttttgag atgtgtttta tagtatgatg aatatagtta aatagtaaat tttaaatgtt 4980
tttatttgat aaaaatgtta aatatttgag atgatggata ggttatttag tttgatttaa 5040 taattttttta ttgtgtttaa agattataat tttatattgt attatataaa tatatataat 5100
tgtattattt taatatataa ttttaaaatt aatataatga aaaagaaatt gaagtttaat 5160
atttttagaa gttaagtgta atttaaaagt tttgtgagaa tttgttttaa taaataaata 5220
agtttttttt ttttaataat tattatattt tgtgtttgga tatatagtag tgaataaaaa 5280
aaaaaaaaaa aaaaaaaatt tttaggttta atataatttt aggaagaaat ttttagtagtt 5340 gtattttagg ggaaatatag gaagttagtt tggagtaaaa gttagtttgt ttttgttttt 5400
ttgttatttt gtttgtgttt tatagtgttt tttgtttgtg atgatagttt tgtagaagtt 5460
tggaggatat aatggaattt attgtgtatt gaagaatgga tagagaattt aagaaggaaa 5520
ttggaaattg gaagtaaatg taggggtaat tagatatttg gggtttgtgt gggggtttgt 5580
ttggtggtga gggggtttta tataagtttt ttttttgtta tgttggtttt tattttggtt 5640
ttgattattt tgtttttttt ggtagg 5666

<210> SEQ ID NO 20
<211> LENGTH: 5666
<212> TYPE: DNA
<213> ORGANISM: Artificial Sequence
<220> FEATURE:
<223> OTHER INFORMATION: chemically treated genomic DNA (Homo sapiens)

<400> SEQUENCE: 20
tttgttagag agaatagaat ggttagagtt agggtggggg ttggtatgat ggaaaggaag 60
tttgtgtaga gttttttat tgttaagtag atttttatat aagttttagg tgtttaatta 120

```
tttttatatt tgtttttagt ttttaatttt ttttttgagt tttttattta ttttttagta    180
tataatgaat tttattatat tttttgaatt tttgtggagt tgttgttata ggtagagagt    240
attgtgaggt atgggtaaaa tagtaaaggg gtagggatag attgattttt attttaggtt    300
aattttttgt attttttttg agatataatt attgaaattt tttttgaaa ttatgttagg    360
tttggagatt tttttttttt tttttttttt tgtttattgt tgtatattta agtgtagaat    420
gtggtaattg ttaaaaagag aaaatttgtt tgtttgttaa aataaatttt tataaaattt    480
ttaagttata tttagttttt gggaatgttg aattttaatt ttttttttat tatattagtt    540
ttaaaattat atattgggat agtatagttg tatatattta tgtggtataa tatgaagtta    600
tgatttttga atataatggg gaattattaa gttaagttaa gtaatttatt tattatttta    660
aatatttgat atttttgtta aatgagagta tttgggattt attatttagt tatatttatt    720
atgttatgaa atatatttta aaaaaaataa ttaaatttat ttttttttatt ttaattgagg    780
ttttatattt tgattattat tttttttattt ttttttatttt ttagttttag taattattat    840
tttattttttt attgttaaga atgtaattgt tttatatttt atagataagt gagaatatgt    900
gatatttgtt tttttgtgtt tggtttattt tatttagtat aatgtttttt aattttaaaa    960
ttttaatttt tttaagtata aaataagaag gttagtttaa ttaattttaa aatttttttt   1020
tgtggtaggt tgaataatgt tttttttattt ttaatgttta tgttttaatt tttaaaaatt   1080
tttaatatat taatttatgt ggtaaaagag gttttgtaga tgtgatttaa ttaatggttt   1140
tgagggagat tatttagaat ttttagggtg ggtttaatat aattttaagt gtttttatta   1200
gagggttata gttagagaga agatataaga atggaagtat aggttataga gaaaatatag   1260
agattatgag ttaaggaatt tgatggttat tagaagttgg aaaagataag gaaatagatt   1320
gtttttttaga gtttttaaaa ggaatgaaat tttgtggatt tatttttgat ttttgatttt   1380
tagaattgta aaataataat tttgtgtttg ttttagttaa tatatttgtg ataatttgta   1440
atagtagtag taggaaatta aaatattttt taggtttatg atttgagagt ttattaaata   1500
agagatggtt atttttttgg tttttaaatt attttggaaa taaagttatt tttagagagg   1560
aattttaaaa tattgtttgt agttatagta attttaaaat ttgagtgttg tatggtggaa   1620
gtagataatt tattttagga taattgttat ttgttatatt agtttgagga tggtggtgtt   1680
aaagaggagt tatttatttt taggtatatt ttatattaaa tataaattgt ataatttgtt   1740
taaattaagg aattatatta aattatatta tggttattaa attttgtttt gagaaagtga   1800
aattgattta gtttttaaag agataaagag aaagtataag taaattaaat tgtagttata   1860
aaaagaaaga taaaatgttg tagtatattt attgttttgt gtatttaatg aagtttttttg   1920
ttttggttat aaaattagtt ttaaaggttt tttttatatt ttatagtatg aaaaatttaa   1980
aaagtaattt atatgtaaat atttaaatta tgatagaaat ttaaagtaaa aagaaaatga   2040
attaattgaa ttaaaatgtg taggatgttt aaatttattt gataatatat ttatttgata   2100
atatattaat atgaatttag tattttaaaa tgttatataa ataaatgttt ttatattaaa   2160
tattaatgta gttaggattt taagttaata ttatttttttt tttttttatat gttttttttt   2220
tttttttatt aaaaattgtt aaaattattt attttttttt tttttttttg tttttaaata   2280
aataaggttt tttttaagat attgtaggat tataaagtta aatttttggg tttaagttgt   2340
tggtaaaatt ttagagatgt taagttattt atgtattaat tatttttaaa ttttttttta   2400
atttttttat aaaataggag tagggagagg agaaatattt ttgtttaaaa atgaggaatt   2460
gaaaattttt attataaata aattatatta agtaagttaa agatagtaaa agagtaaaaa   2520
```

-continued

```
tgttagtaga tatttttaaa atggtaatta tatattattt ttggaatgat tatatgaatg   2580

tggtttatta ttttttaagt ttttatagta aatatatatt tatttgtttt atttagttaa   2640

aaataaatat aatatgtagt tgtttttgaa taattttttt tttttttttt tttttttttt   2700

tttttttgat aaagttttat tttgttattt aggttggagt gaagtggttt tattttgttg   2760

tttattataa ttttagtttt ttgggtttaa gtgatttttt tgttttaatt ttttgagtag   2820

ttgggattat aggtgtttgt tattattttt ggttattttt tgtattttta gtagaggtga   2880

ggttttattt gttggttagg ttggttttga atttttgatt ttaggtgatt ttttttgttt   2940

tgatttttta aagtgaaggg attataaggt gtgaggtatt gtgtttggtt gtttttgaat   3000

aattttgatt aaaatttata tttgatattt attttaatat atattataga tttttattga   3060

taattttttt tagtaagaaa gataagtttt atttaggtat ttgtgaattg gaggttaagt   3120

agttttagta tatttttatat ttttttaaga tttttttttt attttaaatg tttgtaaatt   3180

ttgtattgga taaagagtat atttttattt aatataaata tgtttttttt tttagatttt   3240

tttagtattt gagagatttg tatgtgtgtg gtttttttatt tttttttttt ggtttttttaa   3300

gtttttaggg tgttgttagg aggaggtttg tgattataaa tttttttttga aaatttttta   3360

ggaagttttt tttttttttg gagaattgaa gtgttattttg attttaattt ttttgtaaat   3420

tttgtttttt agagttgttt gttatttttt gtttttgttg tagattttttt atttatttgg   3480

attggttttt gattgtaatt atttggtgtg ttgggtagtg tttttgtttt tagtagtgtt   3540

tgtatttttt ttatttgatt ttgggttgtg gttgtggtta gttagttagt tgaaggtttt   3600

atgttgtttt ttgttgttgg ttttatgttg tttttttgttg tttgttgttt gttttttttt   3660

tttttgtagt tgttgagtgt atgtggtttg ttttattttt tggtgattag ttagtttttt   3720

tttttttttt ttttggtgtt ggtggaagag tttttttttga ttttgttttt taaatttttt   3780

ggagggattg tggtattttt ttaggtaagg ggatgttgtg agtgagtgtt tggaggaggt   3840

gttattaatt ttgagtattt agtgaatgtg gtatttttga agttgtttta ggttgggttt   3900

tttttggggg tattagttgg aagtagtttt tgttagagtt agtgttggta aggaaggagg   3960

attgggtttt tttttatttg ttttttatat tgttttttgg tttttttgtt tttagttgtg   4020

ttttttttgtt tgttagtaaa ggtgtgtttg agtgtgttta ttttgttaaa aagaaatttg   4080

tttttgtttt gttttttttt tttgtgatat aattttttta attgttaaat tgaattgggg   4140

tgtttggtgt tatagggaaa gtatggtttt tttttttaat tataagaaaa agtaaaaatta   4200

tttttttttta gttgtgagag ttttattgag aattgaaatt atttgtatga ttagaaagtg   4260

ttttttttatt tttttaattt ttgattttta ggagtgtggg gtttattaag ttagaaattt   4320

tagtttaaag gatttttttt ggagagttgg attgtttttt tttttttttt tttttttttt   4380

tttgtgtgta aaatggttgt ttggggtaag ggttttttag atgtgtatat tgtttggtat   4440

aagagtagat tttgaaaaga tgaggtttat ttaatatgga tgggggagaa ttttgtttgt   4500

aggtagatag gaaaatgggg agggagttat tggaaggatg gattttattt ttaaagttat   4560

aatttttaga ttagaaaaag tgtttagtgt tttagaagta gagttgtata gtgatttaaa   4620

gattagtttt aaatattgtt ttgttttttt tatatttttt atattttttt tttttattga   4680

aaatattttg tattttttgt aattataaag ggggaaggga atatgagtgt tttttgtttt   4740

ataggggttg ttgtgagttt aaatgatgta ttaatatata taagttttaa gaatagtgtt   4800

atatatttta agttaatatt tgttagtttt tgaattattt gttttgagga ttggtttgta   4860

attttgtttt gaggtataga aagaaaatgt tttggagtag gatgtggtgg tttatatttg   4920
```

```
taattttagt attttgggaa gttgaggtgg gtagattatt tgaggttagg agtttgaggt   4980

tagtttggtt aaaatggtga tattttgttt ttattaaaaa tataaaaatt agttggttat   5040

ggtggtgtat gtgtgtaatt ttagttattt aggaggttga ggtaggagaa ttgtttgaat   5100

ttgggaggta gaggttgtag taagttgaga ttgtgttatt attttttagt ttgggtgata   5160

gaatgagatt ttgatttaaa aaaaaaaaaa aatgttttgg atagaattat tattattata   5220

taaaaggaaa gtttggatgt ggtggtttat gtttataatt ttagtatttt gggaggttga   5280

gataggtgga ttatttgagg ttaggagttt gagataagtt tgattaatat ggtgaaattt   5340

tgtttttatt aaaaaatata aaattagtgg ggtttggtgg tgtatgtttg taattttagt   5400

tatttggagg ttgatgtagg agaattgttt gaatttagga gaaggtggag gttgtagtga   5460

gttgagattg tgttattgta ttttagtttg ggagataaga gtgaaatttg gttttaagaa   5520

aaaaagaaag aaagaaagaa agaaagatta agaagaattt atttttgaa aagattatgg   5580

gtatttttta ttatttttat ttataaagaa aagttaaata gtattaaaga gtataataag   5640

tgtaaggagg taaaagtttt aatttt                                        5666
```

```
<210> SEQ ID NO 21
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 21

cgcggtttcg attttaatgc                                               20


<210> SEQ ID NO 22
<211> LENGTH: 21
<212> TYPE: DNA
<213> ORGANISM: Artificial Sequence
<220> FEATURE:
<223> OTHER INFORMATION: chemically treated genomic DNA (Homo sapiens)

<400> SEQUENCE: 22

actccgactt aacccgacga t                                             21


<210> SEQ ID NO 23
<211> LENGTH: 28
<212> TYPE: DNA
<213> ORGANISM: Artificial Sequence
<220> FEATURE:
<223> OTHER INFORMATION: chemically treated genomic DNA (Homo sapiens)

<400> SEQUENCE: 23

cgacgaaatt cctaacgcaa ccgcttaa                                      28


<210> SEQ ID NO 24
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 24

tttcggatgg gaacggtgta                                               20


<210> SEQ ID NO 25
<211> LENGTH: 17
<212> TYPE: DNA
<213> ORGANISM: Artificial Sequence
```

<220> FEATURE:
<223> OTHER INFORMATION: chemically treated genomic DNA (Homo sapiens)

<400> SEQUENCE: 25
ctcccaccgc cgttacc 17

<210> SEQ ID NO 26
<211> LENGTH: 21
<212> TYPE: DNA
<213> ORGANISM: Artificial Sequence
<220> FEATURE:
<223> OTHER INFORMATION: chemically treated genomic DNA (Homo sapiens)

<400> SEQUENCE: 26
cccgtcctaa ccgtccgccc t 21

<210> SEQ ID NO 27
<211> LENGTH: 21
<212> TYPE: DNA
<213> ORGANISM: Artificial Sequence
<220> FEATURE:
<223> OTHER INFORMATION: chemically treated genomic DNA (Homo sapiens)

<400> SEQUENCE: 27
tcgtcgtcgt ttcggttagt t 21

<210> SEQ ID NO 28
<211> LENGTH: 19
<212> TYPE: DNA
<213> ORGANISM: Artificial Sequence
<220> FEATURE:
<223> OTHER INFORMATION: chemically treated genomic DNA (Homo sapiens)

<400> SEQUENCE: 28
ccctccgaaa cgctatcga 19

<210> SEQ ID NO 29
<211> LENGTH: 21
<212> TYPE: DNA
<213> ORGANISM: Artificial Sequence
<220> FEATURE:
<223> OTHER INFORMATION: chemically treated genomic DNA (Homo sapiens)

<400> SEQUENCE: 29
cgaccataaa cgccaacgcc g 21

<210> SEQ ID NO 30
<211> LENGTH: 21
<212> TYPE: DNA
<213> ORGANISM: Artificial Sequence
<220> FEATURE:
<223> OTHER INFORMATION: chemically treated genomic DNA (Homo sapiens)

<400> SEQUENCE: 30
tttttttttc ggacgtcgtt g 21

<210> SEQ ID NO 31
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 31
cctctacata cgccgcgaat 20

<210> SEQ ID NO 32
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 32
aattaccgaa aacatcgacc ga 22

<210> SEQ ID NO 33
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 33
tggaattttc ggttgattgg tt 22

<210> SEQ ID NO 34
<211> LENGTH: 19
<212> TYPE: DNA
<213> ORGANISM: Artificial Sequence
<220> FEATURE:
<223> OTHER INFORMATION: chemically treated genomic DNA (Homo sapiens)

<400> SEQUENCE: 34
aacaacgtcc gcacctcct 19

<210> SEQ ID NO 35
<211> LENGTH: 18
<212> TYPE: DNA
<213> ORGANISM: Artificial Sequence
<220> FEATURE:
<223> OTHER INFORMATION: chemically treated genomic DNA (Homo sapiens)

<400> SEQUENCE: 35
acccgacccc gaaccgcg 18

<210> SEQ ID NO 36
<211> LENGTH: 19
<212> TYPE: DNA
<213> ORGANISM: Artificial Sequence
<220> FEATURE:
<223> OTHER INFORMATION: chemically treated genomic DNA (Homo sapiens)

<400> SEQUENCE: 36
gaaccaaaac gctccccat 19

<210> SEQ ID NO 37
<211> LENGTH: 27
<212> TYPE: DNA
<213> ORGANISM: Artificial Sequence
<220> FEATURE:
<223> OTHER INFORMATION: chemically treated genomic DNA (Homo sapiens)

<400> SEQUENCE: 37
ttatatgtcg gttacgtgcg tttatat 27

<210> SEQ ID NO 38
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 38
cccgtcgaaa acccgccgat ta 22

<210> SEQ ID NO 39
<211> LENGTH: 21
<212> TYPE: DNA
<213> ORGANISM: Artificial Sequence
<220> FEATURE:
<223> OTHER INFORMATION: chemically treated genomic DNA (Homo sapiens)

<400> SEQUENCE: 39
gcgtcggagg ttaaggttgt t 21

<210> SEQ ID NO 40
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 40
ctctccaaaa ttaccgtacg cg 22

<210> SEQ ID NO 41
<211> LENGTH: 19
<212> TYPE: DNA
<213> ORGANISM: Artificial Sequence
<220> FEATURE:
<223> OTHER INFORMATION: chemically treated genomic DNA (Homo sapiens)

<400> SEQUENCE: 41
aactcgctcg cccgccgaa 19

<210> SEQ ID NO 42
<211> LENGTH: 10
<212> TYPE: DNA
<213> ORGANISM: Artificial Sequence
<220> FEATURE:
<223> OTHER INFORMATION: Primer

<400> SEQUENCE: 42
gcgccgacgt 10

<210> SEQ ID NO 43
<211> LENGTH: 10
<212> TYPE: DNA
<213> ORGANISM: Artificial Sequence
<220> FEATURE:
<223> OTHER INFORMATION: Primer

<400> SEQUENCE: 43
tgcgacgccg 10

<210> SEQ ID NO 44
<211> LENGTH: 10
<212> TYPE: DNA
<213> ORGANISM: Artificial Sequence
<220> FEATURE:
<223> OTHER INFORMATION: Primer

<400> SEQUENCE: 44
ctcccacgcg 10

<210> SEQ ID NO 45
<211> LENGTH: 2501
<212> TYPE: DNA
<213> ORGANISM: Homo Sapiens

<400> SEQUENCE: 45

```
cttggactct aatgtgtatt ttacacttac agcacaatta atttgggact agctacattt     60
cagctcaaca atagccaata gcatatggga tagcgcaaat aaactctgcg tctctgttgc    120
ttctttgggt ctcggagacc tcaacccttt cttcagattg caaaccttct tgccttcaag    180
cctcggctcc aacaccagtc cggcagagga acccagtcta atgaggtacg ctcccttcct    240
gccattctct attccattaa cctgtttcgt ggtaaacgta ggactgatcc tccaaaatta    300
ccttattaat tagcttacat atttattatc tatctgtccc accagaatgc aggtttccgg    360
aaggcaggga tttaaaaaaa tctgttttgt tctatgtgat tttcccatac caagcaccgt    420
gcccggcaca agctgggatc ccagtacaca tctcgggacg gaagaaccgt gtttccctag    480
aacccagtca gagggcagct tagcaatgtg tcacaggtgg ggcgcccgcg ttccgggcgg    540
acgcactggc tccccggccg gcgtgggtgt ggggcgagtg ggtgtgtgcg gggtgtgcgc    600
ggtagagcgc gccagcgagc ccggagcgcg gagctgggag gagcagcgag cgccgcgcag    660
aacccgcagc gccggcctgg cagggcagct cggaggtggg tgggccgcgc cgccagcccg    720
cttgcagggt ccccattggc cgcctgccgg ccgccctccg cccaaaaggc ggcaaggagc    780
cgagaggctg cttcggagtg tgaggaggac agccggaccg agccaacgcc ggggactttg    840
ttccctccgc ggaggggact cggcaactcg cagcggcagg gtctggggcc ggcgcctggg    900
agggatctgc gccccccact cactccctag ctgtgttccc gccgccgccc cggctagtct    960
ccggcgctgg cgcctatggt cggcctccga cagcgctccg gagggaccgg gggagctccc   1020
aggcgcccgg gtgagtagcc aggcgcggct ccccggtccc cccgaccccc ggcgccagct   1080
tttgctttcc cagccagggc gcggtggggt ttgtccgggc agtgcctcga gcaactggga   1140
aggccaaggc ggagggaaac ttggcttcgg ggagaagtgc gatcgcagcc gggaggcttc   1200
cccagccccg cgggccgggt gagaacaggt ggcgccggcc cgaccaggcg ctttgtgtcg   1260
gggcgcgagg atctggagcg aactgctgcg cctcggtggg ccgctccctt ccctcccttg   1320
ctcccccggg cggccgcacg ccgggtcggc cgggtaacgg agagggagtc gccaggaatg   1380
tggctctggg gactgcctcg ctcggggaag gggagagggt ggccacggtg ttaggagagg   1440
cgcgggagcc gagaggtggc gcgggggtgc caccgttgcc gcaggctgga gagagattgc   1500
tcccagtgag gcgcgtaccg tctgggcgag ggcttcattc ttccgcggcg tccctggagg   1560
tgggaaagct gggtgggcat gtgtgcagag aaaggggagg cggggaggcc agtcacttcc   1620
ggagccggtt ctgatcccaa cagaccgccc agcgtttggg gacgccgacc tcggggtgcc   1680
gtggtgcccg gccccacgcg cgcgcggggc tgaggggtcg gggcgtccc tggccgccca    1740
gctttaacaa agggtgctcc tctccacccc gcgaggaggg gcagctccgg agacccggtc   1800
ttcagcgagc ggggtcttag cgccggggag gtctacttcc ttttggggtt gccattttac   1860
tattattatt gcctttttttt tttcttcaaa aggactggag actgatgcat gagggggcta   1920
cggaggcgca ggagcggtgg tgatggtctg ggaagcggag ctgaagtgcc ctgggctttg   1980
gtgaggcgtg acagtttatc atgaccgtgt tcaggcagga aaacgtggat gattactacg   2040
acaccggcga ggaacttggc aggtaaaggg ggtaccagaa gcgtaccctc ctggattgtg   2100
gaaatgcata acgatggggc cattgggtgg taaacaaatg cagtttgaat caggcgtctc   2160
cctcgccctt tctggagatg cgcaaatcat agagaaaaga gttactaacc cagcggtaaa   2220
ccgcctgatc caagggcctg gggtggaggg agaggcagca gttcagggct agattatgat   2280
gcacagtata ttgatccagt cccctggaca aaatcagatt taattgtccg tgctaactct   2340
```

tgtcagccct tgcccttctg tgacaacagg acaaacacta agattataat tgcaattgga 2400
gttagctttt atgtgtgatt taaacggagg gtacaaacta attaataggt tttaaaaatc 2460
ttagtacttt accctctatc taaattttca gtgtaatttg a 2501

<210> SEQ ID NO 46
<211> LENGTH: 4501
<212> TYPE: DNA
<213> ORGANISM: Homo Sapiens

<400> SEQUENCE: 46
ttcacttgtc ctacaggatt ccccatggaa tcttggagtt tttgaggcga gagggatcct 60
ggataccact gagttctatc tttcatccaa taaacacaga agtggacgcc tggacaggca 120
aagtgacttg accaaggcag gtgcacagct attctgcaac attgggaaca aatctcaggt 180
cttttgattt tttgtttcca ctttactctc ttttcatttc ccagaaacaa agttttcatg 240
tgcttttttt tatagtgata tgtttggaat gcattagcta gtaatttagg aagggaaaaa 300
aataaacaca caagagataa acctgtcagg aggacaaacc tgtattgctt ctgattggct 360
cagagggtga ttattatcat ggtagagaat tatttaatca gtgtaagtaa aatttctctg 420
tgggctgggc actgtacaaa gactcaaacg aatctgtcta cagatctgaa aagcagatac 480
gagatctgtg aatggctggg gtttccaagc ccacagtaca agcatgggcc acaccttaca 540
gcttggagga ctgagccctg aaaatgggca agttccttca cttctctgaa ccttattttt 600
cccacattta aaacaaggat gagtagtttc tgaggtcctt tttacgactt ctcttcctac 660
agactctagc atcctataac ttgatacaaa gagggtggat atgaactcac ctttcctaga 720
aaagttccag gaaagagaat accaggtcat cctagtaggt gtgtagacag gccagataga 780
tcttgaaact tactcagttc ttcccagatg tataactcta tcattgttct tagctgtcaa 840
gagaaagcag gagagcctgc atcttcattc tttttttttt tttttttttt tttggagacg 900
gagtctcact ccatcaccta ggctagagtg cagtggcatg atctcagctc actgcaagct 960
ccgcctccca ggttcacgcc attctcctgc ctcagcctcc caagtaactg ggactacagg 1020
cgcccaccac cacacctggc taattttttg tgttgttagt acagacgggg tttcaccatg 1080
ttagccagga tggtctcgat ctcctgacct cgtgatccgc ccaccttggc ctctcaaagt 1140
gctgggatta caggcgtgag ccaccgcacc cagcctgcat cttcattctt actgttagcc 1200
tcaggttcac ccccacctagc ttattaagtg atgttgaata accaattctt acatattatt 1260
aggctcatgg acaccatgac atccagactg atgggtgcct gctgaagggg gtgaccctag 1320
caggaggact cccctacgca aggattcatg gagtttgctg tttcttttcc ttagggtgag 1380
aaccaaactg ccttcacacg gtgggcagag gggaactgac tcaggtttgg aataagagag 1440
aacatcccaa ctgaaaagct cttggaattc gctgaacttc aagacactgt gtggaccagc 1500
ttaggatagg gagtgagaag aaattaacca aaaggtaatt tcgttacttt tcagctggaa 1560
aaaagatcag attatacttg tgctttcata attaagtagc tgctggaaaa aaacgcttca 1620
gatgctttct atgagaaaac tgctgcttga agttcagcag aagttatcta cttgatactt 1680
atattccagg caaggccttc cgttggagaa aatatcggca ctttggacaa aactgaaatg 1740
tgaaaagaaa gggaagagag ggcctctatc atgtaagatg cttatccaaa gtggatttgg 1800
tctggaaagt cttctaaaac cttccacatg actgtggaat aagtcatgtg gggcgcgggg 1860
ataagcgaat ctctcaaatt ccaccacgta tgccctcatt caacctggat ccttagagtg 1920
gcctccaggg cactctgctc aggactcagt cagctgttgg ccacacccat gctctccagt 1980

-continued

```
ctcctgagac cctatttggt tctgagaggg ctaaaaagca gtgtggctaa atatcccagg   2040
cctcaaagta ttcctactgt ggttggggaa gcaatagaat catacccat aaaacaatga   2100
aaacagtgct agaaaaacat cgagagacag aaacatctct acgagttagg ccacagttag   2160
agtgaaggca gggaaggttt ttaaagctgg gtggagggga caagtcaaaa agatgtggaa   2220
actggtttcc ctttcctatg gctaaagtgc tcaaagggga aaaaggagtt tcaaaaatgt   2280
tcttggaaat accatctctc acgaattctt cggcctctgc tgtcccaatg tcacttgtct   2340
gagatgtaaa cagaggagtt ctgagaaaga agctgaactt gcatttctcc ctgtttctat   2400
ttgttccaaa cttgtggcat ttctaacagg atgaagcgga agagaaaggg aaagagacaa   2460
aagtgtagaa agatggaaga tcccagctgc aaatggccat ttgcagttag atggaacagc   2520
tgctgacgtt cagggaaatg catgtctctc ttcagatggg aaggagcagt ggaaaggggt   2580
gacgagttcc tggctggcca ccaatcatcc catctttctg tgccggttcc tcatctggaa   2640
agtgggagtg atacttgtgc ttgcttttcc tacccacaaa gattattgtg agagctataa   2700
tacggtgaga tacagaatcc tgcttttaaa aatacaaagc agaatcaaga tgtcaataat   2760
aaggatagta attgtgttag ttatctgcaa tcatctatta tagctagtcg tctaggatcc   2820
tggatcgttc tcctggtttt actacagttt tggatcagct cacccccaaa tcccttgctg   2880
aagggtggag ctctgtcagc catgggcagg gaaccacttc ctcttgcctt tctactttct   2940
gtctttcaaa catgcccagg gtctttgcac ttgctgttcc ccctgcctgg tacctctctc   3000
ctgtggcttg ccccagagct gatccttgtc tttgtccact tctcagcgag gatggcactt   3060
cagggagccc ttcccttact atcgcagaga gagcaggccc tccccagtca tgtccaaccc   3120
agaactctgt tttgttttct tcatagccct agcatcacag aaaatcaccc tgtgcattca   3180
tggatgtcca cgggggcaag ggctttgtgt tgcttaaccc agcatcctga accgtgtttg   3240
ttgaatgaat acagaacccc gtttgctctg ggagagcaca gaaaacagtc ttctatcata   3300
tatcatagcc agctgcaaac agcagatggc ttcccatatc ccagagagta agaaccagag   3360
agagagagaa agagagagag tttgggtctt tctcctctgt gcctgctctc tccagagaaa   3420
ctggaggggt agcagttagc attcccccgc tggttccacc aagcacagtc aaggtctcta   3480
ggacatggcc accccctcacc tgtggaagcg gtcctgctgg ggtgggtggg tgttagttgg   3540
ttctggtttg ggtcagagac acccagtggc ccaggtgggc gtggggccag ggcgcagacg   3600
agaaggggca cgagggctcc gctccgagga cccagcggca agcaccggtc ccgggcgcgc   3660
cccagcccac ccactcgcgt gcccacggcg gcattattcc ctataaggat ctgaacgatc   3720
cgggggcggc cccgccccgt taccccttgc ccccggcccc gccccctttt tggagggccg   3780
atgaggtaat gcggctctgc cattggtctg agggggcggg ccccaacagc ccgaggcggg   3840
gtccccgggg gcccagcgct atatcactcg gccgcccagg cagcggcgca gagcgggcag   3900
caggcaggcg gcgggcgctc agacggcttc tcctcctcct cttgctcctc cagctcctgc   3960
tccttcgccg ggaggccgcc cgccgagtcc tgcgccagcg ccgaggcagc ctcgctgcgc   4020
cccatcccgt cccgccgggc actcggaggg cagcgcgccg gaggccaagg ttgccccgca   4080
cggcccggcg ggcgagcgag ctcgggctgc agcagccccg ccggcggcgc gcacggcaac   4140
tttggagagg cgagcagcag ccccggcagc ggcggcagca gcggcaatga ccccttggct   4200
cgggctcatc gtgctcctgg gcagctggag cctgggggac tggggcgccg aggcgtgcac   4260
atgctcgccc agccaccccc aggacgcctt ctgcaactcc gacatcggta agcgctcctg   4320
gtgccccgcc cgagccccac gctgcagcca ggactgcagc gctgcttagg gaggcagggc   4380
```

gagccccact cctttcctct gccccaggag aggggcagac ggggttgggg cggagtggag 4440
aaactcgatg tccttgggcg ggggcgctgg catagctgag aggggaagat gccctgcaga 4500
g 4501

<210> SEQ ID NO 47
<211> LENGTH: 3001
<212> TYPE: DNA
<213> ORGANISM: Homo Sapiens

<400> SEQUENCE: 47
gaagtgctaa tgtcagattt ttacccacta cataagccca ctcttgtact agggcagtga 60
ctttcttctt tgggtgagac cttgaaatct gggattataa ttttgaatta taattataaa 120
atggtatttg gctgtaaatt atctcctttt tttttctgtt cctcacagtt gatattatgg 180
attcccataa ggattcatgt cttctattca ctttaatgaa cagttgttgg gcaacaattc 240
tagaagagtt ccaattctca tcaggagaat ggacaaggtg gagaagcaga gaaaatgcaa 300
tgagtagaat gtctaagtca tcactttgga attgactgaa cataaataaa aatgagaaag 360
atacgtaaaa aagaagggaa tgggtaagca gggtgatgtc tgggagagga ggggctccat 420
agccatgaga gtcaactctg taacacccta tagggttaca acactgccct tcatatactg 480
aggtagcagc agggaaactt tttaattatt agaaatattg aactttgcct cccaccccca 540
aacatttttc tcattcagtt cctgttcttt tttatttctg taatttttac tgtttcaaaa 600
atgatctttt ttctttcgga agaagcaatt cttcaaatcc agttcacata aggggatttg 660
atatgttcaa caagctccaa atacactgta tccagcaata cctactacat gcctactttg 720
agctctgagc aacctgcacc tcaagcctag ttctcattgt tttgcttttg gcaaattttc 780
actaagtgcc cttcctcccc aaacacacgt atatgtctac cagaccctaa agccctttat 840
gaacatgcaa actcctccct tctgaaaacc tttgcgtgag tggtcagcag gctaattcat 900
ccattgcaat gtggctttgt gttagggttc tgtttccgtg ctgcctgcaa gataatcaca 960
gatgtgactg catcttagaa gttcctgaat ctttcaagac agtctggttc acaagaaaat 1020
taaaaggtgg aggtcgggcg cggtggctca cgcctgcaat cccagcactt tgggaggccg 1080
aggcgggcgg atcacctgag gttgggagtt cgaaaccagc ctgaccaaca tggggaaacc 1140
ccgtctctgc taaaaataca aaattagcca ggcgtggtgg tgcatgcctg taatcccagc 1200
tactcgggag gctgaggcag gagaatcgct tgaacccggg aggcagaggt tgcgatgagc 1260
cgagatcgtg ccattgcact ccagcctggg caacaagagc gaaactctgc cacacacaca 1320
caaacacaca cacacacaca cacacggtgt agtttaggaa gtaaaaaaaa aaaaaaaaaa 1380
aaaatcagat ctcccctcac acctcagatc tgaaggcaca aactctaggg ccagggcgtt 1440
cgcctaccca actccacatg cacttgcagg tcacctagca ctcaggtacc tagcactcag 1500
gtacattgtg gctccttacc tctcacgaca gcagcaacaa cgttgattgg aagtttatca 1560
ctgtgtgtta cgggccatgg gccatgtgtg ttagaatttt atgtgaaatt aacatttaat 1620
tctcacggac accccctgaaa cagatgccac agccccccatt ttgccaacga ggcagctgag 1680
gttcccagag gctcaatacc agcaccatga gccgcagcac gcaaggcaaa cacagccgga 1740
ggtgagcaca tacctgcttc gcaccccatg cgcctaacca caaggttccc tccctccagg 1800
aaggccgttg tcttccctgg gacgacttgc cagctctgag gcatgacagt acgggccccc 1860
agaagggtga ccaggaggcc ctcctcgtcc cagctgccgg cgtcgccgcc cactgcaggg 1920
cccgggctgt gactcgtggg gacggttccc tgcgccccgg cgggggaggt gggcggggag 1980

```
gggcggcggg gcgccggggc ggggctcggg acggccgggc tgggagctgg agcccacagc   2040
gggaagcggc cgccgcccgg gcctcgcagg gctaggcgag gcgagggggg gcggggccgg   2100
gcgctacggg aaggggaggc cgcgcggacc gggagccgca ccgcgccagc cgggctgcag   2160
cggccgcgca ccaaggctgc gatggggctg gagacggaga aggcggacgt acagctcttc   2220
atggacgacg actcctacag ccaccacagc ggcctcgagt acgccgaccc cgagaagttc   2280
gcggactcgg accaggaccg ggatccccac cggctcaact cgcatctcaa ggtgaagccc   2340
ggggcgggcg ggcccaagtc cccgctgagg ccgggaggtg cgggcgcccc tcagccccgc   2400
cctaacccgt cccaccattg ctaccgggtc ggccccgcag ggtctgagac ccgcaccctt   2460
ccccggtccc acccgtcacc aggccgcccg cgtagccagg aattcttagc caggttcctg   2520
tgcgcccacc gtgaccctaa gagaagaggc ggacgccctg gcacgtcctt ccctcctgct   2580
tcccccgccc aaagcgctcc cggttcccgg ggcgtcaggt tggctgacag ttcggggtcc   2640
ctgcgtcctg tctcctcagc tgggcttcga ggatgtgatc gcagagccgg tgactacgca   2700
ctcctttgac aaagtgtgga tctgcagcca tgccctcttt gaaatcagca aatacgtaat   2760
gtacaagttc ctgacggtgt tcctggccat tcccctggcc ttcattgcgg gaattctctt   2820
tgccaccctc agctgtctgc acatctggtg agacggggca caccgggtgg accggctttc   2880
tgaaacatgg gcatattctc cgccacctgc cccctactct cctcttatcc caggccggcg   2940
tcaggaggag gaacgcgcat cagttcccaa gcagtaggaa gaactggaag gccttgaaag   3000
g                                                                   3001
```

<210> SEQ ID NO 48
<211> LENGTH: 2501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 48

```
tttggatttt aatgtgtatt ttatatttat agtataatta atttgggatt agttatattt     60
tagtttaata atagttaata gtatatggga tagcgtaaat aaattttgcg tttttgttgt    120
ttttttgggt ttcggagatt ttaatttttt ttttagattg taaatttttt tgtttttaag    180
tttcggtttt aatattagtt cggtagagga atttagttta atgaggtacg tttttttttt    240
gttatttttt attttattaa tttgtttcgt ggtaaacgta ggattgattt tttaaaatta    300
ttttattaat tagtttatat atttattatt tatttgtttt attagaatgt aggttttcgg    360
aaggtaggga tttaaaaaaa tttgttttgt tttatgtgat ttttttatat taagtatcgt    420
gttcggtata agttgggatt ttagtatata tttcgggacg gaagaatcgt gtttttttag    480
aatttagtta gagggtagtt tagtaatgtg ttataggtgg ggcgttcgcg tttcgggcgg    540
acgtattggt ttttcggtcg gcgtgggtgt ggggcgagtg ggtgtgtgcg gggtgtgcgc    600
ggtagagcgc gttagcgagt tcggagcgcg gagttgggag gagtagcgag cgtcgcgtag    660
aattcgtagc gtcggtttgg tagggtagtt cggaggtggg tgggtcgcgt cgttagttcg    720
tttgtagggt ttttattggt cgtttgtcgg tcgtttttcg tttaaaaggc ggtaaggagt    780
cgagaggttg tttcggagtg tgaggaggat agtcggatcg agttaacgtc ggggattttg    840
tttttttcgc ggaggggatt cggtaattcg tagcggtagg gtttggggtc ggcgtttggg    900
agggatttgc gttttttatt tattttttag ttgtgttttc gtcgtcgttt cggttagttt    960
tcggcgttgg cgtttatggt cggttttcga tagcgtttcg gagggatcgg gggagttttt   1020
```

```
aggcgttcgg gtgagtagtt aggcgcggtt tttcggtttt ttcgattttc ggcgttagtt   1080
tttgtttttt tagttagggc gcggtggggt ttgttcgggt agtgtttcga gtaattggga   1140
aggttaaggc ggagggaaat ttggtttcgg ggagaagtgc gatcgtagtc gggaggtttt   1200
tttagtttcg cgggtcgggt gagaataggt ggcgtcggtt cgattaggcg ttttgtgtcg   1260
gggcgcgagg atttggagcg aattgttgcg tttcggtggg tcgttttttt ttttttttg    1320
ttttttcggg cggtcgtacg tcgggtcggt cgggtaacgg agagggagtc gttaggaatg   1380
tggttttggg gattgtttcg ttcggggaag gggagagggt ggttacggtg ttaggagagg   1440
cgcgggagtc gagaggtggc gcgggggtgt tatcgttgtc gtaggttgga gagagattgt   1500
ttttagtgag gcgcgtatcg tttgggcgag ggttttattt tttcgcggcg tttttggagg   1560
tgggaaagtt gggtgggtat gtgtgtagag aaaggggagg cggggaggtt agttattttc   1620
ggagtcggtt ttgattttaa tagatcgttt agcgtttggg gacgtcgatt tcggggtgtc   1680
gtggtgttcg gttttacgcg cgcgcggggt tgaggggtcg gggcgttttt tggtcgttta   1740
gttttaataa agggtgtttt tttttatttc gcgaggaggg gtagtttcgg agattcggtt   1800
tttagcgagc ggggttttag cgtcggggag gtttattttt ttttggggtt gttattttat   1860
tattattatt gttttttttt tttttttaaa aggattggag attgatgtat gagggggtta   1920
cggaggcgta ggagcggtgg tgatggtttg ggaagcggag ttgaagtgtt ttgggttttg   1980
gtgaggcgtg atagtttatt atgatcgtgt ttaggtagga aaacgtggat gattattacg   2040
atatcggcga ggaatttggt aggtaaaggg ggtattagaa gcgtattttt ttggattgtg   2100
gaaatgtata acgatggggt tattgggtgg taaataaatg tagtttgaat taggcgtttt   2160
tttcgttttt tttggagatg cgtaaattat agagaaaaga gttattaatt tagcggtaaa   2220
tcgtttgatt taagggtttg ggggtggagg agaggtagta gtttagggtt agattatgat   2280
gtatagtata ttgatttagt tttttggata aaattagatt taattgttcg tgttaatttt   2340
tgttagtttt tgttttttttg tgataatagg ataaatatta agattataat tgtaattgga   2400
gttagttttt atgtgtgatt taaacggagg gtataaatta attaataggt tttaaaaatt   2460
ttagtatttt atttttattt taaattttta gtgtaatttg a                      2501
```

<210> SEQ ID NO 49
<211> LENGTH: 2501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 49

```
ttaaattata ttgaaaattt agatagaggg taaagtatta agatttttaa aatttattaa     60
ttagtttgta tttttcgttt aaattatata taaaagttaa ttttaattgt aattataatt    120
ttagtgtttg ttttgttgtt atagaagggt aagggttgat aagagttagt acggataatt    180
aaatttgatt ttgtttaggg gattggatta atatattgtg tattataatt tagttttgaa    240
ttgttgtttt ttttttattt ttaggttttt ggattaggcg gtttatcgtt gggttagtaa    300
tttttttttt tatgatttgc gtatttttag aaagggcgag ggagacgttt gatttaaatt    360
gtatttgttt attatttaat ggttttatcg ttatgtattt ttataattta ggagggtacg    420
tttttggtat tttttttatt tgttaagttt ttcgtcggtg tcgtagtaat tatttacgtt    480
tttttgtttg aatacggtta tgataaattg ttacgtttta ttaaagttta gggtatttta    540
gtttcgtttt ttagattatt attatcgttt ttgcgttttc gtagtttttt tatgtattag    600
```

```
tttttagttt ttttgaagaa aaaaaaaagg taataataat agtaaaatgg taattttaaa    660
aggaagtaga ttttttcggc gttaagattt cgttcgttga agatcgggtt ttcggagttg    720
ttttttttcg cggggtggag aggagtattt tttgttaaag ttgggcggtt agggacgttt    780
tcgatttttt agtttcgcgc gcgcgtgggg tcgggtatta cggtatttcg aggtcggcgt    840
ttttaaacgt tgggcggttt gttgggatta gaatcggttt cggaagtgat tggtttttttc   900
gttttttttt tttttgtata tatgtttatt tagttttttt atttttaggg acgtcgcgga    960
agaatgaagt tttcgtttag acggtacgcg ttttattggg agtaattttt ttttagtttg   1020
cggtaacggt ggtattttcg cgttattttt cggttttcgc gtttttttta atatcgtggt   1080
tatttttttt ttttttttcga gcgaggtagt ttttagagtt atatttttgg cgattttttt  1140
ttcgttattc ggtcgattcg gcgtgcggtc gttcgggggga gtaagggagg gaagggagcg  1200
gtttatcgag gcgtagtagt tcgttttaga ttttcgcgtt tcgatataaa gcgtttggtc   1260
gggtcggcgt tatttgtttt tattcggttc gcggggttgg ggaagttttt cggttgcgat   1320
cgtatttttt ttcgaagtta agtttttttt cgttttggtt tttttagttg ttcgaggtat   1380
tgttcggata aattttatcg cgttttggtt gggaaagtaa aagttggcgt cgggggtcgg   1440
ggggatcggg gagtcgcgtt tggttattta ttcgggcgtt tgggagtttt ttcggttttt   1500
tcggagcgtt gtcggaggtc gattataggc gttagcgtcg gagattagtc ggggcggcgg   1560
cgggaatata gttagggagt gagtgggggg cgtagatttt ttttaggcgt cggttttaga   1620
ttttgtcgtt gcgagttgtc gagttttttt cgcggaggga ataaagtttt cggcgttggt   1680
tcggttcggt tgtttttttt atatttcgaa gtagttttttc ggtttttttgt cgtttttttgg 1740
gcggagggcg gtcggtaggc ggttaatggg gattttgtaa gcgggttggc ggcgcggttt   1800
atttattttc gagttgtttt gttaggtcgg cgttgcgggt tttgcgcggc gttcgttgtt   1860
tttttagtt tcgcgtttcg ggttcgttgg cgcgttttat cgcgtatatt tcgtatatat    1920
ttattcgttt tatatttacg tcggtcgggg agttagtgcg ttcgttcgga acgcgggcgt   1980
tttatttgtg atatattgtt aagttgtttt ttgattgggt tttagggaaa tacggttttt   2040
tcgtttcgag atgtgtattg ggattttagt ttgtgtcggg tacggtgttt ggtatgggaa   2100
aattatatag aataaaatag atttttttaa atttttgttt ttcggaaatt tgtattttgg   2160
tgggatagat agataataaa tatgtaagtt aattaataag gtaattttgg aggattagtt   2220
ttacgtttat tacgaaatag gttaatggaa tagagaatgg taggaaggga gcgtatttta   2280
ttagattggg tttttttgtc ggattggtgt tggagtcgag gtttgaaggt aagaaggttt   2340
gtaatttgaa gaaagggttg aggttttcga gatttaaaga agtaatagag acgtagagtt   2400
tatttgcgtt attttatatg ttattggtta ttgttgagtt gaaatgtagt tagttttaaa   2460
ttaattgtgt tgtaagtgta aaatatatat tagagtttaa g                       2501
```

<210> SEQ ID NO 50
<211> LENGTH: 4501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 50

```
tttatttgtt ttataggatt ttttatggaa ttttggagtt tttgaggcga gagggatttt     60
ggatattatt gagttttatt ttttatttaa taaatataga agtggacgtt tggataggta    120
aagtgatttg attaaggtag gtgtatagtt attttgtaat attgggaata aattttaggt    180
```

```
tttttgattt tttgttttta ttttattttt tttttatttt ttagaaataa agtttttatg    240
tgtttttttt tatagtgata tgtttggaat gtattagtta gtaatttagg aagggaaaaa    300
aataaatata taagagataa atttgttagg aggataaatt tgtattgttt ttgattggtt    360
tagagggtga ttattattat ggtagagaat tatttaatta gtgtaagtaa aatttttttg    420
tgggttgggt attgtataaa gatttaaacg aatttgttta tagatttgaa aagtagatac    480
gagatttgtg aatggttggg gtttttaagt ttatagtata agtatgggtt atattttata    540
gtttggagga ttgagttttg aaaatgggta agttttttta tttttttgaa ttttattttt    600
tttatattta aaataaggat gagtagtttt tgaggttttt tttacgattt tttttttat    660
agattttagt attttataat ttgatataaa gagggtggat atgaatttat ttttttaga    720
aaagttttag gaaagagaat attaggttat tttagtaggt gtgtagatag gttagataga    780
ttttgaaatt tatttagttt tttttagatg tataatttta ttattgtttt tagttgttaa    840
gagaaagtag gagagtttgt atttttattt tttttttttt tttttttttt tttggagacg    900
gagttttatt ttattattta ggttagagtg tagtggtatg attttagttt attgtaagtt    960
tcgtttttta ggtttacgtt attttttgt tttagttttt taagtaattg ggattatagg   1020
cgtttattat tatatttggt taattttttg tgttgttagt atagacgggg ttttattatg   1080
ttagttagga tggtttcgat tttttgattt cgtgattcgt ttattttggt tttttaaagt   1140
gttgggatta taggcgtgag ttatcgtatt tagtttgtat ttttattttt attgttagtt   1200
ttaggtttat tttatttagt ttattaagtg atgttgaata attaattttt atatattatt   1260
aggtttatgg atattatgat atttagattg atgggtgttt gttgaagggg gtgattttag   1320
taggaggatt tttttacgta aggatttatg gagtttgttg tttttttttt ttagggtgag   1380
aattaaattg tttttatacg gtgggtagag gggaattgat ttaggtttgg aataagagag   1440
aatattttaa ttgaaaagtt tttggaattc gttgaatttt aagatattgt gtggattagt   1500
ttaggatagg gagtgagaag aaattaatta aaaggtaatt tcgttatttt ttagttggaa   1560
aaaagattag attatatttg tgtttttata attaagtagt tgttggaaaa aaacgtttta   1620
gatgtttttt atgagaaaat tgttgtttga agtttagtag aagttattta tttgatattt   1680
atattttagg taaggttttt cgttggagaa aatatcggta ttttggataa aattgaaatg   1740
tgaaaagaaa gggaagagag ggtttttatt atgtaagatg tttatttaaa gtggatttgg   1800
tttggaaagt tttttaaaat tttttatatg attgtggaat aagttatgtg gggcgcgggg   1860
ataagcgaat tttttaaatt ttattacgta tgtttttatt taatttggat ttttagagtg   1920
gtttttaggg tatttttgttt aggatttagt tagttgttgg ttatatttat gtttttttagt   1980
tttttgagat tttatttggt tttgagaggg ttaaaaagta gtgtggttaa atattttagg   2040
ttttaaagta tttttattgt ggttggggaa gtaatagaat tatattttat aaaataatga   2100
aaatagtgtt agaaaaaatat cgagagatag aaatattttt acgagttagg ttatagttag   2160
agtgaaggta gggaaggttt ttaaagttgg gtggaggga taagttaaaa agatgtggaa   2220
attggttttt tttttttatg gttaaagtgt ttaaagggga aaaaggagtt ttaaaaatgt   2280
ttttggaaat attatttttt acgaattttt cggtttttgt tgttttaatg ttatttgttt   2340
gagatgtaaa tagaggagtt ttgagaaaga agttgaattt gtattttttt ttgtttttat   2400
ttgttttaaa tttgtggtat ttttaatagg atgaagcgga agagaaaggg aaagagataa   2460
aagtgtagaa agatggaaga ttttagttgt aaatggttat ttgtagttag atggaatagt   2520
tgttgacgtt tagggaaatg tatgtttttt tttagatggg aaggagtagt ggaaaggggt   2580
```

gacgagtttt tggttggtta ttaattattt tatttttttg tgtcggtttt ttatttggaa 2640
agtgggagtg atatttgtgt ttgttttttt tatttataaa gattattgtg agagttataa 2700
tacggtgaga tatagaattt tgtttttaaa aatataaagt agaattaaga tgttaataat 2760
aaggatagta attgtgttag ttatttgtaa ttatttatta tagttagtcg tttaggattt 2820
tggatcgttt ttttggtttt attatagttt tggattagtt tatttttaaa ttttttgttg 2880
aagggtggag ttttgttagt tatgggtagg gaattatttt tttttgtttt tttatttttt 2940 gtttttttaaa tatgtttagg gtttttgtat ttgttgtttt ttttgtttgg tatttttttt 3000
ttgtggtttg ttttagagtt gatttttgtt tttgtttatt ttttagcgag gatggtattt 3060
tagggagttt ttttttttatt atcgtagaga gagtaggttt tttttagtta tgtttaattt 3120
agaattttgt tttgtttttt ttatagtttt agtattatag aaaattattt tgtgtattta 3180
tggatgttta cgggggtaag ggttttgtgt tgtttaattt agtattttga atcgtgtttg 3240
ttgaatgaat atagaatttc gtttgttttg ggagagtata gaaaatagtt ttttattata 3300
tattatagtt agttgtaaat agtagatggt tttttatatt ttagagagta agaattagag 3360
agagagagaa agagagagag tttgggtttt tttttttttgt gtttgttttt tttagagaaa 3420
ttggaggggt agtagttagt atttttttcgt tggttttatt aagtatagtt aaggttttta 3480
ggatatggtt atttttttatt tgtggaagcg gttttgttgg ggtgggtggg tgttagttgg 3540
ttttggtttg ggttagagat atttagtggt ttaggtgggc gtggggttag ggcgtagacg 3600
agaaggggta cgagggtttc gtttcgagga tttagcggta agtatcggtt tcgggcgcgt 3660
tttagtttat ttattcgcgt gtttacggcg gtattatttt ttataaggat ttgaacgatt 3720
cgggggcggt ttcgtttcgt tatttttttgt tttcggtttc gttttttttt tggagggtcg 3780
atgaggtaat gcggttttgt tattggtttg agggggcggg ttttaatagt tcgaggcggg 3840
gttttcgggg gtttagcgtt atattattcg gtcgtttagg tagcggcgta gagcgggtag 3900
taggtaggcg gcgggcgttt agacggtttt tttttttttt tttgtttttt tagtttttgt 3960
tttttcgtcg ggaggtcgtt cgtcgagttt tgcgttagcg tcgaggtagt ttcgttgcgt 4020
tttatttcgt ttcgtcgggt attcggaggg tagcgcgtcg gaggttaagg ttgtttcgta 4080
cggttcggcg ggcgagcgag ttcgggttgt agtagtttcg tcggcggcgc gtacggtaat 4140
tttggagagg cgagtagtag tttcggtagc ggcggtagta gcggtaatga tttttttggtt 4200 cgggtttatc gtgtttttgg gtagttggag tttgggggat tggggcgtcg aggcgtgtat 4260
atgttcgttt agttattttt aggacgtttt ttgtaatttc gatatcggta agcgtttttg 4320
gtgtttcgtt cgagttttac gttgtagtta ggattgtagc gttgtttagg gaggtagggc 4380
gagttttatt tttttttttt gttttaggag aggggtagac ggggttgggg cggagtggag 4440
aaattcgatg tttttgggcg ggggcgttgg tatagttgag aggggaagat gttttgtaga 4500
g 4501

<210> SEQ ID NO 51
<211> LENGTH: 4501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 51
ttttgtaggg tatttttttt ttttagttat gttagcgttt tcgtttaagg atatcgagtt 60
tttttatttc gttttaattt cgtttgtttt ttttttgggg tagaggaaag gagtggggtt 120

```
cgttttgttt ttttaagtag cgttgtagtt ttggttgtag cgtggggttc gggcggggta    180
ttaggagcgt ttatcgatgt cggagttgta gaaggcgttt tgggggtggt tgggcgagta    240
tgtgtacgtt tcggcgtttt agttttttag gttttagttg tttaggagta cgatgagttc    300
gagttaaggg gttattgtcg ttgttgtcgt cgttgtcggg gttgttgttc gtttttttaa    360
agttgtcgtg cgcgtcgtcg gcggggttgt tgtagttcga gttcgttcgt tcgtcgggtc    420
gtgcggggta attttggttt tcggcgcgtt gtttttcgag tgttcggcgg gacgggatgg    480
ggcgtagcga ggttgtttcg gcgttggcgt aggattcggc gggcggtttt tcggcgaagg    540
agtaggagtt ggaggagtaa gaggaggagg agaagtcgtt tgagcgttcg tcgtttgttt    600
gttgttcgtt ttgcgtcgtt gtttgggcgg tcgagtgata tagcgttggg ttttcgggga    660
tttcgtttcg ggttgttggg gttcgttttt ttagattaat ggtagagtcg tattatttta    720
tcggtttttt aaaaaggggg cggggtcggg ggtaaggggt aacggggcgg ggtcgttttc    780
ggatcgttta gatttttata gggaataatg tcgtcgtggg tacgcgagtg ggtgggttgg    840
ggcgcgttcg ggatcggtgt ttgtcgttgg gttttcggag cggagttttc gtgttttttt    900
tcgtttgcgt tttggtttta cgtttatttg ggttattggg tgtttttgat ttaaattaga    960
attaattaat atttatttat tttagtagga tcgtttttat aggtgagggg tggttatgtt   1020
ttagagattt tgattgtgtt tggtggaatt agcgggggaa tgttaattgt tattttttta   1080
gttttttggg agagagtagg tatagaggag aaagatttaa attttttttt ttttttttt    1140
tttttggttt ttattttttg ggatatggga agttatttgt tgtttgtagt tggttatgat   1200
atatgataga agattgtttt ttgtgttttt ttagagtaaa cggggttttg tatttattta   1260
ataaatacgg tttaggatgt tgggttaagt aatataaagt tttgttttc gtggatattt    1320
atgaatgtat agggtgattt tttgtgatgt tagggttatg aagaaaataa aatagagttt   1380
tgggttggat atgattgggg agggtttgtt ttttttgcga tagtaaggga agggtttttt   1440
gaagtgttat tttcgttgag aagtggataa agataaggat tagttttggg gtaagttata   1500
ggagagaggt attaggtagg gggaatagta agtgtaaaga ttttgggtat gtttgaaaga   1560
tagaaagtag aaaggtaaga ggaagtggtt ttttgtttat ggttgataga gttttatttt   1620
ttagtaaggg atttgggggt gagttgattt aaaattgtag taaaattagg agaacgattt   1680
aggattttag acgattagtt ataatagatg attgtagata attaatataa ttattatttt   1740
tattattgat attttgattt tgttttgtat ttttaaaagt aggattttgt attttatcgt   1800
attatagttt ttataataat ttttgtgggt aggaaaagta agtataagta ttatttttat   1860
tttttagatg aggaatcggt atagaaagat gggatgattg gtggttagtt aggaattcgt   1920
tatttttttt tattgttttt ttttatttga agagagatat gtattttttt gaacgttagt   1980
agttgtttta tttaattgta aatggttatt tgtagttggg atttttttatt tttttatatt  2040
tttgtttttt tttttttttt tttcgtttta ttttgttaga aatgttataa gtttggaata   2100
aatagaaata gggagaaatg taagtttagt tttttttttta gaattttttt gtttatattt  2160
tagataagtg atattgggat agtagaggtc gaagaattcg tgagagatgg tatttttaag   2220
aatattttttg aaattttttt tttttttttg agtattttag ttataggaaa gggaaattag  2280
tttttatatt tttttgattt gttttttttta tttagtttta aaaatttttt ttgtttttat  2340
tttaattgtg gtttaattcg tagagatgtt tttgtttttc gatgtttttt tagtattgtt   2400
tttattgttt tatggggtat gattttattg ttttttttaat tatagtagga atattttgag  2460
gtttgggata tttagttata ttgtttttta gtttttttag aattaaatag ggttttagga   2520
```

```
gattggagag tatgggtgtg gttaatagtt gattgagttt tgagtagagt gttttggagg   2580

ttattttaag gatttaggtt gaatgagggt atacgtggtg gaatttgaga gattcgttta   2640

ttttcgcgtt ttatatgatt tattttatag ttatgtggaa ggttttagaa gatttttttag  2700

attaaattta ttttggataa gtattttata tgatagaggt ttttttttt ttttttttt   2760

atattttagt tttgtttaaa gtgtcgatat tttttttaac ggaaggtttt gtttggaata   2820

taagtattaa gtagataatt tttgttgaat tttaagtagt agtttttttta tagaaagtat  2880

ttgaagcgtt ttttttagt agttatttaa ttatgaaagt ataagtataa tttgattttt   2940

tttttagttg aaaagtaacg aaattatttt ttggttaatt tttttttatt ttttatttta   3000

agttggttta tatagtgttt tgaagtttag cgaattttaa gagtttttta gttgggatgt   3060

ttttttttat tttaaatttg agttagtttt tttttgttta tcgtgtgaag gtagtttggt   3120

ttttatttta aggaaaagaa atagtaaatt ttatgaattt ttgcgtaggg gagttttttt   3180

gttagggtta tttttttttag taggtattta ttagtttgga tgttatggtg tttatgagtt  3240

taataatatg taagaattgg ttatttaata ttatttaata agttaggtgg ggtgaatttg   3300

aggttaatag taagaatgaa gatgtaggtt gggtgcggtg gtttacgttt gtaattttag   3360

tattttgaga ggttaaggtg ggcggattac gaggttagga gatcgagatt attttggtta   3420

atatggtgaa atttcgtttg tattaataat ataaaaaatt agttaggtgt ggtggtgggc   3480

gtttgtagtt ttagttattt gggaggttga ggtaggagaa tggcgtgaat ttgggaggcg   3540

gagtttgtag tgagttgaga ttatgttatt gtattttagt ttaggtgatg gagtgagatt   3600

tcgtttttaa aaaaaaaaaa aaaaaaaaaa agaatgaaga tgtaggtttt tttgtttttt   3660

tttgatagtt aagaataatg atagagttat atatttggga agaattgagt aagttttaag   3720

atttatttgg tttgtttata tatttattag gatgatttgg tattttttttt tttggaattt  3780

ttttaggaaa ggtgagttta tatttatttt ttttgtatta agttatagga tgttagagtt   3840

tgtaggaaga gaagtcgtaa aaaggatttt agaaattatt tatttttgtt ttaaatgtgg   3900

gaaaaataag gtttagagaa gtgaaggaat ttgtttattt ttagggttta gttttttaag   3960

ttgtaaggtg tggtttatgt ttgtattgtg ggtttggaaa ttttagttat ttatagattt   4020

cgtatttgtt ttttagattt gtagatagat tcgtttgagt ttttgtatag tgtttagttt   4080

atagagaaat tttatttata ttgattaaat aattttttat tatgataata attatttttt   4140

gagttaatta gaagtaatat aggtttgttt ttttgatagg tttatttttt gtgtgtttat   4200

ttttttttt ttttaaatta ttagttaatg tattttaaat atattattat aaaaaaaagt   4260

atatgaaaat tttgtttttg ggaaatgaaa agagagtaaa gtggaaataa aaaattaaaa   4320

gatttgagat ttgtttttaa tgttgtagaa tagttgtgta tttgttttgg ttaagttatt   4380

ttgtttgttt aggcgtttat ttttgtgttt attggatgaa agatagaatt tagtggtatt   4440

taggattttt ttcgttttaa aaattttaag attttatggg gaattttgta ggataagtga   4500

a                                                                   4501
```

<210> SEQ ID NO 52
<211> LENGTH: 3001
<212> TYPE: DNA
<213> ORGANISM: Artificial Sequence
<220> FEATURE:
<223> OTHER INFORMATION: chemically treated genomic DNA (Homo sapiens)

<400> SEQUENCE: 52

```
gaagtgttaa tgttagattt ttatttatta tataagttta tttttgtatt agggtagtga     60
```

```
tttttttttt tgggtgagat tttgaaattt gggattataa ttttgaatta taattataaa    120
atggtatttg gttgtaaatt attttttttt tttttttgtt ttttatagtt gatattatgg    180
atttttataa ggatttatgt tttttattta ttttaatgaa tagttgttgg gtaataattt    240
tagaagagtt ttaattttta ttaggagaat ggataaggtg gagaagtaga gaaaatgtaa    300
tgagtagaat gtttaagtta ttattttgga attgattgaa tataaataaa aatgagaaag    360
atacgtaaaa aagaagggaa tgggtaagta gggtgatgtt tgggagagga ggggttttat    420
agttatgaga gttaattttg taatatttta tagggttata atattgtttt ttatatattg    480
aggtagtagt agggaaattt tttaattatt agaaatattg aattttgttt tttattttta    540
aatatttttt ttatttagtt tttgtttttt tttattttttg taatttttat tgttttaaaa    600
atgatttttt ttttttcgga agaagtaatt ttttaaattt agtttatata aggggatttg    660
atatgtttaa taagttttaa atatattgta tttagtaata tttattatat gtttattttg    720
agttttgagt aatttgtatt ttaagtttag tttttattgt tttgtttttg gtaaattttt    780
attaagtgtt tttttttttt aaatatacgt atatgtttat tagattttaa agtttttttat    840
gaatatgtaa attttttttt tttgaaaatt tttgcgtgag tggttagtag gttaatttat    900
ttattgtaat gtggttttgt gttagggttt tgttttcgtg ttgtttgtaa gataattata    960
gatgtgattg tattttagaa gtttttgaat tttttaagat agtttggttt ataagaaaat   1020
taaaaggtgg aggtcgggcg cggtggttta cgtttgtaat tttagtattt tgggaggtcg   1080
aggcgggcgg attatttgag gttgggagtt cgaaattagt ttgattaata tggggaaatt   1140
tcgtttttgt taaaaatata aaattagtta ggcgtggtgg tgtatgtttg taattttagt   1200
tattcgggag gttgaggtag gagaatcgtt tgaattcggg aggtagaggt tgcgatgagt   1260
cgagatcgtg ttattgtatt ttagtttggg taataagagc gaaattttgt tatatatata   1320
taaatatata tatatatata tatacggtgt agtttaggaa gtaaaaaaaa aaaaaaaaaa   1380
aaaattagat ttttttttat attttagatt tgaaggtata aattttaggg ttagggcgtt   1440
cgtttattta attttatatg tatttgtagg ttatttagta tttaggtatt tagtatttag   1500
gtatattgtg gtttttttatt ttttacgata gtagtaataa cgttgattgg aagtttatta   1560
ttgtgtgtta cgggttatgg gttatgtgtg ttagaatttt atgtgaaatt aatatttaat   1620
ttttacggat atttttgaaa tagatgttat agtttttatt ttgttaacga ggtagttgag   1680
gtttttagag gtttaatatt agtattatga gtcgtagtac gtaaggtaaa tatagtcgga   1740
ggtgagtata tatttgtttc gtattttatg cgtttaatta taaggttttt tttttttagg   1800
aaggtcgttg ttttttttgg gacgatttgt tagttttgag gtatgatagt acgggttttt   1860
agaagggtga ttaggaggtt tttttcgttt tagttgtcgg cgtcgtcgtt tattgtaggg   1920
ttcgggttgt gattcgtggg gacggttttt tgcgtttcgg cgggggaggt gggcggggag   1980
gggcggcggg gcgtcggggc ggggttcggg acggtcgggt tgggagttgg agtttatagc   2040
gggaagcggt cgtcgttcgg gtttcgtagg gttaggcgag gcgagggggg gcggggtcgg   2100
gcgttacggg aaggggaggt cgcgcggatc gggagtcgta tcgcgttagt cgggttgtag   2160
cggtcgcgta ttaaggttgc gatggggttg gagacggaga aggcggacgt atagtttttt   2220
atggacgacg atttttatag ttattatagc ggtttcgagt acgtcgattt cgagaagttc   2280
gcggattcgg attaggatcg ggatttttat cggtttaatt cgtattttaa ggtgaagttc   2340
ggggcgggcg ggtttaagtt ttcgttgagg tcgggaggtg cgggcgtttt ttagtttcgt   2400
tttaattcgt tttattattg ttatcgggtc ggtttcgtag ggtttgagat tcgtattttt   2460
```

```
tttcggtttt attcgttatt aggtcgttcg cgtagttagg aatttttagt taggtttttg   2520

tgcgtttatc gtgattttaa gagaagaggc ggacgttttg gtacgttttt tttttttgtt   2580

tttttcgttt aaagcgtttt cggttttcgg ggcgttaggt tggttgatag ttcggggttt   2640

ttgcgttttg tttttttagt tgggtttcga ggatgtgatc gtagagtcgg tgattacgta   2700

tttttttgat aaagtgtgga tttgtagtta tgtttttttt gaaattagta aatacgtaat   2760

gtataagttt ttgacggtgt ttttggttat ttttttggtt tttattgcgg gaattttttt   2820

tgttattttt agttgtttgt atatttggtg agacggggta tatcgggtgg atcggttttt   2880

tgaaatatgg gtatattttt cgttatttgt tttttatttt ttttttattt taggtcggcg   2940

ttaggaggag gaacgcgtat tagtttttaa gtagtaggaa gaattggaag gttttgaaag   3000

g                                                                   3001
```

<210> SEQ ID NO 53
<211> LENGTH: 3001
<212> TYPE: DNA
<213> ORGANISM: Artificial Sequence
<220> FEATURE:
<223> OTHER INFORMATION: chemically treated genomic DNA (Homo sapiens)

<400> SEQUENCE: 53

```
ttttttaagg tttttttagtt tttttattg tttgggaatt gatgcgcgtt tttttttttg     60

acgtcggttt gggataagag gagagtaggg ggtaggtggc ggagaatatg tttatgtttt    120

agaaagtcgg tttattcggt gtgtttcgtt ttattagatg tgtagatagt tgagggtggt    180

aaagagaatt ttcgtaatga aggttagggg aatggttagg aatatcgtta ggaatttgta    240

tattacgtat ttgttgattt taaagagggt atggttgtag atttatattt tgttaaagga    300

gtgcgtagtt atcggttttg cgattatatt ttcgaagttt agttgaggag ataggacgta    360

gggatttcga attgttagtt aatttgacgt ttcgggaatc gggagcgttt tgggcggggg    420

aagtaggagg gaaggacgtg ttagggcgtt cgtttttttt tttagggtta cggtgggcgt    480

ataggaattt ggttaagaat ttttggttac gcgggcggtt tggtgacggg tgggatcggg    540

gaagggtgcg ggttttagat tttgcggggt cgattcggta gtaatggtgg gacgggttag    600

ggcggggttg aggggcgttc gtatttttcg gttttagcgg ggatttgggt tcgttcgttt    660

cgggttttat tttgagatgc gagttgagtc ggtggggatt tcggttttgg ttcgagttcg    720

cgaatttttc ggggtcggcg tattcgaggt cgttgtggtg gttgtaggag tcgtcgttta    780

tgaagagttg tacgttcgtt tttttcgttt ttagttttat cgtagttttg gtgcgcggtc    840

gttgtagttc ggttggcgcg gtgcggtttt cggttcgcgc ggtttttttt tttcgtagcg    900

ttcggtttcg tttttttttcg tttcgtttag ttttgcgagg ttcgggcggc ggtcgttttt    960

cgttgtgggt tttagttttt agttcggtcg tttcgagttt cgtttcggcg tttcgtcgtt   1020

tttttcgtt tattttttttc gtcggggcgt agggaatcgt ttttacgagt tatagttcgg   1080

gttttgtagt gggcggcgac gtcggtagtt gggacgagga gggtttttttg gttatttttt   1140

tgggggttcg tattgttatg ttttagagtt ggtaagtcgt tttagggaag ataacggttt   1200

ttttggaggg agggaatttt gtggttaggc gtatggggtg cgaagtaggt atgtgtttat   1260

tttcggttgt gtttgttttg cgtgttgcgg tttatggtgt tggtattgag tttttgggaa   1320

ttttagttgt ttcgttggta aaatgggggt tgtggtattt gttttagggg tgttcgtgag   1380

aattaaatgt taattttata taaaatttta atatatatgg tttatggttc gtaatatata   1440

gtgataaatt tttaattaac gttgttgttg ttgtcgtgag aggtaaggag ttataatgta   1500
```

tttgagtgtt aggtatttga gtgttaggtg atttgtaagt gtatgtggag ttgggtaggc 1560
gaacgttttg gttttagagt ttgtgttttt agatttgagg tgtgagggga gatttgattt 1620
tttttttttt ttttttttta tttttaaat tatatcgtgt gtgtgtgtgt gtgtgtgttt 1680
gtgtgtgtgt ggtagagttt cgtttttgtt gtttaggttg gagtgtaatg gtacgatttc 1740
ggtttatcgt aatttttgtt tttcgggttt aagcgatttt tttgttttag tttttcgagt 1800
agttgggatt ataggtatgt attattacgt ttggttaatt ttgtattttt agtagagacg 1860
gggttttttt atgttggtta ggttggtttc gaatttttaa ttttaggtga ttcgttcgtt 1920
tcggtttttt aaagtgttgg gattgtaggc gtgagttatc gcgttcgatt tttatttttt 1980
aatttttttg tgaattagat tgttttgaaa gatttaggaa tttttaagat gtagttatat 2040
ttgtgattat tttgtaggta gtacggaaat agaattttaa tataaagtta tattgtaatg 2100
gatgaattag tttgttgatt atttacgtaa aggtttttag aagggaggag tttgtatgtt 2160
tataaagggt tttagggttt ggtagatata tacgtgtgtt tggggaggaa gggtatttag 2220
tgaaaatttg ttaaaagtaa aataatgaga attaggtttg aggtgtaggt tgtttagagt 2280
ttaaagtagg tatgtagtag gtattgttgg atatagtgta tttggagttt gttgaatata 2340
ttaaattttt ttatgtgaat tggatttgaa gaattgtttt tttcgaaaga aaaaagatta 2400
tttttgaaat agtaaaaatt atagaaataa aaaagaatag gaattgaatg agaaaaatgt 2460
ttgggggtgg gaggtaaagt ttaatatttt taataattaa aaagtttttt tgttgttatt 2520
ttagtatatg aagggtagtg ttgtaatttt atagggtgtt atagagttga tttttatggt 2580
tatggagttt tttttttttt agatattatt ttgtttattt attttttttt tttttacgta 2640 tttttttat ttttatttat gtttagttaa ttttaaagtg atgatttaga tattttattt 2700
attgtatttt ttttgttttt ttattttgtt tattttttg atgagaattg gaattttttt 2760
agaattgttg tttaataatt gtttattaaa gtgaatagaa gatatgaatt tttatgggaa 2820
tttataatat taattgtgag gaatagaaaa aaaaaggaga taatttatag ttaaatatta 2880
ttttataatt ataatttaaa attataattt tagattttaa ggttttattt aaagaagaaa 2940
gttattgttt tagtataaga gtgggtttat gtagtgggta aaaatttgat attagtattt 3000
t 3001

<210> SEQ ID NO 54
<211> LENGTH: 2501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 54
tttggatttt aatgtgtatt ttatatttat agtataatta atttgggatt agttatattt 60
tagtttaata atagttaata gtatatggga tagtgtaaat aaattttgtg tttttgttgt 120
ttttttgggt tttggagatt ttaatttttt ttttagattg taaatttttt tgtttttaag 180
ttttggtttt aatattagtt tggtagagga atttagttta atgaggtatg tttttttttt 240
gttatttttt attttattaa tttgttttgt ggtaaatgta ggattgattt tttaaaatta 300
ttttattaat tagtttatat atttattatt tatttgtttt attagaatgt aggtttttgg 360
aaggtaggga tttaaaaaaa tttgttttgt tttatgtgat ttttttatat taagtattgt 420
gtttggtata agttgggatt ttagtatata ttttgggatg gaagaattgt gttttttttag 480 aatttagtta gagggtagtt tagtaatgtg ttataggtgg ggtgtttgtg ttttgggtgg 540

```
atgtattggt tttttggttg gtgtgggtgt ggggtgagtg ggtgtgtgtg gggtgtgtgt    600

ggtagagtgt gttagtgagt ttggagtgtg gagttgggag gagtagtgag tgttgtgtag    660

aatttgtagt gttggtttgg tagggtagtt tggaggtggg tgggttgtgt tgttagtttg    720

tttgtagggt ttttattggt tgtttgttgg ttgtttttg tttaaaaggt ggtaaggagt    780

tgagaggttg ttttggagtg tgaggaggat agttggattg agttaatgtt ggggattttg    840

ttttttttgt ggaggggatt tggtaatttg tagtggtagg gtttggggtt ggtgtttggg    900

agggatttgt gttttttatt tattttttag ttgtgtttt gttgttgttt tggttagttt    960

ttggtgttgg tgtttatggt tggtttttga tagtgttttg gagggattgg gggagttttt   1020

aggtgtttgg gtgagtagtt aggtgtggtt ttttggtttt tttgattttt ggtgttagtt   1080

tttgtttttt tagttagggt gtggtggggt ttgtttgggt agtgttttga gtaattggga   1140

aggttaaggt ggagggaaat ttggttttgg ggagaagtgt gattgtagtt gggaggtttt   1200

tttagttttg tgggttgggt gagaataggt ggtgttggtt tgattaggtg ttttgtgttg   1260

gggtgtgagg atttggagtg aattgttgtg ttttggtggg ttgttttttt ttttttttg   1320

tttttttggg tggttgtatg ttgggttggt tgggtaatgg agagggagtt gttaggaatg   1380

tggttttggg gattgttttg tttggggaag gggagagggt ggttatggtg ttaggagagg   1440

tgtgggagtt gagaggtggt gtgggggtgt tattgttgtt gtaggttgga gagagattgt   1500

ttttagtgag gtgtgtattg tttgggtgag ggttttattt ttttgtggtg tttttggagg   1560

tgggaaagtt gggtgggtat gtgtgtagag aaaggggagg tggggaggtt agttattttt   1620

ggagttggtt ttgattttaa tagattgttt agtgtttggg gatgttgatt ttggggtgtt   1680

gtggtgtttg gttttatgtg tgtgtggggt tgaggggttg ggggtgtttt tggttgttta   1740

gttttaataa agggtgtttt tttttatttt gtgaggaggg gtagttttgg agatttggtt   1800

tttagtgagt ggggttttag tgttggggag gtttattttt ttttggggtt gttattttat   1860

tattattatt gttttttttt tttttttaaa aggattggag attgatgtat gagggggtta   1920

tggaggtgta ggagtggtgg tgatggtttg ggaagtggag ttgaagtgtt ttgggttttg   1980

gtgaggtgtg atagtttatt atgattgtgt ttaggtagga aaatgtggat gattattatg   2040

atattggtga ggaatttggt aggtaaaggg ggtattagaa gtgtattttt ttggattgtg   2100

gaaatgtata atgatggggt tattgggtgg taaataaatg tagtttgaat taggtgtttt   2160

ttttgttttt tttggagatg tgtaaattat agagaaaaga gttattaatt tagtggtaaa   2220

ttgtttgatt taagggtttg ggggtggagg agaggtagta gtttagggtt agattatgat   2280

gtatagtata ttgatttagt tttttggata aaattagatt taattgtttg tgttaatttt   2340

tgttagtttt tgttttttttg tgataatagg ataaatatta agattataat tgtaattgga   2400

gttagttttt atgtgtgatt taaatggagg gtataaatta attaataggt tttaaaaatt   2460

ttagtatttt atttttttatt taaattttta gtgtaatttg a                      2501
```

<210> SEQ ID NO 55
<211> LENGTH: 2501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 55

```
ttaaattata ttgaaaattt agatagaggg taaagtatta agatttttaa aatttattaa     60

ttagtttgta tttttttgttt aaattatata taaaagttaa ttttaattgt aattataatt    120
```

```
ttagtgtttg ttttgttgtt atagaagggt aagggttgat aagagttagt atggataatt    180
aaatttgatt ttgtttaggg gattggatta atatattgtg tattataatt tagttttgaa    240
ttgttgtttt ttttttattt ttaggttttt ggattaggtg gtttattgtt gggttagtaa    300
tttttttttt tatgatttgt gtatttttag aaagggtgag ggagatgttt gatttaaatt    360
gtatttgttt attatttaat ggttttattg ttatgtattt ttataattta ggagggtatg    420
tttttggtat ttttttattt tgttaagttt tttgttggtg ttgtagtaat tatttatgtt    480
tttttgtttg aatatggtta tgataaattg ttatgtttta ttaaagttta gggtatttta    540
gttttgtttt ttagattatt attattgttt ttgtgttttt gtagtttttt tatgtattag    600
tttttagttt ttttgaagaa aaaaaaaagg taataataat agtaaaatgg taattttaaa    660
aggaagtaga tttttttggt gttaagattt tgtttgttga agattgggtt tttggagttg    720
tttttttttg tggggtggag aggagtattt tttgttaaag ttgggtggtt agggatgttt    780
ttgatttttt agttttgtgt gtgtgtgggg ttgggtatta tggtattttg aggttggtgt    840
ttttaaatgt tgggtggttt gttgggatta gaattggttt tggaagtgat tggttttttt    900
gttttttttt tttttgtata tatgtttatt tagttttttt atttttaggg atgttgtgga    960
agaatgaagt ttttgtttag atggtatgtg ttttattggg agtaattttt ttttagtttg   1020
tggtaatggt ggtatttttg tgttattttt tggtttttgt gtttttttta atattgtggt   1080
tatttttttt ttttttttga gtgaggtagt ttttagagtt atatttttgg tgattttttt   1140
tttgttattt ggttgatttg gtgtgtggtt gtttgggggga gtaagggagg gaagggagtg   1200
gtttattgag gtgtagtagt ttgttttaga tttttgtgtt ttgatataaa gtgtttggtt   1260
gggttggtgt tatttgtttt tatttggttt gtggggttgg ggaagttttt tggttgtgat   1320
tgtatttttt tttgaagtta agtttttttt tgttttggtt tttttagttg tttgaggtat   1380
tgtttggata aattttattg tgttttggtt gggaaagtaa aagttggtgt tgggggttgg   1440
ggggattggg gagttgtgtt tggttattta tttgggtgtt tgggagtttt tttggttttt   1500
ttggagtgtt gttggaggtt gattataggt gttagtgttg gagattagtt ggggtggtgg   1560
tgggaatata gttagggagt gagtgggggg tgtagatttt ttttaggtgt tggttttaga   1620
ttttgttgtt gtgagttgtt gagttttttt tgtggaggga ataaagtttt tggtgttggt   1680
ttggtttggt tgtttttttt atattttgaa gtagtttttt ggttttttgt tgttttttgg   1740
gtggagggtg gttggtaggt ggttaatggg gattttgtaa gtgggttggt ggtgtggttt   1800
atttattttt gagttgtttt gttaggttgg tgttgtgggt tttgtgtggt gtttgttgtt   1860
tttttttagtt ttgtgttttg ggtttgttgg tgtgttttat tgtgtatatt ttgtatatat   1920
ttatttgttt tatatttatg ttggttgggg agttagtgtg tttgtttgga atgtgggtgt   1980
tttatttgtg atatattgtt aagttgtttt ttgattgggt tttagggaaa tatggttttt   2040
ttgttttgag atgtgtattg ggattttagt ttgtgttggg tatggtgttt ggtatgggaa   2100
aattatatag aataaaatag atttttttaa atttttgttt tttggaaatt tgtattttgg   2160
tgggatagat agataataaa tatgtaagtt aattaataag gtaattttgg aggattagtt   2220
ttatgtttat tatgaaatag gttaatggaa tagagaatgg taggaaggga gtgtatttta   2280
ttagattggg tttttttgtt ggattggtgt tggagttgag gtttgaaggt aagaaggttt   2340
gtaatttgaa gaaagggttg aggtttttga gatttaaaga agtaatagag atgtagagtt   2400
tatttgtgtt attttatatg ttattggtta ttgttgagtt gaaatgtagt tagttttaaa   2460
ttaattgtgt tgtaagtgta aaatatatat tagagtttaa g                       2501
```

<210> SEQ ID NO 56
<211> LENGTH: 4501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 56

```
tttatttgtt ttataggatt ttttatggaa ttttggagtt tttgaggtga gagggatttt     60
ggatattatt gagttttatt ttttatttaa taaatataga agtggatgtt tggataggta    120
aagtgatttg attaaggtag gtgtatagtt attttgtaat attgggaata aattttaggt    180
tttttgattt tttgttttta ttttattttt tttttatttt ttagaaataa agtttttatg    240
tgtttttttt tatagtgata tgtttggaat gtattagtta gtaatttagg aagggaaaaa    300
aataaatata taagagataa atttgttagg aggataaatt tgtattgttt ttgattggtt    360
tagagggtga ttattattat ggtagagaat tatttaatta gtgtaagtaa aattttttg     420
tgggttgggt attgtataaa gatttaaatg aatttgttta tagatttgaa aagtagatat    480
gagatttgtg aatggttggg gtttttaagt ttatagtata agtatgggtt atattttata    540
gtttggagga ttgagttttg aaaatgggta agttttttta tttttttgaa ttttattttt    600
tttatattta aaataaggat gagtagtttt tgaggttttt tttatgattt tttttttat     660
agattttagt attttataat ttgatataaa gagggtggat atgaatttat tttttttaga    720
aaagttttag gaaagagaat attaggttat tttagtaggt gtgtagatag gttagataga    780
ttttgaaatt tatttagttt tttttagatg tataatttta ttattgtttt tagttgttaa    840
gagaaagtag gagagtttgt atttttattt tttttttttt tttttttttt tttggagatg    900
gagttttatt ttattattta ggttagagtg tagtggtatg attttagttt attgtaagtt    960
ttgtttttta ggtttatgtt attttttttgt tttagttttt taagtaattg ggattatagg   1020
tgtttattat tatatttggt taattttttg tgttgttagt atagatgggg ttttattatg   1080
ttagttagga tggttttgat tttttgattt tgtgatttgt ttattttggt tttttaaagt   1140
gttgggatta taggtgtgag ttattgtatt tagtttgtat ttttattttt attgttagtt   1200
ttaggtttat tttatttagt ttattaagtg atgttgaata attaattttt atatattatt   1260
aggtttatgg atattatgat atttagattg atgggtgttt gttgaagggg gtgattttag   1320
taggaggatt tttttatgta aggatttatg gagtttgttg tttttttttt ttagggtgag   1380
aattaaattg tttttatatg gtgggtagag gggaattgat ttaggtttgg aataagagag   1440
aatattttaa ttgaaaagtt tttggaattt gttgaatttt aagatattgt gtggattagt   1500
ttaggatagg gagtgagaag aaattaatta aaaggtaatt ttgttatttt ttagttggaa   1560
aaaagattag attatatttg tgtttttata attaagtagt tgttggaaaa aaatgtttta   1620
gatgtttttt atgagaaaat tgttgtttga agtttagtag aagttattta tttgatattt   1680
atattttagg taaggttttt tgttggagaa aatattggta ttttggataa aattgaaatg   1740
tgaaaagaaa gggaagagag ggtttttatt atgtaagatg tttatttaaa gtggatttgg   1800
tttggaaagt tttttaaaat tttttatatg attgtggaat aagttatgtg gggtgtgggg   1860
ataagtgaat tttttaaatt ttattatgta tgtttttatt taatttggat ttttagagtg   1920
gtttttaggg tattttgttt aggatttagt tagttgttgg ttatatttat gtttttttagt  1980
tttttgagat tttatttggt tttgagaggg ttaaaaagta gtgtggttaa atattttagg   2040
ttttaaagta tttttattgt ggttggggaa gtaatagaat tatattttat aaaataatga   2100
```

```
aaatagtgtt agaaaaatat tgagagatag aaatattttt atgagttagg ttatagttag   2160
agtgaaggta gggaaggttt ttaaagttgg gtggagggga taagttaaaa agatgtggaa   2220
attggttttt ttttttatg gttaaagtgt ttaaagggga aaaaggagtt ttaaaaatgt   2280
ttttggaaat attatttttt atgaattttt tggtttttgt tgttttaatg ttatttgttt   2340
gagatgtaaa tagaggagtt ttgagaaaga agttgaattt gtattttttt ttgtttttat   2400
ttgttttaaa tttgtggtat ttttaatagg atgaagtgga agagaaaggg aaagagataa   2460
aagtgtagaa agatggaaga ttttagttgt aaatggttat ttgtagttag atggaatagt   2520
tgttgatgtt tagggaaatg tatgtttttt tttagatggg aaggagtagt ggaaaggggt   2580
gatgagtttt tggttggtta ttaattattt tattttttttg tgttggtttt ttatttggaa   2640
agtgggagtg atatttgtgt ttgttttttt tatttataaa gattattgtg agagttataa   2700
tatggtgaga tatagaattt tgtttttaaa aatataaagt agaattaaga tgttaataat   2760
aaggatagta attgtgttag ttatttgtaa ttatttatta tagttagttg tttaggattt   2820
tggattgttt ttttggtttt attatagttt tggattagtt tatttttaaa tttttttgttg   2880
aagggtggag ttttgttagt tatgggtagg gaattatttt tttttgtttt tttatttttt   2940
gtttttttaaa tatgtttagg gtttttgtat ttgttgtttt ttttgtttgg tatttttttt   3000
ttgtggtttg ttttagagtt gatttttgtt tttgtttatt ttttagtgag gatggtattt   3060
tagggagttt ttttttttatt attgtagaga gagtaggttt tttttagtta tgtttaattt   3120
agaatttgt tttgtttttt ttatagtttt agtattatag aaaattattt tgtgtattta   3180
tggatgttta tgggggtaag ggttttgtgt tgtttaattt agtattttga attgtgtttg   3240
ttgaatgaat atagaatttt gtttgttttg ggagagtata gaaaatagtt ttttattata   3300
tattatagtt agttgtaaat agtagatggt tttttatatt ttagagagta agaattagag   3360
agagagagaa agagagagag tttgggtttt ttttttttgt gtttgttttt tttagagaaa   3420
ttggaggggt agtagttagt atttttttgt tggttttatt aagtatagtt aaggttttta   3480
ggatatggtt atttttttatt tgtggaagtg gttttgttgg ggtgggtggg tgttagttgg   3540
ttttggtttg ggttagagat atttagtggt ttaggtgggt gtggggttag ggtgtagatg   3600
agaaggggta tgagggtttt gttttgagga tttagtggta agtattggtt ttgggtgtgt   3660
tttagtttat ttatttgtgt gtttatggtg gtattatttt ttataaggat ttgaatgatt   3720
tgggggtggt tttgttttgt tattttttgt ttttggtttt gttttttttt tggagggttg   3780
atgaggtaat gtggttttgt tattggtttg agggggtggg ttttaatagt ttgaggtggg   3840
gtttttgggg gtttagtgtt atattatttg gttgtttagg tagtggtgta gagtgggtag   3900
taggtaggtg gtgggtgttt agatggtttt tttttttttt tttgtttttt tagtttttgt   3960
ttttttgttg ggaggttgtt tgttgagttt tgtgttagtg ttgaggtagt tttgttgtgt   4020
tttattttgt tttgttgggt atttggaggg tagtgtgttg gaggttaagg ttgttttgta   4080
tggtttggtg ggtgagtgag tttgggttgt agtagttttg ttggtggtgt gtatggtaat   4140
tttggagagg tgagtagtag ttttggtagt ggtggtagta gtggtaatga ttttttggtt   4200
tgggtttatt gtgtttttgg gtagttggag tttgggggat tggggtgttg aggtgtgtat   4260
atgtttgttt agttattttt aggatgtttt ttgtaatttt gatattggta agtgtttttg   4320
gtgttttgtt tgagttttat gttgtagtta ggattgtagt gttgtttagg gaggtagggt   4380
gagttttatt tttttttttt gttttaggag aggggtagat ggggttgggg tggagtggag   4440
aaatttgatg tttttgggtg ggggtgttgg tatagttgag aggggaagat gttttgtaga   4500
```

g 4501

<210> SEQ ID NO 57
<211> LENGTH: 4501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 57
ttttgtaggg tattttttt ttttagttat gttagtgttt ttgtttaagg atattgagtt 60
tttttatttt gttttaattt tgtttgtttt ttttttgggg tagaggaaag gagtggggtt 120
tgttttgttt ttttaagtag tgttgtagtt ttggttgtag tgtggggttt gggtggggta 180
ttaggagtgt ttattgatgt tggagttgta gaaggtgttt tgggggtggt tgggtgagta 240
tgtgtatgtt ttggtgtttt agttttttag gttttagttg tttaggagta tgatgagttt 300
gagttaaggg gttattgttg ttgttgttgt tgttgttggg gttgttgttt gttttttaa 360 agttgttgtg tgtgttgttg gtggggttgt tgtagtttga gtttgtttgt ttgttgggtt 420
gtgtggggta attttggttt ttggtgtgtt gttttttgag tgtttggtgg gatgggatgg 480
ggtgtagtga ggttgttttg gtgttggtgt aggatttggt gggtggtttt ttggtgaagg 540
agtaggagtt ggaggagtaa gaggaggagg agaagttgtt tgagtgtttg ttgtttgttt 600
gttgtttgtt ttgtgttgtt gtttgggtgg ttgagtgata tagtgttggg tttttgggga 660
ttttgttttg ggttgttggg gtttgttttt ttagattaat ggtagagttg tattatttta 720
ttggtttttt aaaaaggggg tggggttggg ggtaaggggt aatggggtgg ggttgttttt 780
ggattgttta gatttttata gggaataatg ttgttgtggg tatgtgagtg ggtgggttgg 840
ggtgtgtttg ggattggtgt ttgttgttgg gtttttggag tggagttttt gtgtttttt 900 ttgtttgtgt tttggtttta tgtttatttg ggttattggg tgtttttgat ttaaattaga 960
attaattaat atttatttat tttagtagga ttgtttttat aggtgagggg tggttatgtt 1020
ttagagattt tgattgtgtt tggtggaatt agtgggggaa tgttaattgt tattttttta 1080 gttttttttgg agagagtagg tatagaggag aaagatttaa attttttttt ttttttttt 1140 tttttggttt ttattttttg ggatatggga agttatttgt tgtttgtagt tggttatgat 1200
atatgataga agattgtttt ttgtgttttt ttagagtaaa tggggttttg tatttattta 1260
ataaatatgg tttaggatgt tgggttaagt aatataaagt ttttgttttt gtggatattt 1320
atgaatgtat agggtgattt tttgtgatgt tagggttatg aagaaaataa aatagagttt 1380
tgggttggat atgattgggg agggtttgtt ttttttgtga tagtaaggga agggtttttt 1440
gaagtgttat ttttgttgag aagtggataa agataaggat tagttttggg gtaagttata 1500
ggagagaggt attaggtagg gggaatagta agtgtaaaga ttttgggtat gtttgaaaga 1560
tagaaagtag aaaggtaaga ggaagtggtt ttttgtttat ggttgataga gttttatttt 1620
ttagtaaggg atttgggggt gagttgattt aaaattgtag taaaattagg agaatgattt 1680
aggattttag atgattagtt ataatagatg attgtagata attaatataa ttattatttt 1740
tattattgat attttgattt tgttttgtat ttttaaaagt aggattttgt attttattgt 1800
attatagttt ttataataat ttttgtgggt aggaaaagta agtataagta ttatttttat 1860
tttttagatg aggaattggt atagaaagat gggatgattg gtggttagtt aggaatttgt 1920 tattttttttt tattgttttt ttttatttga agagagatat gtattttttt gaatgttagt 1980
agttgtttta tttaattgta aatggttatt tgtagttggg attttttatt tttttatatt 2040

-continued

```
tttgtttttt tttttttttt ttttgtttta ttttgttaga aatgttataa gtttggaata   2100
aatagaaata gggagaaatg taagtttagt tttttttta gaatttttttt gtttatattt   2160
tagataagtg atattgggat agtagaggtt gaagaatttg tgagagatgg tatttttaag   2220
aatattttg aaattttttt ttttttttg agtattttag ttataggaaa gggaaattag   2280
tttttatatt tttttgattt gtttttttta tttagtttta aaaatttttt ttgtttttat   2340
tttaattgtg gtttaatttg tagagatgtt tttgtttttt gatgtttttt tagtattgtt   2400
tttattgttt tatggggtat gattttattg ttttttaat tatagtagga atattttgag   2460
gtttgggata tttagttata ttgtttttta gtttttttag aattaaatag ggttttagga   2520
gattggagag tatgggtgtg gttaatagtt gattgagttt tgagtagagt gttttggagg   2580
ttattttaag gatttaggtt gaatgagggt atatgtggtg gaatttgaga gatttgttta   2640
tttttgtgtt ttatatgatt tattttatag ttatgtggaa ggttttagaa gatttttttag   2700
attaaattta ttttggataa gtattttata tgatagaggt tttttttttt tttttttttt   2760
atattttagt tttgtttaaa gtgttgatat ttttttaat ggaaggtttt gtttggaata   2820
taagtattaa gtagataatt tttgttgaat tttaagtagt agtttttttta tagaaagtat   2880
ttgaagtgtt ttttttagt agttatttaa ttatgaaagt ataagtataa tttgattttt   2940
tttttagttg aaaagtaatg aaattatttt ttggttaatt tttttttatt ttttatttta   3000
agttggttta tatagtgttt tgaagtttag tgaattttaa gagtttttta gttgggatgt   3060
ttttttttat tttaaatttg agttagtttt tttttgttta ttgtgtgaag gtagtttggt   3120
ttttatttta aggaaaagaa atagtaaatt ttatgaattt ttgtgtaggg gagtttttttt   3180
gttagggtta tttttttttag taggtattta ttagtttgga tgttatggtg tttatgagtt   3240
taataatatg taagaattgg ttatttaata ttatttaata agttaggtgg ggtgaatttg   3300
aggttaatag taagaatgaa gatgtaggtt gggtgtggtg gtttatgttt gtaattttag   3360
tattttgaga ggttaaggtg ggtggattat gaggttagga gattgagatt attttggtta   3420
atatggtgaa attttgtttg tattaataat ataaaaaatt agttaggtgt ggtggtgggt   3480
gtttgtagtt ttagttattt gggaggttga ggtaggagaa tggtgtgaat ttgggaggtg   3540
gagtttgtag tgagttgaga ttatgttatt gtattttagt ttaggtgatg gagtgagatt   3600
ttgtttttaa aaaaaaaaaa aaaaaaaaaa agaatgaaga tgtaggtttt tttgtttttt   3660
tttgatagtt aagaataatg atagagttat atatttggga agaattgagt aagttttaag   3720
atttatttgg tttgtttata tatttattag gatgatttgg tatttttttt tttggaattt   3780
ttttaggaaa ggtgagttta tatttatttt ttttgtatta agttatagga tgttagagtt   3840
tgtaggaaga gaagttgtaa aaaggatttt agaaattatt tatttttgtt ttaaatgtgg   3900
gaaaaataag gtttagagaa gtgaaggaat ttgtttattt ttagggttta gttttttaag   3960
ttgtaaggtg tggtttatgt ttgtattgtg ggtttggaaa ttttagttat ttatagattt   4020
tgtatttgtt ttttagattt gtagatagat ttgtttgagt ttttgtatag tgtttagttt   4080
atagagaaat tttatttata ttgattaaat aattttttat tatgataata attatttttt   4140
gagttaatta gaagtaatat aggtttgttt ttttgatagg tttatttttt gtgtgtttat   4200
tttttttttt ttttaaatta ttagttaatg tattttaaat atattattat aaaaaaaagt   4260
atatgaaaat tttgtttttg ggaaatgaaa agagagtaaa gtggaaataa aaaattaaaa   4320
gatttgagat ttgtttttaa tgttgtagaa tagttgtgta tttgttttgg ttaagttatt   4380
ttgtttgttt aggtgtttat ttttgtgttt attggatgaa agatagaatt tagtggtatt   4440
```

taggattttt tttgttttaa aaattttaag attttatggg gaattttgta ggataagtga 4500
a 4501

<210> SEQ ID NO 58
<211> LENGTH: 3001
<212> TYPE: DNA
<213> ORGANISM: Artificial Sequence
<220> FEATURE:
<223> OTHER INFORMATION: chemically treated genomic DNA (Homo sapiens)

<400> SEQUENCE: 58
gaagtgttaa tgttagattt ttatttatta tataagttta tttttgtatt agggtagtga 60 ttttttttt tgggtgagat tttgaaattt gggattataa ttttgaatta taattataaa 120
atggtatttg gttgtaaatt attttttttt ttttttgtt ttttatagtt gatattatgg 180
atttttataa ggatttatgt tttttattta ttttaatgaa tagttgttgg gtaataattt 240
tagaagagtt ttaattttta ttaggagaat ggataaggtg gagaagtaga gaaaatgtaa 300
tgagtagaat gtttaagtta ttattttgga attgattgaa tataaataaa aatgagaaag 360
atatgtaaaa aagaagggaa tgggtaagta gggtgatgtt tgggagagga ggggttttat 420
agttatgaga gttaattttg taatatttta tagggttata atattgtttt ttatatattg 480
aggtagtagt agggaaattt tttaattatt agaaatattg aattttgttt tttattttta 540
aatatttttt ttatttagtt tttgtttttt tttattttttg taatttttat tgttttaaaa 600
atgatttttt tttttttgga agaagtaatt ttttaaattt agtttatata aggggatttg 660
atatgtttaa taagttttaa atatattgta tttagtaata tttattatat gtttattttg 720
agttttgagt aatttgtatt ttaagtttag tttttattgt tttgtttttg gtaaattttt 780
attaagtgtt tttttttttt aaatatatgt atatgtttat tagattttaa agttttttat 840
gaatatgtaa attttttttt tttgaaaatt tttgtgtgag tggttagtag gttaatttat 900
ttattgtaat gtggttttgt gttagggttt tgtttttgtg ttgtttgtaa gataattata 960
gatgtgattg tattttagaa gtttttgaat tttttaagat agtttggttt ataagaaaat 1020
taaaaggtgg aggttgggtg tggtggttta tgtttgtaat tttagtattt tgggaggttg 1080
aggtgggtgg attatttgag gttgggagtt tgaaattagt ttgattaata tggggaaatt 1140
ttgtttttgt taaaaatata aaattagtta ggtgtggtgg tgtatgtttg taattttagt 1200
tatttgggag gttgaggtag gagaattgtt tgaatttggg aggtagaggt tgtgatgagt 1260
tgagattgtg ttattgtatt ttagtttggg taataagagt gaaattttgt tatatatata 1320
taaatatata tatatatata tatatggtgt agtttaggaa gtaaaaaaaa aaaaaaaaaa 1380
aaaattagat tttttttat attttagatt tgaaggtata aattttaggg ttagggtgtt 1440
tgtttattta attttatatg tatttgtagg ttatttagta tttaggtatt tagtatttag 1500
gtatattgtg gttttttatt ttttatgata gtagtaataa tgttgattgg aagtttatta 1560
ttgtgtgtta tgggttatgg gttatgtgtg ttagaatttt atgtgaaatt aatatttaat 1620
ttttatggat atttttgaaa tagatgttat agtttttatt ttgttaatga ggtagttgag 1680
gtttttagag gtttaatatt agtattatga gttgtagtat gtaaggtaaa tatagttgga 1740
ggtgagtata tatttgtttt gtattttatg tgtttaatta taaggttttt ttttttttagg 1800 aaggttgttg tttttttttgg gatgatttgt tagttttgag gtatgatagt atgggttttt 1860
agaagggtga ttaggaggtt ttttttgttt tagttgttgg tgttgttgtt tattgtaggg 1920
tttgggttgt gatttgtggg gatggttttt tgtgttttgg tgggggaggt gggtggggag 1980

```
gggtggtggg gtgttggggt ggggtttggg atggttgggt tgggagttgg agtttatagt   2040

gggaagtggt tgttgtttgg gttttgtagg gttaggtgag gtgagggggg gtggggttgg   2100

gtgttatggg aaggggaggt tgtgtggatt gggagttgta ttgtgttagt tgggttgtag   2160

tggttgtgta ttaaggttgt gatggggttg gagatggaga aggtggatgt atagtttttt   2220

atggatgatg atttttatag ttattatagt ggttttgagt atgttgattt tgagaagttt   2280

gtggatttgg attaggattg ggatttttat tggtttaatt tgtattttaa ggtgaagttt   2340

ggggtgggtg ggtttaagtt tttgttgagg ttgggaggtg tgggtgtttt ttagttttgt   2400

tttaatttgt tttattattg ttattgggtt ggttttgtag ggtttgagat ttgtattttt   2460

ttttggtttt atttgttatt aggttgtttg tgtagttagg aatttttagt taggtttttg   2520

tgtgtttatt gtgattttaa gagaagaggt ggatgttttg gtatgttttt tttttttgtt   2580

tttttgttt aaagtgtttt tggtttttgg ggtgttaggt tggttgatag tttggggttt   2640

ttgtgttttg tttttttagt tgggttttga ggatgtgatt gtagagttgg tgattatgta   2700

ttttttgat aaagtgtgga tttgtagtta tgtttttttt gaaattagta aatatgtaat   2760

gtataagttt ttgatggtgt ttttggttat ttttttggtt tttattgtgg gaattttttt   2820

tgttattttt agttgtttgt atatttggtg agatggggta tattgggtgg attggttttt   2880

tgaaatatgg gtatattttt tgttatttgt tttttatttt ttttttattt taggttggtg   2940

ttaggaggag gaatgtgtat tagtttttaa gtagtaggaa gaattggaag gttttgaaag   3000

g                                                                   3001
```

<210> SEQ ID NO 59
<211> LENGTH: 3001
<212> TYPE: DNA
<213> ORGANISM: Artificial Sequence
<220> FEATURE:
<223> OTHER INFORMATION: chemically treated genomic DNA (Homo sapiens)

<400> SEQUENCE: 59

```
tttttaagg tttttagtt ttttttattg tttgggaatt gatgtgtgtt tttttttttg     60

atgttggttt gggataagag gagagtaggg ggtaggtggt ggagaatatg tttatgtttt    120

agaaagttgg tttatttggt gtgttttgtt ttattagatg tgtagatagt tgagggtggt    180

aaagagaatt tttgtaatga aggttagggg aatggttagg aatattgtta ggaatttgta    240

tattatgtat ttgttgattt taaagagggt atggttgtag atttatattt tgttaaagga    300

gtgtgtagtt attggttttg tgattatatt tttgaagttt agttgaggag ataggatgta    360

gggattttga attgttagtt aatttgatgt tttgggaatt gggagtgttt tgggtggggg    420

aagtaggagg gaaggatgtg ttagggtgtt tgtttttttt tttagggtta tggtgggtgt    480

ataggaattt ggttaagaat ttttggttat gtgggtggtt tggtgatggg tgggattggg    540

gaagggtgtg ggttttagat tttgtggggt tgatttggta gtaatggtgg gatgggttag    600

ggtggggttg aggggtgttt gtatttttttg gttttagtgg ggatttgggt ttgtttgttt    660

tgggttttat tttgagatgt gagttgagtt ggtggggatt ttggttttgg tttgagtttg    720

tgaatttttt ggggttggtg tatttgaggt tgttgtggtg gttgtaggag ttgttgttta    780

tgaagagttg tatgtttgtt ttttttgttt ttagttttat tgtagttttg gtgtgtggtt    840

gttgtagttt ggttggtgtg gtgtggtttt tggtttgtgt ggttttttttt ttttgtagtg    900

tttggttttg ttttttttttg ttttgtttag ttttgtgagg tttgggtggt ggttgttttt    960

tgttgtgggt tttagttttt agtttggttg ttttgagttt tgttttggtg ttttgttgtt   1020
```

```
tttttttgtt tattttttttt gttggggtgt agggaattgt ttttatgagt tatagtttgg   1080

gttttgtagt gggtggtgat gttggtagtt gggatgagga gggtttttttg gttattttttt   1140

tgggggtttg tattgttatg ttttagagtt ggtaagttgt tttagggaag ataatggttt   1200

ttttggaggg agggaatttt gtggttaggt gtatggggtg tgaagtaggt atgtgtttat   1260

ttttggttgt gtttgtttttg tgtgttgtgg tttatggtgt tggtattgag tttttgggaa   1320

ttttagttgt tttgttggta aaatgggggt tgtggtattt gttttagggg tgtttgtgag   1380

aattaaatgt taattttata taaaatttta atatatatgg tttatggttt gtaatatata   1440

gtgataaatt tttaattaat gttgttgttg ttgttgtgag aggtaaggag ttataatgta   1500

tttgagtgtt aggtatttga gtgttaggtg atttgtaagt gtatgtggag ttgggtaggt   1560

gaatgttttg gttttagagt ttgtgttttt agatttgagg tgtgaggggga gatttgattt   1620

ttttttttttt tttttttta tttttaaat tatattgtgt gtgtgtgtgt gtgtgtgttt   1680

gtgtgtgtgt ggtagagttt tgtttttgtt gtttaggttg gagtgtaatg gtatgatttt   1740

ggtttattgt aatttttgtt ttttgggttt aagtgatttt tttgttttag tttttttgagt   1800

agttgggatt ataggtatgt attattatgt ttggttaatt ttgtattttt agtagagatg   1860

gggtttttttt atgttggtta ggttggtttt gaatttttaa ttttaggtga tttgtttgtt   1920

ttggtttttt aaagtgttgg gattgtaggt gtgagttatt gtgtttgatt tttatttttt   1980

aatttttttg tgaattagat tgttttgaaa gatttaggaa tttttaagat gtagttatat   2040

ttgtgattat tttgtaggta gtatggaaat agaattttaa tataaagtta tattgtaatg   2100

gatgaattag tttgttgatt atttatgtaa aggtttttag aagggaggag tttgtatgtt   2160

tataaagggt tttagggttt ggtagatata tatgtgtgtt tggggaggaa gggtatttag   2220

tgaaaatttg ttaaaagtaa aataatgaga attaggtttg aggtgtaggt tgtttagagt   2280

ttaaagtagg tatgtagtag gtattgttgg atatagtgta tttggagttt gttgaatata   2340

ttaaattttt ttatgtgaat tggatttgaa gaattgtttt ttttgaaaga aaaaagatta   2400

tttttgaaat agtaaaaatt atagaaataa aaaagaatag gaattgaatg agaaaaatgt   2460

ttgggggtgg gaggtaaagt ttaatatttt taataattaa aaagtttttt tgttgttatt   2520

ttagtatatg aagggtagtg ttgtaatttt atagggtgtt atagagttga tttttatggt   2580

tatggagttt ttttttttt agatattatt ttgtttattt atttttttttt tttttatgta   2640

ttttttttat ttttatttat gtttagttaa ttttaaagtg atgatttaga tattttattt   2700

attgtatttt ttttgttttt ttattttgtt tattttttttg atgagaattg gaattttttt   2760

agaattgttg tttaataatt gtttattaaa gtgaatagaa gatatgaatt tttatgggaa   2820

tttataatat taattgtgag gaatagaaaa aaaaaggaga taatttatag ttaaatatta   2880

ttttataatt ataatttaaa attataattt tagattttaa ggttttattt aaagaagaaa   2940

gttattgttt tagtataaga gtgggtttat gtagtgggta aaaatttgat attagtattt   3000

t                                                                    3001
```

<210> SEQ ID NO 60
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 60

```
ataaatcatc ccaaaacctc ta                                             22
```

<210> SEQ ID NO 61
<211> LENGTH: 18
<212> TYPE: DNA
<213> ORGANISM: Artificial Sequence
<220> FEATURE:
<223> OTHER INFORMATION: chemically treated genomic DNA (Homo sapiens)

<400> SEQUENCE: 61
cgcgctactc cgcataca 18

<210> SEQ ID NO 62
<211> LENGTH: 19
<212> TYPE: DNA
<213> ORGANISM: Artificial Sequence
<220> FEATURE:
<223> OTHER INFORMATION: chemically treated genomic DNA (Homo sapiens)

<400> SEQUENCE: 62
gaggtaatcg aggcggtcg 19

<210> SEQ ID NO 63
<211> LENGTH: 21
<212> TYPE: DNA
<213> ORGANISM: Artificial Sequence
<220> FEATURE:
<223> OTHER INFORMATION: chemically treated genomic DNA (Homo sapiens)

<400> SEQUENCE: 63
cgccaattca tacgccgcac c 21

<210> SEQ ID NO 64
<211> LENGTH: 19
<212> TYPE: DNA
<213> ORGANISM: Artificial Sequence
<220> FEATURE:
<223> OTHER INFORMATION: chemically treated genomic DNA (Homo sapiens)

<400> SEQUENCE: 64
accgaaaata cgcttcacg 19

<210> SEQ ID NO 65
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 65
gcgttatcgt aaagtattgc gc 22

<210> SEQ ID NO 66
<211> LENGTH: 19
<212> TYPE: DNA
<213> ORGANISM: Artificial Sequence
<220> FEATURE:
<223> OTHER INFORMATION: chemically treated genomic DNA (Homo sapiens)

<400> SEQUENCE: 66
cgcgacgaac aaaacgccg 19

<210> SEQ ID NO 67
<211> LENGTH: 18
<212> TYPE: DNA
<213> ORGANISM: Artificial Sequence
<220> FEATURE:
<223> OTHER INFORMATION: chemically treated genomic DNA (Homo sapiens)

<400> SEQUENCE: 67
gcgttttacg tcgtcgcg 18

<210> SEQ ID NO 68
<211> LENGTH: 18
<212> TYPE: DNA
<213> ORGANISM: Artificial Sequence
<220> FEATURE:
<223> OTHER INFORMATION: chemically treated genomic DNA (Homo sapiens)

<400> SEQUENCE: 68
gacgctaaac gccaccgt 18

<210> SEQ ID NO 69
<211> LENGTH: 23
<212> TYPE: DNA
<213> ORGANISM: Artificial Sequence
<220> FEATURE:
<223> OTHER INFORMATION: chemically treated genomic DNA (Homo sapiens)

<400> SEQUENCE: 69
ccgaccatcc gacgccttac tcg 23

<210> SEQ ID NO 70
<211> LENGTH: 21
<212> TYPE: DNA
<213> ORGANISM: Artificial Sequence
<220> FEATURE:
<223> OTHER INFORMATION: chemically treated genomic DNA (Homo sapiens)

<400> SEQUENCE: 70
cgtttttcgt tttattttcg c 21

<210> SEQ ID NO 71
<211> LENGTH: 18
<212> TYPE: DNA
<213> ORGANISM: Artificial Sequence
<220> FEATURE:
<223> OTHER INFORMATION: chemically treated genomic DNA (Homo sapiens)

<400> SEQUENCE: 71
gacaaaaaac gccacgtc 18

<210> SEQ ID NO 72
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 72
ccgacaattc accgaatcac cg 22

<210> SEQ ID NO 73
<211> LENGTH: 18
<212> TYPE: DNA
<213> ORGANISM: Artificial Sequence
<220> FEATURE:
<223> OTHER INFORMATION: chemically treated genomic DNA (Homo sapiens)

<400> SEQUENCE: 73
atctcaccta ccgtcgcg 18

<210> SEQ ID NO 74
<211> LENGTH: 19

-continued

```
<212> TYPE: DNA
<213> ORGANISM: Artificial Sequence
<220> FEATURE:
<223> OTHER INFORMATION: chemically treated genomic DNA (Homo sapiens)

<400> SEQUENCE: 74

taggagtgcg atcgtttgc                                                    19


<210> SEQ ID NO 75
<211> LENGTH: 27
<212> TYPE: DNA
<213> ORGANISM: Artificial Sequence
<220> FEATURE:
<223> OTHER INFORMATION: chemically treated genomic DNA (Homo sapiens)

<400> SEQUENCE: 75

acgaacgtta cgaccgatac ccaacta                                           27


<210> SEQ ID NO 76
<211> LENGTH: 25
<212> TYPE: DNA
<213> ORGANISM: Artificial Sequence
<220> FEATURE:
<223> OTHER INFORMATION: chemically treated genomic DNA (Homo sapiens)

<400> SEQUENCE: 76

tgaatagggt gatattttag ttagg                                             25
```

METHODS AND NUCLEIC ACIDS FOR ANALYSIS OF COLON PROLIFERATIVE DISORDERS

CROSS-REFERENCE TO RELATED APPLICATIONS

This application claims the benefit of priority to U.S. patent application Ser. No. 10/603,138, filed 23 Jun. 2003 and entitled METHODS AND NUCLEIC ACIDS FOR ANALYSES OF COLORECTAL CELL PROLIFERATIVE DISORDERS, which is incorporated herein by reference in its entirety.

FIELD OF THE INVENTION

Aspects of the present invention relate to cancer, and to the detection and progression of cancer. More particular aspects relate to nucleic acids and kits having diagnostic, prognostic and therapeutic utility for detecting and distinguishing colon cell proliferative disorders, based on methylation patterns of relevant genomic DNA sequences.

BACKGROUND

In the United States the annual incidence of colorectal cancer is approximately 150,000, with 56,600 individuals dying from colorectal cancer each year. The lifetime risk of colorectal cancer in the general population is about 5 to 6 percent. Despite intensive efforts in recent years in screening and early detection of colon cancer, until today most cases are diagnosed in an advanced stage with regional or distant metastasis. While the therapeutic options include surgery and adjuvant or palliative chemotherapy, most patients die from progression of their cancer within a few months. Identifying the molecular changes that underly the progression of colon cancer and the formation of metastasis may help to develop new diagnostic and therapeutic options that could improve the overall poor prognosis of these patients.

The current model of colorectal pathogenesis favours a stepwise progression of adenomas which includes the development of dysplasia and finally signs of invasive cancer. The molecular changes underlying this adenoma-carcinoma sequence include genetic and epigenetic alterations of tumor suppressor genes (APC, p 53, DCC), the activation of oncogenes (K-ras) and the inactivation of DNA mismatch repair genes[1]. Recently, further molecular changes and genetic defects have been revealed. Thus, activation of the Wnt signalling pathway not only includes mutations of the APC gene, but may also result from beta-catenin mutations[5]. Furthermore, alterations in the TGF-beta signalling pathway together with its signal transducers SMAD4 and SMAD2 have been linked to the development of colon cancer.

Despite recent progress in the understanding of the pathogenesis of adenomas and carcinomas of the colon and their genetic and molecular changes, the genetic and epigenetic changes underlying the development of metastasis are less well understood. It is, however, generally well accepted that the process of invasion and proteolysis of the extracellular matrix, as well as infiltration of the vascular basement membrane involve adhesive proteins, such as members of the family of integrin receptors, the cadherins, the immunoglobulin superfamily, the laminin binding protein and the CD44 receptor. Apart from adhesion, the process of metastasis formation also includes the induction and regulation of angiogenesis (VEGF, bFGF), the induction of cell proliferation (EGF, HGF, IGF) and the activation of proteolytic enzymes (MMPs, TIMPs, uPAR), as well as the inhibition of apoptosis (Bcl-2, Bcl-X). More recently other groups have compared the genetic and molecular changes in metastatic lesions to the changes found in primary colorectal cancers. Thus, Kleeff et al. reported the loss of DOC-2, a candidate tumor suppressor gene, both in primary and metastatic colorectal cancer. Furthermore, Zauber et al. reported that in their series of 42 colorectal cancers Ki-ras mutations in the primary cancers were identical in all of the 42 paired primary and synchronous metastatic lesions. Similarly loss of heterozygosity at the APC locus was identical for 39 paired carcinomas and synchronous metastasis. The authors concluded that for Ki-ras and APC genes the genetic changes in metastasis are identical to the primary colorectal cancer. However, other groups have found genetic and molecular changes in metastatic colon cancers, that are not present in the primary cancers. Thus, the development of LOH of chromosome 3p in colorectal metastasis has been reported. In addition, using comparative genomic hybridization several alterations were found in liver metastasis that were unique to metastastic lesions (−9q, −11q, and −17q)[38].

Apart from mutations aberrant methylation of CpG islands has been shown to lead to the transcriptional silencing of certain genes that have been previously linked to the pathogenesis of various cancers. CpG islands are short sequences which are rich in CpG dinucleotides and can usually be found in the 5' region of approximately 50% of all human genes. Methylation of the cytosines in these islands leads to the loss of gene expression and has been reported in the inactivation of the X chromosome and genomic imprinting. Recently several groups have also analysed the methylation of various genes in colorectal cancer and reported the transcriptional silencing by promoter methylation for p16INK4, p14ARF, p15INK4b, MGMT, hMLH1, GSTP1, DAPK, CDH1, TIMP-3 and APC among others. Thus apart from mutational inactivation of certain genes, the hypermethylation of these genes also contributes significantly to the pathogenesis of this disease.

In recent years several genes that are methylated in colon cancer have been identified by MS AP-PCR. This group of genes among others, includes TPEF/HPP1 which is frequently methylated in colon cancers and which was independently identified by two different groups using the MS AP-PCR method. See for example, Young J, Biden K G, Simms L A, Huggard P, Karamatic R, Eyre H J, Sutherland G R, Herath N, Barker M, Anderson G J, Fitzpatrick D R, Ramm G A, Jass J R, Leggett B A. HPP1: a transmembrane protein-encoding gene commonly methylated in colorectal polyps and cancers. Proc Natl Acad Sci USA 2001; 98:265-270.

ALX4 gene methylation was identified using differential methylation hybridization in a study by Yan et al. of genome-wide screening for CpG island hypermethylation in breast cancer samples. In their study ALX4 gene methylation was most prominent in poorly differentiated breast cancers (Yan P S, Perry M R, Laux D E, Asare A L, Caldwell C W, Huang T H. CpG island arrays: an application toward deciphering epigenetic signatures of breast cancer. Clin Cancer Res 2000; 6:1432-1438). ALX4 is a putative transcription factor that belongs to the family of paired-class homeoproteins. This gene is part of a family of genes that includes the mammalian genes Alx3, Cart-1, MHox, and S8 and exhibits similarity to the *Drosophila* gene aristaless. It binds palindromic DNA sequences (5'-TAAT-3') as either homodimers or as heterodimers with other family members and strongly activates transcription from a promoter containing the homeodomain binding site, P2. ALX4 is expressed at several sites during development, including the craniofacial and limb-bud mesenchyme. Interestingly, ALX4 deficient mice exhibit bodywall defects, preaxial polydactyl), and a decreased size of the parietal plate of the skull, while mutations of the human homeobox gene ALX4 have been found in inherited defects of skull ossification. ALX4 is also expressed in various tissues whose development is dependent on epithelial-mesenchymal interactions and regulates mesenchymal-specific activities of LEF-1.

Multifactorial approach. Cancer diagnostics has traditionally relied upon the detection of single molecular markers (e.g. gene mutations, elevated PSA levels). Unfortunately, cancer is a disease state in which single markers have typically failed to detect or differentiate many forms of the disease. Thus, assays that recognize only a single marker have been shown to be of limited predictive value. A fundamental aspect of this invention is that methylation based cancer diagnostics and the screening, diagnosis, and therapeutic monitoring of such diseases will provide significant improvements over the state-of-the-art that uses single marker analyses by the use of a selection of multiple markers. The multiplexed analytical approach is particularly well suited for cancer diagnostics since cancer is not a simple disease, this multi-factorial "panel" approach is consistent with the heterogeneous nature of cancer, both cytologically and clinically.

Key to the successful implementation of a panel approach to methylation based diagnostic tests is the design and development of optimized panels of markers that can characterize and distinguish disease states. This patent application describes an efficient and unique panel of genes the methylation analysis of one or a combination of the members of the panel enabling the detection of cell proliferative disorders of the prostate with a particularly high sensitivity, specificity and/or predictive value.

Development of medical tests. Two key evaluative measures of any medical screening or diagnostic test are its sensitivity and specificity, which measure how well the test performs to accurately detect all affected individuals without exception, and without falsely including individuals who do not have the target disease (predicitive value). Historically, many diagnostic tests have been criticized due to poor sensitivity and specificity.

A true positive (TP) result is where the test is positive and the condition is present. A false positive (FP) result is where the test is positive but the condition is not present. A true negative (TN) result is where the test is negative and the condition is not present. A false negative (FN) result is where the test is negative but the condition is present. In this context: Sensitivity=TP/(TP+FN); Specificity=TN/(FP+TN); and Predictive value=TP/(TP+FP).

Sensitivity is a measure of a test's ability to correctly detect the target disease in an individual being tested. A test having poor sensitivity produces a high rate of false negatives, i.e., individuals who have the disease but are falsely identified as being free of that particular disease. The potential danger of a false negative is that the diseased individual will remain undiagnosed and untreated for some period of time, during which the disease may progress to a later stage wherein treatments, if any, may be less effective. An example of a test that has low sensitivity is a protein-based blood test for HIV. This type of test exhibits poor sensitivity because it fails to detect the presence of the virus until the disease is well established and the virus has invaded the bloodstream in substantial numbers. In contrast, an example of a test that has high sensitivity is viral-load detection using the polymerase chain reaction (PCR). High sensitivity is achieved because this type of test can detect very small quantities of the virus. High sensitivity is particularly important when the consequences of missing a diagnosis are high.

Specificity, on the other hand, is a measure of a test's ability to identify accurately patients who are free of the disease state. A test having poor specificity produces a high rate of false positives, i.e., individuals who are falsely identified as having the disease. A drawback of false positives is that they force patients to undergo unnecessary medical procedures treatments with their attendant risks, emotional and financial stresses, and which could have adverse effects on the patient's health. A feature of diseases which makes it difficult to develop diagnostic tests with high specificity is that disease mechanisms, particularly in cancer, often involve a plurality of genes and proteins. Additionally, certain proteins may be elevated for reasons unrelated to a disease state. An example of a test that has high specificity is a gene-based test that can detect a p53 mutation. Specificity is important when the cost or risk associated with further diagnostic procedures or further medical intervention are very high.

Bisulfite modification of DNA is an art-recognized tool used to assess CpG methylation status. 5-methylcytosine is the most frequent covalent base modification in the DNA of eukaryotic cells. It plays a role, for example, in the regulation of the transcription, in genetic imprinting, and in tumorigenesis. Therefore, the identification of 5-methylcytosine as a component of genetic information is of considerable interest. However, 5-methylcytosine positions cannot be identified by sequencing, because 5-methylcytosine has the same base pairing behavior as cytosine. Moreover, the epigenetic information carried by 5-methylcytosine is completely lost during, e.g., PCR amplification.

The most frequently used method for analyzing DNA for the presence of 5-methylcytosine is based upon the specific reaction of bisulfite with cytosine whereby, upon subsequent alkaline hydrolysis, cytosine is converted to uracil which corresponds to thymine in its base pairing behavior. Significantly, however, 5-methylcytosine remains unmodified under these conditions. Consequently, the original DNA is converted in such a manner that methylcytosine, which originally could not be distinguished from cytosine by its hybridization behavior, can now be detected as the only remaining cytosine using standard, art-recognized molecular biological techniques, for example, by amplification and hybridization, or by sequencing. All of these techniques are based on differential base pairing properties, which can now be fully exploited.

The prior art, in terms of sensitivity, is defined by a method comprising enclosing the DNA to be analyzed in an agarose matrix, thereby preventing the diffusion and renaturation of the DNA (bisulfite only reacts with single-stranded DNA), and replacing all precipitation and purification steps with fast dialysis (Olek A, et al., A modified and improved method for bisulfite based cytosine methylation analysis, *Nucleic Acids Res.* 24:5064-6, 1996). It is thus possible to analyze individual cells for methylation status, illustrating the utility and sensitivity of the method. An overview of art-recognized methods for detecting 5-methylcytosine is provided by Rein, T., et al., *Nucleic Acids Res.*, 26:2255, 1998.

The bisulfite technique, barring few exceptions (e.g., Zeschnigk M, et al., *Eur J Hum Genet.* 5:94-98, 1997), is currently only used in research. In all instances, short, specific fragments of a known gene are amplified subsequent to a bisulfite treatment, and either completely sequenced (Olek & Walter, *Nat. Genet.* 1997 17:275-6, 1997), subjected to one or more primer extension reactions (Gonzalgo & Jones, *Nucleic Acids Res.*, 25:2529-31, 1997; WO 95/00669; U.S. Pat. No. 6,251,594) to analyze individual cytosine positions, or treated by enzymatic digestion (Xiong & Laird, *Nucleic Acids Res.*, 25:2532-4, 1997). Detection by hybridization has also been described in the art (Olek et al., WO 99/28498). Additionally, use of the bisulfite technique for methylation detection with respect to individual genes has been described (Grigg & Clark, Bioessays, 16:431-6, 1994; Zeschnigk M, et al., *Hum Mol. Genet.,* 6:387-95, 1997; Feil R, et al., *Nucleic Acids Res.,* 22:695-, 1994; Martin V, et al., *Gene,* 157:261-4, 1995; WO 9746705 and WO 9515373).

Bisulfite Methylation Assay Procedures. Various methylation assay procedures are known in the art, and can be used in conjunction with the present invention. These assays allow for determination of the methylation state of one or a plurality of CpG dinucleotides (e.g., CpG islands) within a DNA sequence. Such assays involve, among other techniques, DNA sequencing of bisulfite-treated DNA, PCR (for sequence-specific amplification), Southern blot analysis, and use of methylation-sensitive restriction enzymes.

For example, genomic sequencing has been simplified for analysis of DNA methylation patterns and 5-methylcytosine distribution by using bisulfite treatment (Frommer et al., *Proc. Natl. Acad. Sci. USA* 89:1827-1831, 1992). Additionally, restriction enzyme digestion of PCR products amplified from bisulfite-converted DNA is used, e.g., the method described by Sadri & Hornsby (*Nucl. Acids Res.* 24:5058-5059, 1996), or COBRA (Combined Bisulfite Restriction Analysis) (Xiong & Laird, *Nucleic Acids Res.* 25:2532-2534, 1997).

COBRA. COBRA™ analysis is a quantitative methylation assay useful for determining DNA methylation levels at specific gene loci in small amounts of genomic DNA (Xiong & Laird, *Nucleic Acids Res.* 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (*Proc. Natl. Acad. Sci. USA* 89:1827-1831, 1992). PCR amplification of the bisulfite converted DNA is then performed using primers specific for the interested CpG islands, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples.

Other assays used in the art include "MethyLight™" (a fluorescence-based real-time PCR technique) (Eads et al., *Cancer Res.* 59:2302-2306, 1999), Ms-SNuPET™ (Methylation-sensitive Single Nucleotide Primer Extension) reactions (Gonzalgo & Jones, *Nucleic Acids Res.* 25:2529-2531, 1997), methylation-specific PCR ("MSP"; Hernan et al., *Proc. Natl. Acad. Sci. USA* 93:9821-9826, 1996; U.S. Pat. No. 5,786,146), and methylated CpG island amplification ("MCA"; Toyota et al., *Cancer Res.* 59:2307-12, 1999). These may be used alone or in combination with other of these methods.

MethyLight. The MethyLight™ assay is a high-throughput quantitative methylation assay that utilizes fluorescence-based real-time PCR (TaqMan®) technology that requires no further manipulations after the PCR step (Eads et al., *Cancer Res.* 59:2302-2306, 1999). Briefly, the MethyLight™ process begins with a mixed sample of genomic DNA that is converted, in a sodium bisulfite reaction, to a mixed pool of methylation-dependent sequence differences according to standard procedures (the bisulfite process converts umethylated cytosine residues to uracil). Fluorescence-based PCR is then performed either in an "unbiased" (with primers that do not overlap known CpG methylation sites) PCR reaction, or in a "biased" (with PCR primers that overlap known CpG dinucleotides) reaction. Sequence discrimination can occur either at the level of the amplification process or at the level of the fluorescence detection process, or both.

The MethyLight™ assay may be used as a quantitative test for methylation patterns in the genomic DNA sample, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the "MSP" technique), or with oligonucleotides covering potential methylation sites.

The MethyLight™ process can by used with a "TaqMan®" probe in the amplification process. For example, double-stranded genomic DNA is treated with sodium bisulfite and subjected to one of two sets of PCR reactions using TaqMan® probes; e.g., with either biased primers and TaqMan® probe, or unbiased primers and TaqMan® probe. The TaqMan® probe is dual-labeled with fluorescent "reporter" and "quencher" molecules, and is designed to be specific for a relatively high GC content region so that it melts out at about 10° C. higher temperature in the PCR cycle than the forward or reverse primers. This allows the TaqMan® probe to remain fully hybridized during the PCR annealing/extension step. As the Taq polymerase enzymatically synthe sizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Alternatively the MethylLight™ process can be used with 'Lightcycler' probes. A LightCycler™ probe is a pair of single-stranded fluorescent-labeled oligonucleotides. The first oligonucleotide probe is labeled at its 3' end with a donor fluorophore dye and the second is labeled at its 5' end with an acceptor fluorophore dyes. The free 3' hydroxyl group of the second probe is blocked with a phosphate group to prevent polymerase mediated extension.

During the annealing step of real-time quantitative PCR, the PCR primers and the LightCycler™ probes hybridize to their specific target regions causing the donor dye to come into close proximity to the acceptor dye. When the donor dye is excited by light, energy is transferred by Fluorescence Resonance Energy Transfer (FRET) from the donor to the acceptor dye. The energy transfer causes the acceptor dye to emit fluorescence wherein the increase of measured fluorescence signal is directly proportional to the amount of target DNA.

Typical reagents (e.g., as might be found in a typical MethyLight™-based kit) for MethyLight™ analysis may include, but are not limited to: PCR primers for specific gene (or methylation-altered DNA sequence or CpG island); TaqMan® and/or LightCycler™ probes; optimized PCR buffers and deoxynucleotides; and Taq polymerase.

Ms-SNuPE. The Ms-SNuPE™ technique is a quantitative method for assessing methylation differences at specific CpG sites based on bisulfite treatment of DNA, followed by single-nucleotide primer extension (Gonzalgo & Jones, *Nucleic Acids Res.* 25:2529-2531, 1997). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. Small amounts of DNA can be analyzed (e.g., microdissected pathology sections), and it avoids utilization of restriction enzymes for determining the methylation status at CpG sites.

Typical reagents (e.g., as might be found in a typical Ms-SNuPE™-based kit) for Ms-SNuPE analysis may include, but are not limited to: PCR primers for specific gene (or methylation-altered DNA sequence or CpG island); optimized PCR buffers and deoxynucleotides; gel extraction kit; positive control primers; Ms-SNuPE™ primers for specific gene; reaction buffer (for the Ms-SNuPE™ reaction); and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

MSP. MSP (methylation-specific PCR) allows for assessing the methylation status of virtually any group of CpG sites within a CpG island, independent of the use of methylation-sensitive restriction enzymes (Hernan et al. *Proc. Natl. Acad. Sci. USA* 93:9821-9826, 1996; U.S. Pat. No. 5,786,146). Briefly, DNA is modified by sodium bisulfite converting all unmethylated, but not methylated cytosines to uracil, and subsequently amplified with primers specific for methylated versus unmethylated DNA. This technique has been described in U.S. Pat. No. 6,265,171 to Herman. The use of methylation status specific primers for the amplification of bisulfite treated DNA allows the differentiation between methylated and unmethylated nucleic acids. MSP primers pairs contain at least one primer which hybridizes to a bisulfite treated CpG dinucleotide. Therefore, the sequence of said primers comprises at least one CpG dinucleotide. MSP primers specific for non-methylated DNA contain a "T" at the 3' position of the C position in the CpG. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific gene (or methylation-altered DNA sequence or CpG island), optimized PCR buffers and deoxynucleotides, and specific probes.

Pronounced need in the art. Therefore, in view of the incidence of colon cancer there is a substantial need in the art for the development of molecular markers that could be used for the early detection of colorectal cell proliferative disorders, in particular colon cancer. Additionally, there is a pronounced need in the art for the development of molecular markers that could be used to provide sensitive, accurate and non-invasive methods (as opposed to, e.g., biopsy) for the diagnosis, prognosis and treatment of colon cell proliferative disorders.

DETAILED DESCRIPTION OF THE INVENTION

Figure 1:
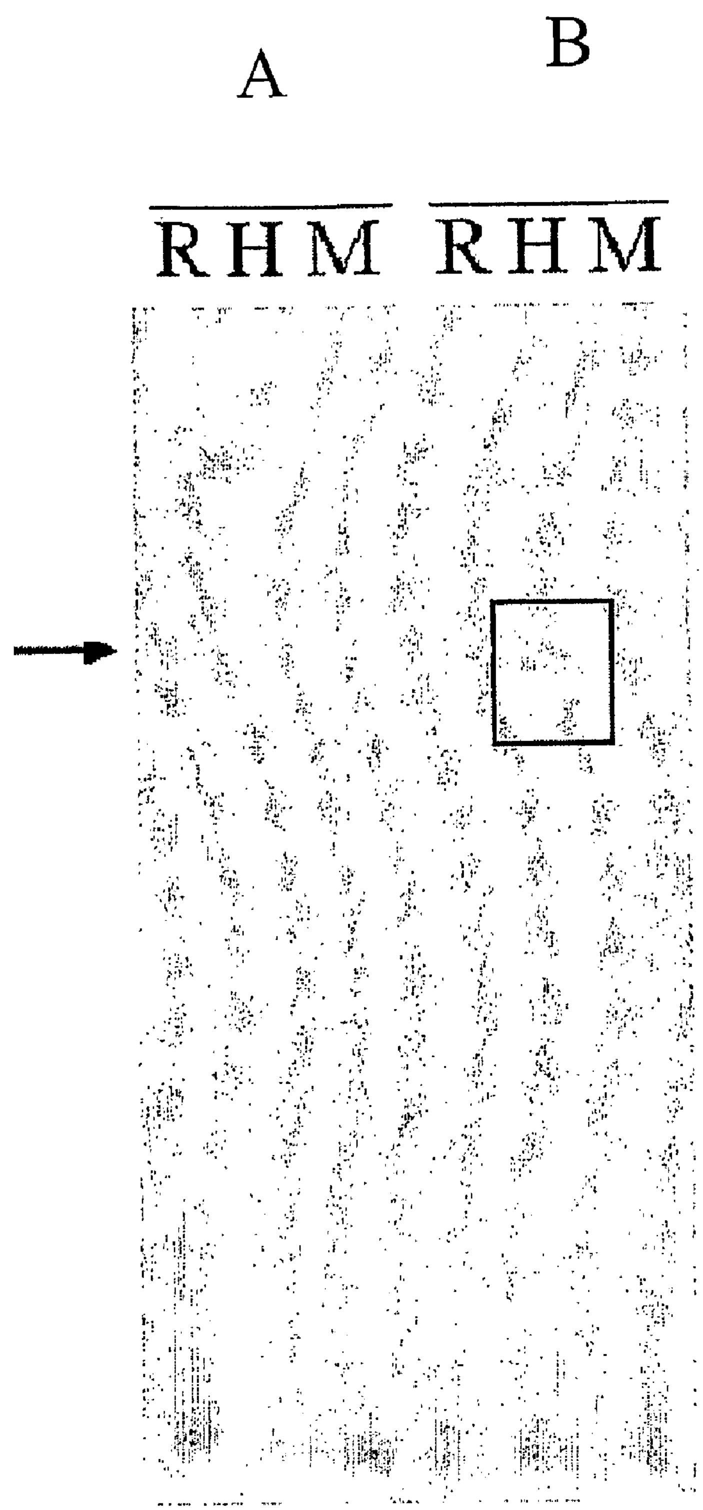
FIG. 1 shows the results of the MS-APPCR analysis of pooled DNA from normal and adenoma tissues. A hypermethylated gene (ALX4) was detected in the adenoma DNA (box, arrow). R, RsaI; H, RsaI/HpaII; M, RsaI/MspI.

For the purposes of the following invention the 'sensitivity' and 'specificity' refer to values calculated by reference to a sample set according to that described in the EXAMPLES disclosed herein.

Definitions

The term "Observed/Expected Ratio" ("O/E Ratio") refers to the frequency of CpG dinucleotides within a particular DNA sequence, and corresponds to the [number of CpG sites/(number of C bases×number of G bases) ]×band length for each fragment.

The term "CpG island" refers to a contiguous region of genomic DNA that satisfies the criteria of (1) having a frequency of CpG dinucleotides corresponding to an "Observed/Expected Ratio">0.6, and (2) having a "GC Content">0.5. CpG islands are typically, but not always, between about 0.2 to about 1 kb in length.

The term "methylation state" or "methylation status" refers to the presence or absence of 5-methylcytosine ("5-mCyt") at one or a plurality of CpG dinucleotides within a DNA sequence. Methylation states at one or more particular palindromic CpG methylation sites (each having two CpG CpG dinucleotide sequences) within a DNA sequence include "unmethylated," "fully-methylated" and "hemi-methylated."

The term "hemi-methylation" or "hemimethylation" refers to the methylation state of a palindromic CpG methylation site, where only a single cytosine in one of the two CpG dinucleotide sequences of the palindromic CpG methylation site is methylated (e.g., 5'-NC$^{M}$GN-3' (top strand): 3'-NGCN-5' (bottom strand)).

The term "hypermethylation" refers to the average methylation state corresponding to an increased presence of 5-mCyt at one or a plurality of CpG dinucleotides within a DNA sequence of a test DNA sample, relative to the amount of 5-mCyt found at corresponding CpG dinucleotides within a normal control DNA sample.

The term "hypomethylation" refers to the average methylation state corresponding to a decreased presence of 5-mCyt at one or a plurality of CpG dinucleotides within a DNA sequence of a test DNA sample, relative to the amount of 5-mCyt found at corresponding CpG dinucleotides within a normal control DNA sample.

The term "microarray" refers broadly to both "DNA microarrays," and 'DNA chip(s),' as recognized in the art, encompasses all art-recognized solid supports, and encompasses all methods for affixing nucleic acid molecules thereto or synthesis of nucleic acids thereon. "Genetic parameters" are mutations and polymorphisms of genes and sequences further required for their regulation. To be designated as mutations are, in particular, insertions, deletions, point mutations, inversions and polymorphisms and, particularly preferred, SNPs (single nucleotide polymorphisms).

"Epigenetic parameters" are, in particular, cytosine methylations. Further epigenetic parameters include, for example, the acetylation of histones which, however, cannot be directly analyzed using the described method but which, in turn, correlate with the DNA methylation.

The term "bisulfite reagent" refers to a reagent comprising bisulfite, disulfite, hydrogen sulfite or combinations thereof, useful as disclosed herein to distinguish between methylated and unmethylated CpG dinucleotide sequences.

The term "Methylation assay" refers to any assay for determining the methylation state of one or more CpG dinucleotide sequences within a sequence of DNA.

The term "MS AP-PCR" (Methylation-Sensitive Arbitrarily-Primed Polymerase Chain Reaction) refers to the art-recognized technology that allows for a global scan of the genome using CG-rich primers to focus on the regions most likely to contain CpG dinucleotides, and described by Gonzalgo et al., *Cancer Research* 57:594-599, 1997.

The term "MethyLight®" refers to the art-recognized fluorescence-based real-time PCR technique described by Eads et al., *Cancer Res.* 59:2302-2306, 1999.

The term "HeavyMethy™" assay, in the embodiment thereof implemented herein, refers to a HeavyMethyl MethylLight® assay, which is a variation of the MethylLight® assay, wherein the MethylLight® assay is combined with methylation specific blocking probes covering CpG positions between the amplification primers.

The term "Ms-SNuPE" (Methylation-sensitive Single Nucleotide Primer Extension) refers to the art-recognized assay described by Gonzalgo & Jones, *Nucleic Acids Res.* 25:2529-2531, 1997.

The term "MSP" (Methylation-specific PCR) refers to the art-recognized methylation assay described by Herman et al. *Proc. Natl. Acad. Sci. USA* 93:9821-9826, 1996, and by U.S. Pat. No. 5,786,146.

The term "COBRA" (Combined Bisulfite Restriction Analysis) refers to the art-recognized methylation assay described by Xiong & Laird, Nucleic Acids Res. 25:2532-2534, 1997.

The term "MCA" (Methylated CpG Island Amplification) refers to the methylation assay described by Toyota et al., *Cancer Res.* 59:2307-12, 1999, and in WO 00/26401A1.

The term "hybridization" is to be understood as a bond of an oligonucleotide to a complementary sequence along the lines of the Watson-Crick base pairings in the sample DNA, forming a duplex structure.

"Stringent hybridization conditions," as defined herein, involve hybridizing at 68° C. in 5×SSC/5×Denhardt's solution/1.0% SDS, and washing in 0.2×SSC/0.1% SDS at room temperature, or involve the art-recognized equivalent thereof (e.g., conditions in which a hybridization is carried out at 60° C. in 2.5×SSC buffer, followed by several washing steps at 37° C. in a low buffer concentration, and remains stable). Moderately stringent conditions, as defined herein, involve including washing in 3×SSC at 42° C., or the art-recognized equivalent thereof. The parameters of salt concentration and temperature can be varied to achieve the optimal level of identity between the probe and the target nucleic acid. Guidance regarding such conditions is available in the art, for example, by Sambrook et al., 1989, Molecular Cloning, A Laboratory Manual, Cold Spring Harbor Press, N. Y.; and Ausubel et al. (eds.), 1995, Current Protocols in Molecular Biology, (John Wiley & Sons, N. Y.) at Unit 2.10.

The term 'primary' when used in reference to cancer or other cell proliferative disorder shall be taken to mean the first to develop.

The term 'metastasis' as used herein shall be taken to mean the transfer of a disease-producing agent (such as bacteria, cancer or other cell proliferative disorder cells) from an original site of disease to another part of the body with development of a similar lesion in the new location.

Overview:

Despite intensive efforts to improve screening and early detection of colon cell proliferative disorders, most cases are diagnosed in an advanced stage with regional or distant metastasis which are associated with poor survival. The herein described invention discloses epigenetic markers that have novel utility for the analysis of colon cell proliferative disorders, combined with sensitive assay methods for the improved detection of said disorders. The invention presents improvements over the state of the art in that it provides a means for the detection of colon cell proliferative disorders by analysis of a gene panel, with a high sensitivity and specificity. The invention presents further improvements in that the 'gene panel' consists of at least one of seven genes and/or their regulatory sequences, thereby enabling a highly sensitive and specific but time and cost effective analysis. The invention further discloses particularly preferred combinations of said seven genes.

In one aspect, the present invention provides for the improved detection of colorectal carcinomas by determination of the methylation status of CpG dinucleotide sequences of the gene ALX4 and/or its regulatory sequences. In a further aspect the invention provides a further preferred means for the detection of colorectal carcinomas by determination of the methylation status of CpG dinucleotide sequences of the gene ALX4 and at least one gene selected from the group consisting TPEF, p16/INK4A, APC, caveolin-2, DAPK and TIMP3 and/or their regulatory sequences.

In one aspect, the present invention provides for the use of the bisulfite technique, in combination with one or more methylation assays, for determination of the methylation status of CpG dinucleotide sequences of at least two genes taken from the group consisting ALX4, TPEF, p16/INK4A, APC, caveolin-2, DAPK and TIMP3 and/or their regulatory sequences. It is particularly preferred that one of the genes is ALX4. According to the present invention, determination of the methylation status of CpG dinucleotide sequences within at least two members of said group of genes has diagnostic and prognostic utility. It is a further aspect of the invention that the analysed genomic sequences of the group consisting the group consisting ALX4, TPEF, p16/INK4A, APC, caveolin-2, DAPK and TIMP3 and/or their regulatory sequences are selected from the sequence listing (see Table 2).

In a further aspect the present invention provides a selection of genes consisting ALX4, TPEF and p16. Two or more of these genes are analysed in the form of a 'gene panel'. It is particularly preferred that one of the genes is ALX4. It is a further aspect of the invention that the analysed genomic sequences are selected from the group consisting of ALX4, TPEF and p16 and/or their regulatory sequences are selected from the sequence listing (see Table 2).

Particular embodiments of the present invention provide a novel application of the analysis of methylation levels and/or patterns within said sequences that enables a precise detection, classification, treatment and overall prognosis of colon cell proliferative disorders. Early detection of colon cell proliferative disorders is directly linked with disease prognosis, and the disclosed method thereby enables the physician and patient to make better and more informed treatment decisions.

More Particularly:

The present invention provides improved means for the detection of colorectal cell proliferative disorders. This aim is achieved by the analysis of the CpG methylation status of genes selected from the group consisting ALX4, TPEF, p16/INK4A, APC, caveolin-2, DAPK and TIMP3 and/or their regulatory sequences.

In a further aspect, the present invention achieves said goal by analysis of the methylation status of at least one CpG position of the gene ALX4 and/or its regulatory sequences. In a further aspect the aim of the invention is achieved by the methylation analysis of said gene, ALX4 and/or its regulatory sequences and one or more genes selected from the group consisting TPEF, p16/INK4A, APC, caveolin-2, DAPK and TIMP3 and/or their regulatory sequences.

The present invention is further based upon the analysis of methylation levels within two or more genes taken from the group consisting of ALX4, TPEF, p16/INK4A, APC, caveolin-2, DAPK and TIMP3 and/or their regulatory sequences.

Accordingly, the invention also disclose the genomic sequences of said genes in SEQ ID NO: 1 TO SEQ ID NO: 4 AND SEQ ID NO:45 TO SEQ ID NO:47, according to table 2.

Additional embodiments provide modified variants of SEQ ID NOS:1 to SEQ ID NO:4 and SEQ ID NOS:45 to SEQ ID NO:47, as well as oligonucleotides and/or PNA-oligomers for analysis of cytosine methylation patterns within SEQ ID NO:1 to SEQ ID NO:4 and SEQ ID NO:45 to SEQ ID NO:47.

According to the present invention hypermethylation of the genes ALX4, TPEF, p16/INK4A, APC, caveolin-2, DAPK and TIMP3 and/or their regulatory sequences is correlated with varying degrees of probability to the presence of colon cell proliferative disorders, and or metastases thereof. The present invention discloses the analysis of methylation within said genes and/or their regulatory sequences in the form of a panel enabling the improved detection, classification, treatment and overall prognosis of colon cell proliferative disorders. Aberrant methylation of the genes TPEF, p16/INK4A, APC, caveolin-2, DAPK and TIMP3 have to date been associated with the development of colorectal cell proliferative disorders. The present invention provides specific combinations of these genes which were determined to be particularly useful for the detection of colorectal cell proliferative disorders as measured by sensitivity and specificity of detection. Furthermore the invention provides CpG methylation analysis of the gene ALX4, with specific and novel utility for the detection of colorectal cell proliferative disorders. Methylation analysis of this gene is herein shown to have the surprising effect of being a highly sensitive and specific colorectal cancer detection marker. Furthermore the sensitivity and specificity of this detection is improved by a combined analysis of the gene ALX4 and one or more genes selected from the group consisting of TPEF, p16/INK4A, APC, caveolin-2, DAPK and TIMP3.

Wherein the object of the analysis is the detection of colon cell proliferative disorders it is particularly preferred that the methylation of two or more genes selected from the group consisting of ALX4, TPEF, p16/INK4A, APC, caveolin-2, DAPK and TIMP3 and/or their regulatory sequences are analysed. It is particularly preferred that said genes are selected from the group consisting of ALX4, TPEF and p16 and/or their regulatory sequences are analysed. It is further preferred that the methylation of all of the genes of the group consisting ALX4, TPEF and p16 and/or their regulatory sequences are analysed. In an alternative embodiment the methylation of the gene ALX4 only is analysed. In a further preferred alternative embodiment the CpG methylation status of the gene ALX4 and/or its regulatory sequences and one or more genes selected from the group consisting of TPEF, p16/INK4A, APC, caveolin-2, DAPK and TIMP3 and/or their regulatory sequences are analysed.

An objective of the invention comprises analysis of the methylation state of two or more CpG dinucleotides within at least two of the genomic sequences selected from the group consisting of SEQ ID NOS: 1 to SEQ ID NO: 4 and SEQ ID NOS: 45 to SEQ ID NO: 47 and sequences complementary thereto.

It is preferred that the methylation of two or more sequences selected from the group consisting SEQ ID NOS: 2, 3 and 4 are analysed. In this embodiment of the invention it is particularly preferred that the methylation of all of the sequences of the group consisting SEQ ID NOS: 2, 3 and 4 are analysed.

In an alternative embodiment the methylation status of at least one CpG position of SEQ ID NO: 2 only is analysed. In a further preferred alternative embodiment the CpG methylation status of SEQ ID NO: 2 and one or more sequences selected from the group consisting SEQ ID NOS:1, 3, 4 and SEQ ID NOS:45 to SEQ ID NO:47 and sequences complementary thereto are analysed. In a further preferred alternative embodiment the CpG methylation status of SEQ ID NO:2 and one or more sequences selected from the group consisting SEQ ID NOS: 1, 3 and 4 and sequences complementary thereto are analysed.

The disclosed invention provides treated nucleic acids, derived from genomic SEQ ID NOS:1 to SEQ ID NO:4 and SEQ ID NOS:45 to SEQ ID NO:47, wherein the treatment is suitable to convert at least one unmethylated cytosine base of the genomic DNA sequence to uracil or another base that is detectably dissimilar to cytosine in terms of hybridization. The genomic sequences in question may comprise one, or more, consecutive or random methylated CpG positions. Said treatment preferrably comprises use of a reagent selected from the group consisting of bisulfite, hydrogen sulfite, disulfite, and combinations thereof. In a preferred embodiment of the invention, the objective comprises analysis of at least two modified nucleic acid comprising a sequence of at least 16 contiguous nucleotide bases in length of a sequence selected from the group consisting of SEQ ID NO: 5 TO SEQ ID NO: 20 & SEQ ID NO: 48 TO SEQ ID NO: 59, wherein said sequence comprises at least one CpG, TpA or CpA dinucleotide and sequences complementary thereto. The sequences of SEQ ID NOS: 7 to SEQ ID NO:12 and SEQ ID NOS:15 to SEQ ID NO:20 provide modified versions of the nucleic acid according to SEQ ID NOS:2 to SEQ ID NO:4, wherein the modification of each genomic sequence results in the synthesis of a nucleic acid having a sequence that is unique and distinct from said genomic sequence as follows. For each sense strand genomic DNA, e.g., SEQ ID NO:1, four converted versions are disclosed. A first version wherein "C" is converted to "T," but "CpG" remains "CpG" (i.e., corresponds to case where, for the genomic sequence, all "C" residues of CpG dinucleotide sequences are methylated and are thus not converted); a second version discloses the complement of the disclosed genomic DNA sequence (i.e. antisense strand), wherein "C" is converted to "T," but "CpG" remains "CpG" (i.e., corresponds to case where, for all "C" residues of CpG dinucleotide sequences are methylated and are thus not converted). The 'upmethylated' converted sequences of SEQ ID NOS:1 to SEQ ID NO:4 and SEQ ID NOS:45 to SEQ ID NO:47 correspond to SEQ ID NOS:5 to SEQ ID NO:12 and SEQ ID NOS:48 to SEQ ID NO:53 (see TABLE 2). A third chemically converted version of each genomic sequences is provided, wherein "C" is converted to "T" for all "C" residues, including those of "CpG" dinucleotide sequences (i.e., corresponds to case where, for the genomic sequences, all "C" residues of CpG dinucleotide sequences are unmethylated); a final chemically converted version of each sequence, discloses the complement of the disclosed genomic DNA sequence (i.e. antisense strand), wherein "C" is converted to "T" for all "C" residues, including those of "CpG" dinucleotide sequences (i.e., corresponds to case where, for the complement (antisense strand) of each genomic sequence, all "C" residues of CpG dinucleotide sequences are umethylated). The 'downmethylated' converted sequences of SEQ ID NOS: 1 to SEQ ID NO:4 and SEQ ID NOS:45 to SEQ ID NO:47 correspond to SEQ ID NOS:13 to SEQ ID NO:20 and SEQ ID NOS:54 to SEQ ID NO:59.

Particularly useful for the detection of colon cell proliferative disorders, and heretofore undisclosed are the non-naturally occurring sequences according to SEQ ID NOS:7, 8, 15 and 16, which correspond to methylation-specific converted sequences of part of the gene ALX4 (SEQ ID NO:2).

In an alternative preferred embodiment, such analysis comprises the use of an oligonucleotide or oligomer for detecting the cytosine methylation state within genomic or pretreated (chemically modified) DNA, according to SEQ ID NOS:1 to SEQ ID NO:4 and SEQ ID NOS:48 to SEQ ID NO:59. Said oligonucleotide or oligomer comprising a nucleic acid sequence having a length of at least nine (9) nucleotides which hybridizes, under moderately stringent or stringent conditions (as defined herein above), to a pretreated nucleic acid sequence according to SEQ ID NOS:5 to SEQ ID NO:20 & SEQ ID NOS:48 to SEQ ID NO:59 and/or sequences complementary thereto, or to a genomic sequence according to SEQ ID NOS:1 to SEQ ID NO:4 and SEQ ID NOS:45 to SEQ ID NO:47 and/or sequences complementary thereto.

Thus, the present invention includes nucleic acid molecules (e.g., oligonucleotides and peptide nucleic acid (PNA) molecules (PNA-oligomers)) that hybridize under moderately stringent and/or stringent hybridization conditions to all or a portion of the sequences SEQ ID NOS:1 to SEQ ID NO:20, or to the complements thereof. The hybridizing portion of the hybridizing nucleic acids is typically at least 9, 15, 20, 25, 30 or 35 nucleotides in length. However, longer molecules have inventive utility, and are thus within the scope of the present invention.

Preferably, the hybridizing portion of the inventive hybridizing nucleic acids is at least 95%, or at least 98%, or 100% identical to the sequence, or to a portion thereof of SEQ ID NOS:1 to SEQ ID NO:20, or to the complements thereof.

Hybridizing nucleic acids of the type described herein can be used, for example, as a primer (e.g., a PCR primer), or a diagnostic and/or prognostic probe or primer. Preferably, hybridization of the oligonucleotide probe to a nucleic acid sample is performed under stringent conditions and the probe is 100% identical to the target sequence. Nucleic acid duplex or hybrid stability is expressed as the melting temperature or Tm, which is the temperature at which a probe dissociates from a target DNA. This melting temperature is used to define the required stringency conditions.

For target sequences that are related and substantially identical to the corresponding sequence of SEQ ID NOS:1 to SEQ ID NO:4 and SEQ ID NOS:45 to SEQ ID NO:47 (such as allelic variants and SNPS), rather than identical, it is useful to first establish the lowest temperature at which only homologous hybridization occurs with a particular concentration of salt (e.g., SSC or SSPE). Then, assuming that 1% mismatching results in a 1° C. decrease in the Tm, the temperature of the final wash in the hybridization reaction is reduced accordingly (for example, if sequences having >95% identity with the probe are sought, the final wash temperature is decreased by 5° C.). In practice, the change in Tm can be between 0.5° C. and 1.5° C. per 1% mismatch.

Examples of inventive oligonucleotides of length X (in nucleotides), as indicated by polynucleotide positions with reference to, e.g., SEQ ID NO: 1, include those corresponding to sets (sense and antisense sets) of consecutively overlapping oligonucleotides of length X, where the oligonucleotides within each consecutively overlapping set (corresponding to a given X value) are defined as the finite set of Z oligonucleotides from nucleotide positions:

n to (n+(X−1));

where n=1, 2, 3, . . . (Y−(X−1));

where Y equals the length (nucleotides or base pairs);

where X equals the common length (in nucleotides) of each oligonucleotide in the set (e.g., X=20 for a set of consecutively overlapping 20-mers); and where the number (Z) of consecutively overlapping oligomers of length X for a given SEQ ID NO of length Y is equal to Y−(X−1).

Preferably, the set is limited to those oligomers that comprise at least one CpQ TpG or CpA dinucleotide.

Examples of inventive 20-mer oligonucleotides within a sequence of length 2470 base pairs include the following set of 2470 oligomers (and the antisense set complementary thereto), indicated by polynucleotide positions 1-20, 2-21, 3-22, 4-23, 5-24 . . . 2451-2470.

Preferably, the set is limited to those oligomers that comprise at least one CpG, TpG or CpA dinucleotide.

The present invention encompasses, for each of SEQ ID NO: 1 to SEQ ID NO: 20 and SEQ ID NO: 45 to SEQ ID NO: 59 (sense and antisense), multiple consecutively overlapping sets of oligonucleotides or modified oligonucleotides of length X, where, e.g., X=9, 10, 17, 20, 22, 23, 25, 27, 30 or 35 nucleotides.

The oligonucleotides or oligomers according to the present invention constitute effective tools useful to ascertain genetic and epigenetic parameters of the genomic sequence corresponding to SEQ ID NOS:1 to SEQ ID NO:4 and SEQ ID NOS:45 to SEQ ID NO 47. Preferred sets of such oligonucleotides or modified oligonucleotides of length X are those consecutively overlapping sets of oligomers corresponding to SEQ ID NO:1 to SEQ ID NO:20 (and to the complements thereof). Preferably, said oligomers comprise at least one CpG, TpG or CpA dinucleotide.

Particularly preferred oligonucleotides or oligomers according to the present invention are those in which the cytosine of the CpG dinucleotide (or of the corresponding converted TpG or CpA dinculeotide) sequences is within the middle third of the oligonucleotide; that is, where the oligonucleotide is, for example, 13 bases in length, the CpG, TpG or CpA dinucleotide is positioned within the fifth to ninth nucleotide from the 5'-end.

The oligonucleotides of the invention can also be modified by chemically linking the oligonucleotide to one or more moieties or conjugates to enhance the activity, stability or detection of the oligonucleotide. Such moieties or conjugates include chromophores, fluorophors, lipids such as cholesterol, cholic acid, thioether, aliphatic chains, phospholipids, polyamines, polyethylene glycol (PEG), palmityl moieties, and others as disclosed in, for example, U.S. Pat. Nos. 5,514,758, 5,565,552, 5,567,810, 5,574,142, 5,585,481, 5,587,371, 5,597,696 and 5,958,773. The probes may also exist in the form of a PNA (peptide nucleic acid) which has particularly p referred pairing properties. Thus, the oligonucleotide may include other appended groups such as peptides, and may include hybridization-triggered cleavage agents (Krol et al., *BioTechniques* 6:958-976, 1988) or intercalating agents (Zon, *Pharm. Res.* 5:539-549, 1988). To this end, the oligonucleotide may be conjugated to another molecule, e.g., a chromophore, fluorophor, peptide, hybridization-triggered cross-linking agent, transport agent, hybridization-triggered cleavage agent, etc.

The oligonucleotide may also comprise at least one art-recognized modified sugar and/or base moiety, or may comprise a modified backbone or non-natural internucleoside linkage.

The oligonucleotides or oligomers according to particular embodiments of the present invention are typically used in 'sets, ' which contain at least one oligomer for analysis of each of the CpG dinucleotides of genomic sequence SEQ ID NO: 2 to SEQ ID NO: 4 and sequences complementary thereto, or to the corresponding CpG, TpG or CpA dinucleotide within a sequence of the pretreated nucleic acids according to SEQ ID NOS:7 to SEQ ID NO:12 and SEQ ID NOS:15 to SEQ ID NO:20 and sequences complementary thereto. In a further preferred embodiment the set comprises contain at least one oligomer for analysis of each of the CpG dinucleotides of genomic sequence SEQ ID NO:2 and sequences complementary thereto, or to the corresponding CpG, TpG or CpA dinucleotide within a sequence of the pretreated nucleic acids according to SEQ ID NOS: 7, 8, 15 and 16.

However, it is anticipated that for economic or other factors it may be preferable to analyze a limited selection of the CpG dinucleotides within said sequences, and the content of the set of oligonucleotides is altered accordingly.

Therefore, in particular embodiments, the present invention provides a set of at least two (2) (oligonucleotides and/or PNA-oligomers) useful for detecting the cytosine methylation state in pretreated genomic DNA of at least two genes selected from ALX4, TPEF and p16 (SEQ ID NOS:7 to SEQ ID NO:12 and SEQ ID NOS:15 to SEQ ID NO:20), or in genomic DNA (SEQ ID NOS:2 to SEQ ID NO:4 and sequences complementary thereto). In a further preferred embodiment the set comprises at least two oligonucleotides for the analysis of CpG positions within one or more of SEQ ID NOS:7, 8, 15 and 16.

These probes enable diagnosis, classification and/or therapy of genetic and epigenetic parameters of colon cell proliferative disorders. The set of oligomers may also be used for detecting single nucleotide polymorphisms (SNPs) in pretreated genomic DNA (SEQ ID NOS:7 to SEQ ID NO:12 and SEQ ID NOS:15 to SEQ ID NO:20), or in genomic DNA (SEQ ID NOS:2 to SEQ ID NO:4 and sequences complementary thereto).

In preferred embodiments, at least one, and more preferably all members of a set of oligonucleotides is bound to a solid phase.

In further embodiments, the present invention provides a set of at least two (2) oligonucleotides that are used as 'primer' oligonucleotides for amplifying DNA sequences of one of SEQ ID NOS:5 to SEQ ID NO:20 and SEQ ID NOS:48 to SEQ ID NO:49 and sequences complementary thereto, or segments thereof.

It is anticipated that the oligonucleotides may constitute all or part of an "array" or "DNA chip" (i.e., an arrangement of different oligonucleotides and/or PNA-oligomers bound to a solid phase). Such an array of different oligonucleotide- and/or PNA-oligomer sequences can be characterized, for example, in that it is arranged on the solid phase in the form of a rectangular or hexagonal lattice. The solid-phase surface may be composed of silicon, glass, polystyrene, aluminum, steel, iron, copper, nickel, silver, or gold. Nitrocellulose as well as plastics such as nylon, which can exist in the form of pellets or also as resin matrices, may also be used. An overview of the Prior Art in oligomer array manufacturing can be gathered from a special edition of Nature Genetics (*Nature Genetics Supplement*, Volume 21, January 1999, and from the literature cited therein). Fluorescently labeled probes are often used for the scanning of immobilized DNA arrays. The simple attachment of Cy3 and Cy5 dyes to the 5'—OH of the specific probe are particularly suitable for fluorescence labels. The detection of the fluorescence of the hybridized probes may be carried out, for example, via a confocal microscope. Cy3 and Cy5 dyes, besides many others, are commercially available.

It is particularly preferred that the oligomers according to the invention are utilised for the detection of colorectal carcinoma.

The present invention further provides a method for ascertaining genetic and/or epigenetic parameters of the genes ALX4, TPEF, p16, APC, TIMP3, Dapk and Caveolin 2 and/or their regulatory sequences within a subject by analyzing cytosine methylation and single nucleotide polymorphisms.

It is preferred that the methylation of two or more genes selected from the group consisting of the genes ALX4, TPEF, p16, APC, TIMP3, Dapk and Caveolin 2 and/or their regulatory sequences are analysed. In this embodiment of the invention it is particularly preferred that the methylation of all of the genes of the group consisting ALX4, TPEF and p16 and/or their regulatory sequences are analysed.

In a further embodiment of the method it is preferred that only the methylation status of the gene ALX4 and/or its regulatory sequences is analysed. In a further preferred embodiment the methylation status of the gene ALX4 and/or its regulatory sequences and one or more of the group consisting TPEF, p16, APC, TIMP3, Dapk and Caveolin 2 and/or their regulatory sequences are analysed. In a further preferred embodiment the methylation status of the gene ALX4 and/or its regulatory sequences and one or both of the group consisting TPEF and p16 and/or their regulatory sequences are analysed.

Accordingly, it is preferred that the methylation of two or more genetic sequences selected from the group consisting SEQ ID NOS: 2,3 and 4 and/or their regulatory sequences are analysed. In this embodiment of the invention it is particularly preferred that the methylation of all of the genes of the group consisting SEQ ID NOs: 2,3 & 4 and/or their regulatory sequences are analysed.

In a further embodiment of the method it is preferred that only the methylation status of SEQ ID 2 is analysed. In a further preferred embodiment the methylation status of SEQ ID 2 and one or more of the group consisting SEQ ID NOS: 3, 4, 45-47 are analysed. In a further preferred embodiment the methylation status of SEQ ID NO:2 and one or both of SEQ ID NOS:3 and 4 are analysed.

Said method comprising contacting a nucleic acid comprising one or more of SEQ ID NOS:1 to SEQ ID NO:4 and SEQ ID NOS:45 to SEQ ID NO:47 in a biological sample obtained from said subject with at least one reagent or a series of reagents, wherein said reagent or series of reagents, distinguishes between methylated and non-methylated CpG dinucleotides within the target nucleic acid.

It is preferred that the methylation of two or more genetic sequences select analysed. In this embodiment of the invention it is particularly preferred that the methylation of all of the genes of the group consisting SEQ ID NOS:2, 3 and 4 and/or their regulatory sequences are analysed.

In a further embodiment of the method it is preferred that only the methylation status of SEQ ID 2 is analysed. In a further preferred embodiment the methylation status of SEQ ID NO:2 and one or more of the group consisting SEQ ID NOs:3, 4 45-47 are analysed. In a further preferred embodiment the methylation status of SEQ ID NO:2 and one or both of SEQ ID NOS:3 and 4 are analysed.

Said method comprising contacting a nucleic acid comprising the appropriate gene(s) and/or one or more of SEQ ID NOS:1 to SEQ ID NO:4 and SEQ ID NOS:45 to SEQ ID NO:47 in a biological sample obtained from said subject with at least one reagent or a series of reagents, wherein said reagent or series of reagents, distinguishes between methylated and non-methylated CpG dinucleotides within the target nucleic acid.

Preferably, said method comprises the following steps: In the first step, a sample of the tissue to be analysed is obtained. The source may be any suitable source, such as cell lines, histological slides, biopsies, tissue embedded in paraffin, bodily fluids, stool, blood and all possible combinations thereof. Genomic DNA is then isolated from said biological sample, this may be by any means standard in the art, including the use of commercially available kits. Briefly, wherein the DNA of interest is encapsulated in by a cellular membrane the biological sample must be disrupted and lysed by enzymatic, chemical or mechanical means. The DNA solution may then be cleared of proteins and other contaminants, e.g., by digestion with proteinase K. The genomic DNA is then recovered from the solution. This may be carried out by means of a variety of methods including salting out, organic extraction or binding of the DNA to a solid phase support. The choice of method will be affected by several factors including time, expense and required quantity of DNA.

Once the nucleic acids have been extracted, the genomic double stranded DNA is used in the analysis.

In the second step of the method, the genomic DNA sample is treated in such a manner that cytosine bases which are unmethylated at the 5'-position are converted to uracil, thymine, or another base which is dissimilar to cytosine in terms of hybridization behavior. This will be understood as 'pretreatment' herein.

The above described treatment of genomic DNA is preferably carried out with bisulfite (hydrogen sulfite, disulfite) and subsequent alkaline hydrolysis which results in a conversion of non-methylated cytosine nucleobases to uracil or to another base which is dissimilar to cytosine in terms of base pairing behavior.

In the third step of the method, fragments of the pretreated DNA are amplified, using sets of primer oligonucleotides according to the present invention, and an amplification enzyme. The amplification of several DNA segments can be carried out simultaneously in one and the same reaction vessel. Typically, the amplification is carried out using a polymerase chain reaction (PCR). The set of primer oligonucleotides includes at least two oligonucleotides whose sequences are each reverse complementary, identical, or hybridize under stringent or highly stringent conditions to an at least 16-base-pair long segment of the base sequences of one or more of SEQ ID NOS:7 to SEQ ID NO:12 and SEQ ID NOS:15 to SEQ ID NO:20 and sequences complementary thereto.

It is preferred that said set of primer oligonucleotides includes at least two oligonucleotides whose sequences are each reverse complementary, identical, or hybridize under stringent or highly stringent conditions to an at least 16-base-pair long segment of the base sequences of one or more of SEQ ID NOS:7-12 and 15-20. In this embodiment of the invention it is particularly preferred that said set consists of at least two oligonucleotides whose sequences are each reverse complementary, identical, or hybridize under stringent or highly stringent conditions to an at least 16-base-pair long segment of the base sequences of SEQ ID NOS:5-20 and 48-59.

It is also preferred that said set of primer oligonucleotides includes at least two oligonucleotides whose sequences are each reverse complementary, identical, or hybridize under stringent or highly stringent conditions to an at least 16-base-pair long segment of the base sequences of one or more of SEQ ID NOS:7-12 and 15-20.

It is also preferred that said set of primer oligonucleotides includes at least two oligonucleotides whose sequences are each reverse complementary, identical, or hybridize under stringent or highly stringent conditions to an at least 16-base-pair long segment of the base sequences of at least one of SEQ ID NOS:7, 8, 15 or 16. It is also preferred that said set of primer oligonucleotides includes at least two oligonucleotides whose sequences are each reverse complementary, identical, or hybridize under stringent or highly stringent conditions to an at least 16-base-pair long segment of the base sequences of at least one of SEQ ID NOS:7, 8, 15 or 16, and a further pair of oligonucleotides whose sequences are each reverse complementary, identical, or hybridize under stringent or highly stringent conditions to an at least 16-base-pair long segment of the base sequences of at least one of SEQ ID NOS:9-12 and 17-20.

In an alternate embodiment of the method, the methylation status of preselected CpG positions within the nucleic acid sequences comprising one or more of SEQ ID NOS:1 to SEQ ID NO:4 and SEQ ID NOS:45 to SEQ ID NO:47 may be detected by use of methylation-specific primer oligonucleotides. This technique (MSP) has been described in U.S. Pat. No. 6,265,171 to Herman. The use of methylation status specific primers for the amplification of bisulfite treated DNA allows the differentiation between methylated and unmethylated nucleic acids. MSP primers pairs contain at least one primer which hybridizes to a bisulfite treated CpG dinucleotide. Therefore, the sequence of said primers comprises at least one CpG dinucleotide. MSP primers specific for non-methylated DNA contain a "T" at the 3' position of the C position in the CpG Preferably, therefore, the base sequence of said primers is required to comprise a sequence having a length of at least 9 nucleotides which hybridizes to a pretreated nucleic acid sequence according to one of SEQ ID NOS:5 to SEQ ID NO:20 and SEQ ID NOS:48 to SEQ ID NO:59 and sequences complementary thereto, wherein the base sequence of said oligomers comprises at least one CpG dinucleotide.

It is preferred that said set of MSP primer oligonucleotides includes at least two oligonucleotides whose sequences comprise a sequence having a length of at least 9 nucleotides which hybridizes to a pretreated nucleic acid sequence according to one or more of SEQ ID NOS:7-12, 15-20 and 49-59.

In this embodiment of the invention it is particularly preferred that said set consists of at least two MSP primer oligonucleotides whose sequences are each reverse complementary, identical, or hybridize under stringent or highly stringent conditions to an at least 16-base-pair long segment of the base sequences of SEQ ID NOS:7-12 and 15-20.

In a further embodiment of the invention it is particularly preferred that said set consists of at least two MSP primer oligonucleotides whose sequences are each reverse complementary, identical, or hybridize under stringent or highly stringent conditions to an at least 16-base-pair long segment of at least one of the base sequences of SEQ ID NOS:7, 8, 15 and 16. In a further preferred embodiment of this method it is preferred that said set consists of at least two MSP primer oligonucleotides whose sequences are each reverse complementary, identical, or hybridize under stringent or highly stringent conditions to an at least 16-base-pair long segment of at least one of the base sequences of SEQ ID NOS:7, 8, 15 and 16 and one or more sequences taken from the group consisting SEQ ID NOS:9-12, 17-20 and 48-59.

A further preferred embodiment of the method comprises the use of blocker oligonucleotides. The use of such blocker oligonucleotides has been described by Yu et al., *BioTechniques* 23:714-720, 1997. Blocking probe oligonucleotides are hybridized to the bisulfite treated nucleic acid concurrently with the PCR primers. PCR amplification of the nucleic acid is terminated at the 5' position of the blocking probe, such that amplification of a nucleic acid is suppressed where the complementary sequence to the blocking probe is present. The probes may be designed to hybridize to the bisulfite treated nucleic acid in a methylation status specific manner. For example, for detection of methylated nucleic acids within a population of unmethylated nucleic acids, suppression of the amplification of nucleic acids which are unmethylated at the position in question would be carried out by the use of blocking probes comprising a 'CpA' or 'TpA' at the position in question, as opposed to a 'CpG' if the suppression of amplification of methylated nucleic acids is desired.

For PCR methods using blocker oligonucleotides, efficient disruption of polymerase-mediated amplification requires that blocker oligonucleotides not be elongated by the polymerase. Preferably, this is achieved through the use of blockers that are 3'-deoxyoligonucleotides, or oligonucleotides derivitized at the 3' position with other than a "free" hydroxyl group. For example, 3'—O-acetyl oligonucleotides are representative of a preferred class of blocker molecule.

Additionally, polymerase-mediated decomposition of the blocker oligonucleotides should be precluded. Preferably, such preclusion comprises either use of a polymerase lacking 5'-3' exonuclease activity, or use of modified blocker oligonucleotides having, for example, thioate bridges at the 5'-termini thereof that render the blocker molecule nuclease-resistant. Particular applications may not require such 5' modifications of the blocker. For example, if the blocker- and primer-binding sites overlap, thereby precluding binding of the primer (e.g., with excess blocker), degradation of the blocker oligonucleotide will be substantially precluded. T his is because the polymerase will not extend the primer toward, and through (in the 5'-3' direction) the blocker—a process that normally results in degradation of the hybridized blocker oligonucleotide.

A particularly preferred blocker/PCR embodiment, for purposes of the present invention and as implemented herein, comprises the use of peptide nucleic acid (PNA) oligomers as blocking oligonucleotides. Such PNA blocker oligomers are ideally suited, because they are neither decomposed nor extended by the polymerase.

Preferably, therefore, the base sequence of said blocking oligonucleotides is required to comprise a sequence having a length of at least 9 nucleotides which hybridizes to a pretreated nucleic acid sequence according to one of SEQ ID NOS:5 to SEQ ID NO:20 and SEQ ID NOS:48 to SEQ ID NO:59 and sequences complementary thereto, wherein the base sequence of said oligonucleotides comprises at least one CpG TpG or CpA dinucleotide.

It is preferred that said set of blocking oligonucleotides includes at least two oligonucleotides whose sequences comprise a sequence having a length of at least 9 nucleotides which hybridizes to a pretreated nucleic acid sequence according to one or more of SEQ ID NOS:7-12 and 15-20. In this embodiment of the invention it is particularly preferred that said set consists of at least one blocker oligonucleotides whose sequences are each reverse complementary, identical, or hybridize under stringent or highly stringent conditions to an at least 9-base-pair long segment of the base sequences of each of SEQ ID NOS:7-12 and 15-20.

In a further embodiment it is preferred that said set of blocking oligonucleotides includes at least two oligonucleotides whose sequences comprise a sequence having a length of at least 9 nucleotides which hybridizes to a pretreated nucleic acid sequence according to one or more of SEQ ID NOS:7, 8, 15 & 16. In this embodiment of the invention it is particularly preferred that said set further consists of at least one blocker oligonucleotides whose sequences are each reverse complementary, identical, or hybridize under stringent or highly stringent conditions to an at least 9-base-pair long segment of the base sequences of each of SEQ ID NOS: 9-12, 17-20 & 48-59. In this embodiment it is further preferred that said base sequences are selected from SEQ ID NOS:9-12 and 17-20.

The fragments obtained by means of the amplification can carry a directly or indirectly detectable label. Preferred are labels in the form of fluorescence labels, radionuclides, or detachable molecule fragments having a typical mass which can be detected in a mass spectrometer. Where said labels are mass labels, it is preferred that the labeled amplificates have a single positive or negative net charge, allowing for better detectability in the mass spectrometer. The detection may be carried out and visualized by means of, e.g., matrix assisted laser desorption/ionization mass spectrometry (MALDI) or using electron spray mass spectrometry (ESI).

Matrix Assisted Laser Desorption/Ionization Mass Spectrometry (MALDI-TOF) is a very efficient development for the analysis of biomolecules (Karas & Hillenkamp, *Anal Chem.,* 60:2299-301, 1988). An analyte is embedded in a light-absorbing matrix. The matrix is evaporated by a short laser pulse thus transporting the analyte molecule into the vapour phase in an unfragmented manner. The analyte is ionized by collisions with matrix molecules. An applied voltage accelerates the ions into a field-free flight tube. Due to their different masses, the ions are accelerated at different rates. Smaller ions reach the detector sooner than bigger ones. MALDI-TOF spectrometry is well suited to the analysis of peptides and proteins. The analysis of nucleic acids is somewhat more difficult (Gut & Beck, *Current Innovations and*

*Future Trends,* 1:147-57, 1995). The sensitivity with respect to nucleic acid analysis is approximately 100-times less than for peptides, and decreases disproportionally with increasing fragment size. Moreover, for nucleic acids having a multiply negatively charged backbone, the ionization process via the matrix is considerably less efficient. In MALDI-TOF spectrometry, the selection of the matrix plays an eminently important role. For desorption of peptides, several very efficient matrixes have been found which produce a very fine crystallisation. There are now several responsive matrixes for DNA, however, the difference in sensitivity between peptides and nucleic acids has not been reduced. This difference in sensitivity can be reduced, however, by chemically modifying the DNA in such a manner that it becomes more similar to a peptide. For example, phosphorothioate nucleic acids, in which the usual phosphates of the backbone are substituted with thiophosphates, can be converted into a charge-neutral DNA using simple alkylation chemistry (Gut & Beck, *Nucleic Acids Res.* 23: 1367-73, 1995). The coupling of a charge tag to this modified DNA results in an increase in MALDI-TOF sensitivity to the same level as that found for peptides. A further advantage of charge tagging is the increased stability of the analysis against impurities, which makes the detection of unmodified substrates considerably more difficult.

In the fourth step of the method, the amplificates obtained during the third step of the method are analysed in order to ascertain the methylation status of the CpG dinucleotides prior to the treatment.

In embodiments where the amplificates were obtained by means of MSP amplification, the presence or absence of an amplificate is in itself indicative of the methylation state of the CpG positions covered by the primer, according to the base sequences of said primer.

Amplificates obtained by means of both standard and methylation specific PCR may be further analyzed by means of hybridization-based methods such as, but not limited to, array technology and probe based technologies as well as by means of techniques such as sequencing and template directed extension.

In one embodiment of the method, the amplificates synthesised in step three are subsequently hybridized to an array or a set of oligonucleotides and/or PNA probes. In this context, the hybridization takes place in the following manner: the set of probes used during the hybridization is preferably composed of at least 2 oligonucleotides or PNA-oligomers; in the process, the amplificates serve as probes which hybridize to oligonucleotides previously bonded to a solid phase; the non-hybridized fragments are subsequently removed; said oligonucleotides contain at least one base sequence having a length of at least 9 nucleotides which is reverse complementary or identical to a segment of the base sequences specified in the present Sequence Listing; and the segment comprises at least one CpG, TpG or CpA dinucleotide.

In a preferred embodiment, said dinucleotide is present in the central third of the oligomer. For example, wherein the oligomer comprises one CpG dinucleotide, said dinucleotide is preferably the fifth to ninth nucleotide from the 5'-end of a 13-mer. One oligonucleotide exists for the analysis of each CpG dinucleotide within the sequence according to SEQ ID NOS:1 to SEQ ID NO:4 and SEQ ID NOS:45 to SEQ ID NO:47, and the equivalent positions within SEQ ID NOS:7 to SEQ ID NO:12 and SEQ ID NOS:15 to SEQ ID NO: 20. Said oligonucleotides may also be present in the form of peptide nucleic acids. The non-hybridized amplificates are then removed. The hybridized amplificates are then detected. In this context, it is preferred that labels attached to the amplificates are identifiable at each position of the solid phase at which an oligonucleotide sequence is located.

In yet a further embodiment of the method, the genomic methylation status of the CpG positions may be ascertained by means of oligonucleotide probes that are hybridised to the bisulfite treated DNA concurrently with the PCR amplification primers (wherein said primers may either be methylation specific or standard).

A particularly preferred embodiment of this method is the use of fluorescence-based Real Time Quantitative PCR (Heid et al., *Genome Res.* 6:986-994, 1996; also see U.S. Pat. No. 6,331,393) employing a dual-labeled fluorescent oligonucleotide probe (TaqMan™ PCR, using an ABI Prism 7700 Sequence Detection System, Perkin Elmer Applied Biosystems, Foster City, Calif.). The TaqMan™ PCR reaction employs the use of a nonextendible interrogating oligonucleotide, called a TaqMan™ probe, which, in preferred embodiments, is designed to hybridize to a GpC-rich sequence located between the forward and reverse amplification primers. The TaqMan™ probe further comprises a fluorescent "reporter moiety" and a "quencher moiety" covalently bound to linker moieties (e.g., phosphoramidites) attached to the nucleotides of the TaqMan™ oligonucleotide. For analysis of methylation within nucleic acids subsequent to bisulfite treatment, it is required that the probe be methylation specific, as described in U.S. Pat. No. 6,331,393, (hereby incorporated by reference in its entirety) also known as the MethylLight™ assay. Variations on the TaqMan™ detection methodology that are also suitable for use with the described invention include the use of dual-probe technology (Lightcycler™) or fluorescent amplification primers (Sunrise™ technology). Both these techniques may be adapted in a manner suitable for use with bisulfite treated DNA, and moreover for methylation analysis within CpG dinucleotides.

A further suitable method for the u se of p robe oligonucleotides for the assessment of methylation by analysis of bisulfite treated nucleic acids In a further preferred embodiment of the method, the fifth step of the method comprises the use of template-directed oligonucleotide extension, such as MS-SNuPE as described by Gonzalgo & Jones, *Nucleic Acids Res.* 25:2529-2531, 1997.

In yet a further embodiment of the method, the fifth step of the method comprises sequencing and subsequent sequence analysis of the amplificate generated in the third step of the method (Sanger F., et al., *Proc Natl Acad Sci USA* 74:5463-5467, 1977).

Best Mode

In the most preferred embodiment of the method the nucleic acids according to SEQ ID NO: 1 to SEQ ID NO: 4 and SEQ ID NO: 45 to SEQ ID NO: 47 are isolated and treated according to the first three steps of the method outlined above, namely:

a. obtaining, from a subject, a biological sample having subject genomic DNA;
b. extracting or otherwise isolating the genomic DNA;
c. treating the genomic DNA of b), or a fragment thereof, with one or more reagents to convert cytosine bases that are unmethylated in the 5-position thereof to uracil or to another base that is detectably dissimilar to cytosine in terms of hybridization properties;

and wherein the subsequent amplification of d) is carried out in a methylation specific manner, namely by use of methylation specific primers or blocking oligonucleotides, and further wherein the detection of the amplificates is carried out by means of a real-time detection probes, as described above.

It is particularly preferred that the methylation of one or more sequences selected from the group consisting SEQ ID NOS: 2,3 and 4 are analysed. In this embodiment of the invention it is further preferred that the methylation of all of the sequences of the group consisting SEQ ID NOS: 2,3 and 4 are analysed.

In a further embodiment it is preferred that only the methylation status of SEQ ID NO:2 is analysed. In a further embodiment it is preferred that the methylation status of SEQ ID NO:2 and one or more sequences selected from the group consisting SEQ ID NOS:3, 4, 45-47 are analysed, even more preferably said group consists SEQ ID NOS:3 and 4 only.

Wherein the subsequent amplification of d) is carried out by means of methylation specific primers, as described above, said methylation specific primers comprise a sequence having a length of at least 9 nucleotides which hybridizes to a pretreated nucleic acid sequence according to one of SEQ ID NOS:5 to SEQ ID NO:20 and SEQ ID NOS:48 to SEQ ID NO:59 and sequences complementary thereto, wherein the base sequence of said oligomers comprises at least one CpG dinucleotide.

It is preferred that said set of MSP primer oligonucleotides includes at least two oligonucleotides whose sequences comprise a sequence having a length of at least 9 nucleotides which hybridizes to a pretreated nucleic acid sequence according to one or more of SEQ ID NOS:7-12 and 15-20.

In a further embodiment it is preferred that the said set MSP primer oligonucleotides includes at least two oligonucleotides whose sequences are each reverse complementary, identical, or hybridize under stringent or highly stringent conditions to an at least 9-base-pair long segment of the base sequences of each of SEQ ID NOS:7, 8, 15 & 16.

In a further preferred variant of said embodiment said set consists of at least MSP primer oligonucleotides includes at least two oligonucleotides whose sequences are each reverse complementary, identical, or hybridize under stringent or highly stringent conditions to an at least 9-base-pair long segment of the base sequences of each of SEQ ID NOS:7, 8, 15 and 16 and at least one blocker oligonucleotides whose sequences are each reverse complementary, identical, or hybridize under stringent or highly stringent conditions to an at least 9-base-pair long segment of the base sequences of each of SEQ ID NOS:9-12 and 17-20.

Step e) of the method, namely the detection of the specific amplificates indicative of the methylation status of one or more CpG positions according to SEQ ID NOS:1 to SEQ ID NO:4 and SEQ ID NOS:45 to SEQ ID NO:47 is carried out by means of real-time detection methods as described above.

In an alternative most preferred embodiment of the method the subsequent amplification of d) is carried out in the presence of blocking oligonucleotides, as described above. Said blocking oligonucleotides comprising a sequence having a length of at least 9 nucleotides which hybridizes to a pretreated nucleic acid sequence according to one of SEQ ID NOS: 5-20 and 48-59 and sequences complementary thereto, wherein the base sequence of said oligomers comprises at least one CpG, TpG or CpA dinucleotide.

It is preferred that said set of blocking oligonucleotides includes at least two oligonucleotides whose sequences comprise a sequence having a length of at least 9 nucleotides which hybridizes to a pretreated nucleic acid sequence according to one or more of SEQ ID NOS:7 to SEQ ID NO:12 and SEQ ID NOS:15 to SEQ ID NO: 20. In this embodiment of the invention it is particularly preferred that said set consists of at least one blocker oligonucleotides whose sequences are each reverse complementary, identical, or hybridize under stringent or highly stringent conditions to an at least 9-base-pair long segment of the base sequences of each of SEQ ID NOS:7-12 and 15-20.

In a further embodiment it is preferred that the said set consists of at least one blocker oligonucleotides whose sequences are each reverse complementary, identical, or hybridize under stringent or highly stringent conditions to an at least 9-base-pair long segment of the base sequences of each of SEQ ID NOS:7, 8, 15 and 16.

In a further preferred variant of said embodiment said set consists of at least one blocker oligonucleotides whose sequences are each reverse complementary, identical, or hybridize under stringent or highly stringent conditions to an at least 9-base-pair long segment of the base sequences of each of SEQ ID NOS:7, 8, 15 and 16 and at least one blocker oligonucleotides whose sequences are each reverse complementary, identical, or hybridize under stringent or highly stringent conditions to an at least 9-base-pair long segment of the base sequences of each of SEQ ID NOS:9-12 and 17-20.

Step e) of the method, namely the detection of the specific amplificates indicative of the methylation status of one or more CpG positions according to SEQ ID NOS:1 to SEQ ID NO:4 and SEQ ID NOS:45 to SEQ ID NO:47 is carried out by means of real-time detection methods as described above.

Additional embodiments of the invention provide a method for the analysis of the methylation status of genomic DNA according to the invention (SEQ ID NOS:1 to SEQ ID NO:4 and SEQ ID NOS:45 to SEQ ID NO:47, and complements thereof) without the need for pretreatment.

It is preferred that the methylation of one or more sequences selected from the group consisting SEQ ID NOS: 2, 3 and 4 are analysed. In this embodiment of the invention it is particularly preferred that the methylation of all of the sequences of the group consisting SEQ ID NOS: 2, 3 and 4 are analysed.

In the first step of such additional embodiments, the genomic DNA sample is isolated from tissue or cellular sources. Preferably, such sources include cell lines, histological slides, body fluids, stool or tissue embedded in paraffin. In the second step, the genomic DNA is extracted. This may be by any means standard in the art, including the use of commercially available kits. Briefly, wherein the DNA of interest is encapsulated in by a cellular membrane the biological sample must be disrupted and lysed by enzymatic, chemical or mechanical means. The DNA solution may then be cleared of proteins and other contaminants e.g. by digestion with proteinase K. The genomic DNA is then recovered from the solution. This may be carried out by means of a variety of methods including salting out, organic extraction or binding of the DNA to a solid phase support. The choice of method will be affected by several factors including time, expense and required quantity of DNA.

In a preferred embodiment, the DNA may be cleaved prior to the treatment, and this may be by any means standard in the state of the art, in particular with methylation-sensitive restriction endonucleases.

In the third step, the DNA is then digested with one or more methylation sensitive restriction enzymes. The digestion is carried out such that hydrolysis of the DNA at the restriction site is informative of the methylation status of a specific CpG dinucleotide.

In the fourth step, which is optional but a preferred embodiment, the restriction fragments are amplified. This is preferably carried out using a polymerase chain reaction, and said amplificates may carry suitable detectable labels as discussed above, namely fluorophore labels, radionuclides and mass labels.

In the fifth step the amplificates are detected. The detection may be by any means standard in the art, for example, but not limited to, gel electrophoresis analysis, hybridization analysis, incorporation of detectable tags within the PCR products, DNA array analysis, MALDI or ESI analysis.

In the final step the of the method the presence or absence of colon cell proliferative disorder is deduced based upon the methylation state of at least one CpG dinucleotide sequence of SEQ ID NOS:1 to SEQ ID NO:4 & SEQ ID NOS:45 to SEQ ID NO:47, or an average, or a value reflecting an average methylation state of a plurality of CpG dinucleotide sequences of SEQ ID NOS:1 to SEQ ID NO 4 and SEQ ID NOS:45 to SEQ ID NO:47.

In a further embodiment said deduction is based upon the methylation status of SEQ ID NO:2 only. In a further preferred embodiment said deduction is based upon the methylation status of SEQ ID 2 and one or more sequences chosen from, SEQ ID NOS:3 and 4.

Diagnostic Assays for Colon Cell Proliferative Disorders

The present invention enables diagnosis of events which are disadvantageous to patients or individuals in which important genetic and/or epigenetic parameters within one or more of SEQ ID NOS:1 to SEQ ID NO:4 and SEQ ID NOS: 45 to SEQ ID NO:47 may be used as markers. Said parameters obtained by means of the present invention may be compared to another set of genetic and/or epigenetic parameters, the differences serving as the basis for a diagnosis and/or prognosis of events which are disadvantageous to patients or individuals.

Specifically, the present invention provides for diagnostic cancer assays based on measurement of differential methylation of one or more CpG dinucleotide sequences of SEQ ID NOS:1 to SEQ ID NO:4 and SEQ ID NOS:45 to SEQ ID NO:47, or of subregions thereof that comprise such a CpG dinucleotide sequence. Typically, such assays involve obtaining a tissue sample from a test tissue, performing an assay to measure the methylation status of at least one of one or more CpG dinucleotide sequences of SEQ ID NOS:1 to SEQ ID NO:4 and SEQ ID NOS:45 to SEQ ID NO: 47 derived from the tissue sample, relative to a control sample, or a known standard and making a diagnosis or prognosis based thereon.

In particular preferred embodiments, inventive oligomers are used to assess the CpG dinucleotide methylation status, such as those based on SEQ ID NOS:1 to SEQ ID NOS:20 and 45 to 59, or arrays thereof, as well as in kits based thereon and useful for the diagnosis and/or prognosis of colon cell proliferative disorders.

Kits

Moreover, an additional aspect of the present invention is a kit comprising, for example: a bisulfite-containing reagent; a set of primer oligonucleotides containing at least two oligonucleotides whose sequences in each case correspond, are complementary, or hybridize under stringent or highly stringent conditions to a 16-base long segment of the sequences SEQ ID NOS:1 to SEQ ID NO:20 & SEQ ID NOS:45 to SEQ ID NO:59; oligonucleotides and/or PNA-oligomers; as well as instructions for carrying out and evaluating the described method.

More preferred is a kit comprising the oligonucleotides whose sequences in each case correspond, are complementary, or hybridize under stringent or highly stringent conditions to a 16-base long segment of the sequences SEQ ID NOS: 5-20.

Also preferred is a kit comprising the oligonucleotides whose sequences in each case correspond, are complementary, or hybridize under stringent or highly stringent conditions to a 16-base long segment of the sequences SEQ ID NOS: 7, 8, 15 & 16.

Further preferred is a kit comprising the oligonucleotides whose sequences in each case correspond, are complementary, or hybridize under stringent or highly stringent conditions to a 16-base long segment of the sequences SEQ ID NOS:7, 8, 15 and 16 and at least one of SEQ ID NOS:9-12 and 17-20.

In a further preferred embodiment, said kit may further comprise standard reagents for performing a CpG position-specific methylation analysis, wherein said analysis comprises one or more of the following techniques: MS-SNuPE™, MSP, MethyLight®, HeavyMethyl™, COBRA™, and nucleic acid sequencing. However, a kit along the lines of the present invention can also contain only part of the aforementioned components.

Typical reagents (e.g., as might be found in a typical COBRA™-based kit) for COBRA™ analysis may include, but are not limited to: PCR primers for specific gene (or methylation-altered DNA sequence or CpG island); restriction enzyme and appropriate buffer; gene-hybridization oligo; control hybridization oligo; kinase labeling kit f or oligo probe; and radioactive nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

Typical reagents (e.g., as might be found in a typical MethyLight®-based kit) for MethyLight® analysis may include, but are not limited to: PCR primers for specific gene (or methylation-altered DNA sequence or CpG island); TaqMan® probes; optimized PCR buffers and deoxynucleotides; and Taq polymerase.

Typical reagents (e.g., as might be found in a typical Ms-SNuPE™-based kit) for Ms-SNuPE analysis may include, but are not limited to: PCR primers for specific gene (or methylation-altered DNA sequence or CpG island); optimized PCR buffers and deoxynucleotides; gel extraction kit; positive control primers; Ms-SNuPE™ primers for specific gene; reaction buffer (for the Ms-SNuPE™ reaction); and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

Typical reagents (e.g., as might be found in a typical MSP-based kit) for MSP analysis may include, but are not limited to: methylated and unmethylated PCR primers for specific gene (or methylation-altered DNA sequence or CpG island), optimized PCR buffers and deoxynucleotides, and specific probes.

While the present invention has been described with specificity in accordance with certain of its preferred embodiments, the following example serves only to illustrate the invention and is not intended to limit the invention within the principles and scope of the broadest interpretations and equivalent configurations thereof.

EXAMPLES

Material and Methods

Subjects for MethyLight Analysis

Colon tissues were obtained by surgical resection from 47 patients (29 male, 18 female) with colon cancer, with a median age of 66 years (range 31-93 years), from the tumor and a tumor-free location which was at least 2 cm distant from the tumor and which was confirmed to be without any tumor cell infiltration by histological assessment. In all 47 patients tissue samples from the colon cancer were obtained for molecular analysis, in 21 of these cases a matched non-cancer colon sample was also obtained for molecular analysis after tumor cell infiltration was ruled out by histological assessment. The metastatic lesions were obtained from 24 patients (13 male, 11 female, median age 64.5 yrs, range 41-79) with colorectal cancer that developed liver metastasis after prior successful colon cancer resection. In one case the primary colon cancer and a single liver metastasis were resected at the same time in a 74 year old female patient. Immediately after surgery, tissue samples were put in liquid nitrogen and stored at −80° C. until use. Formalin fixed tissues were processed as previously described and sections were stained with hematoxylin and eosin for histological evaluation. Tumor stages were assessed using the TNM-system.

DNA Extraction

Genomic DNA was extracted from the tissues using the proteinase K digestion method.

Genome-Wide Methylation Screening Assay

Differentially methylated genomic sequences were identified using Methylation-specific arbitrarily primed PCR analysis (MS AP-PCR) by comparison of different levels of disease to age-matched normal tissue for several different age groups (see for example Young J, Biden K G, Sinuns L A, Huggard P, Karamatic R, Eyre H J, Sutherland G R, Herath N, Barker M, Anderson G J, Fitzpatrick D R, Ramm G A, Jass J R, Leggett B A. HPP1: a transmembrane protein-encoding gene commonly methylated in colorectal polyps and cancers. Proc Natl Acad Sci USA 2001; 98:265-270.) DNA from colon adenomas, CRC samples from patients with no lymph node involvement or metastasis and CRC samples from patient with lymph node involvement and/or metastasis was compared in MS AP-PCR experiments to age-matched normal colon tissue and to age-matched normal peripheral blood lymphocytes.

Five samples for each tissue type were collected for each of three age groups; over 65 years, 50 to 65 years and under 50 years. Genomic DNA was extracted from the tissue samples using Qiagen Genomic-Tip 500/G columns. The five DNA samples from each tissue type and each age group were pooled and experiments were performed as follows. DNA was digested with RsaI to generate smaller DNA fragments before digestion with MspI and HpaII, two restriction enzymes with different sensitivities to cytosine methylation. Then MS AP-PCR was performed as previously described by Liang et al. The digested DNA was amplified using these sets of primers: G1, 5'-GCGCCGACGT-3';(SEQ ID NO:42); G5,5'-TGCGACGCCG-3'; (SEQ ID NO:43); APBS5,5'-CTCCCACGCG-3' (SEQ ID NO:44). After amplification fragments were separated on polyacrylamide gels and those exhibiting a pattern of differential methylation were eluted from the gel, cloned into vectors and sequenced as outlined above. Identification of sequences was performed by BLAST searches in Genbank.

MethyLight™ Analysis

Genomic DNA was analyzed by the MethyLight technique after bisulfite conversion as previously reported by Eads et al. (Epigenetic patterns in the progression of esophageal adenocarcinoma. Cancer Res 2001; 61:3410-3418. and Fields of aberrant CpG island hypermethylation in Barrett's esophagus and associated adenocarcinoma. Cancer Res 2000; 60:5021-5026). In this analysis three oligos are used in every reaction. Two locus-specific PCR primers flank an oligonucleotide probe with a 5' fluorescent reporter dye (6FAM) and a 3' quencher dye (BHQ-1). For this analysis primers and probes are specifically designed to bind to bisulfite-converted DNA, which generally span 7 to 10 CpG dinucleotides. The gene of interest is then amplified and normalized to a reference set (β-actin (ACTB)) to normalize for input DNA. The specificity of the reactions for methylated DNA is confirmed using human sperm DNA (unmethylated) and CpGenome Universal Methylated DNA (Chemicon (subsidiary of Serologicals) catalog #S7821) (methylated). For standardization the primers and the probe for analysis of the ACTB gene lack CpG dinucleotides so that amplification is possible regardless of methylation levels. TaqMan PCR reactions were performed in parallel with primers specific for the bisulfite-converted methylated sequence for a particular locus and with the ACTB reference primers. The ratio between the values was calculated in these two TaqMan analyses, using this approach the degree of methylation at that locus was determined. The extent of methylation at a specific locus was determined by the following formula:

$$[(\text{gene/actb})^{sample}:(\text{gene/actb})^{SssI\text{-}treated\ genomic\ DNA}]\times 100.$$

A cut off value of 4% gave the best discrimination between normal and cancerous samples, as previously reported. Therefore, samples with ≧4% fully methylated molecules were termed methylated, where as samples with <4% were considered unmethylated. The primer and probe sequences are listed in Table 1 and were used as previously reported by Eads et al.

Bisulfite Sequencing

Bisulfite genomic sequencing was performed for the ALX4 gene in order to confirm the results obtained by MethyLight™ analysis. Briefly, bisulfite treated genomic DNA from 4 colon cancers and matched normal colon mucosa was amplified with primers specific for a fragment of the ALX4 gene containing 39 CpG sites and spanning the region that was analysed with the Methylight™ assay: ALX4_bis1, 5'-TGAATAGGGTGATATTTTAGTTAGG-3' (SEQ ID NO:76); ALX4_bis2,5'-ATAAATCATCCCAAAAC-CTCTA-3' (SEQ ID NO: 60). PCR was carried out in a reaction mixture (25 μl) containing 7 μl of DNA, 0.2 mM dNTPs, 1 μM primers, and 0.25 units of DyNAzyme EXT DNA Polymerase (Finnzyines). Amplification was performed using the following condition: 94° C. for 2 min, followed by 36 cycles (94° C. for 1 min, 72° C. for 2 min) and then 72° C. for 10 minutes. PCR products were separated on 1% agarose gel, stained with ethidium bromide and visualized with an UV transilluminator. DNA fragments of interest were cloned into a plasmid vector with the TOPO TA cloning kit (Invitrogen, Carlsbad, Calif.) according to manufacturer's recommendations and sequence was confirmed by automated sequencing.

Statistical Analysis

The PMR values of the Methylight assays were dichotomized for statistical purposes as previously reported by Eads et al. PMR values above 4% were considered as methylation positive and classified as '1', where as PMR levels below 4% were classified as '0' (no methylation). This dichotomization should level off the quantitative impact of different levels of hypermethylation per gene, and allow the cross-gene comparison of methylation per gene in colon cancer and metastasis. The different clinicopathological features, such as location of primary tumor, grade of differentiation or stage of cancer were used as nominal variables in the Fisher's exact test or Chi square test. Otherwise student's t-test was used to determine statistical difference. All tests were two-sided, and a p-value of <0.05 was considered statistically significant.

Results

Differential methylation of a fragment of approximately 242 bp with genomic sequence matching a portion of the first intron of ALX4 was confirmed in seven different MS AP-PCR experiments comparing colon cancer and adenoma DNA to normal DNA obtained from the same individuals. In experiments performed on samples from patients over 65 years old, bands corresponding to a methylated fragment of ALX4 were found in DNA from a denomas, non-metastatic adenocarcinoma and metastatic adenocarcinoma samples when compared to normal age-matched colon tissue. The band was also identified in a mixture of pre-cancerous and adenocarcinoma samples compared to age-matched PBL DNA. An identical band was found in adenoma sample DNA from patients 50-65 years old when compared to normal age-matched colon tissue and a mixture of pre-cancerous and adenocarcinoma DNA from patients 50-65 years compared to age-matched PBL DNA. Lastly the fragment was found in a comparison of adenomas from patients less than 50 years compared to age-matched normal tissue (data not shown).

Figure 2:
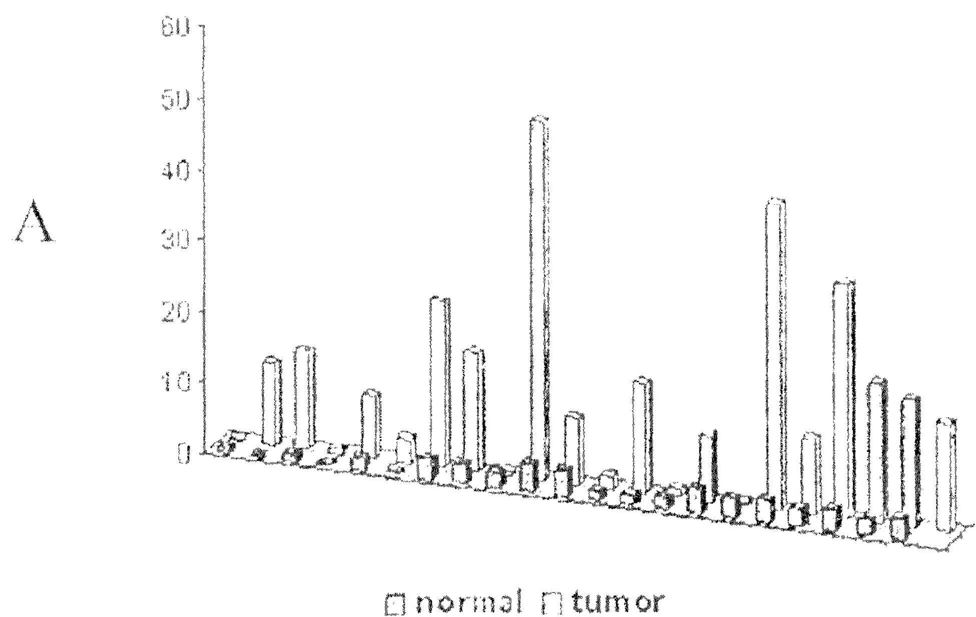
FIGS. 2A and 2B show the degree of methylation of the ALX4 gene as assessed by MethyLight™ assay as outlined in examples. The X-axis shows the percentage methylated reference (PMR). Figure A shows ALX4 gene methylation in normal colon mucosa and matched colon cancer; Figure B shows ALX4 gene methylation in primary colorectal cancers and metastasis.

Confirmation of ALX4 Gene Methylation in Primary and Metastatic Colorectal Cancer The methylation of the ALX4 gene was assessed in 47 colon cancers and compared to 21 cases of normal colon mucosa which were obtained from a subset of these cancer patients. Using the Methylight assay a high degree of methylation was found in the cancerous colon as compared to the matched normal colon mucosa (FIG. 2A). Thirty cancers exhibited a PMR >4% (30/47) where as in none of the 21 normal colon samples ALX4 gene methylation was observed (p<0.0001). We then assessed the degree of ALX4 methylation in our series of metastatic samples and compared them to the primary colon cancers. In this series, apart from one patient, the tissues were, however, not matched and thus from different patients. Nonetheless, our analysis showed that a high degree of methylation can be found in both primary (30/47) and metastatic colon cancer (16/24), which did not differ by statistical analysis (FIG. 2B). Interestingly, primary colon cancer and metastatic tissues from the one female patient from which both tissues were obtained, exhibited a low degree of methylation in the primary cancer and a high degree of methylation in the metastatic lesion (FIG. 2B).

Figure 3:
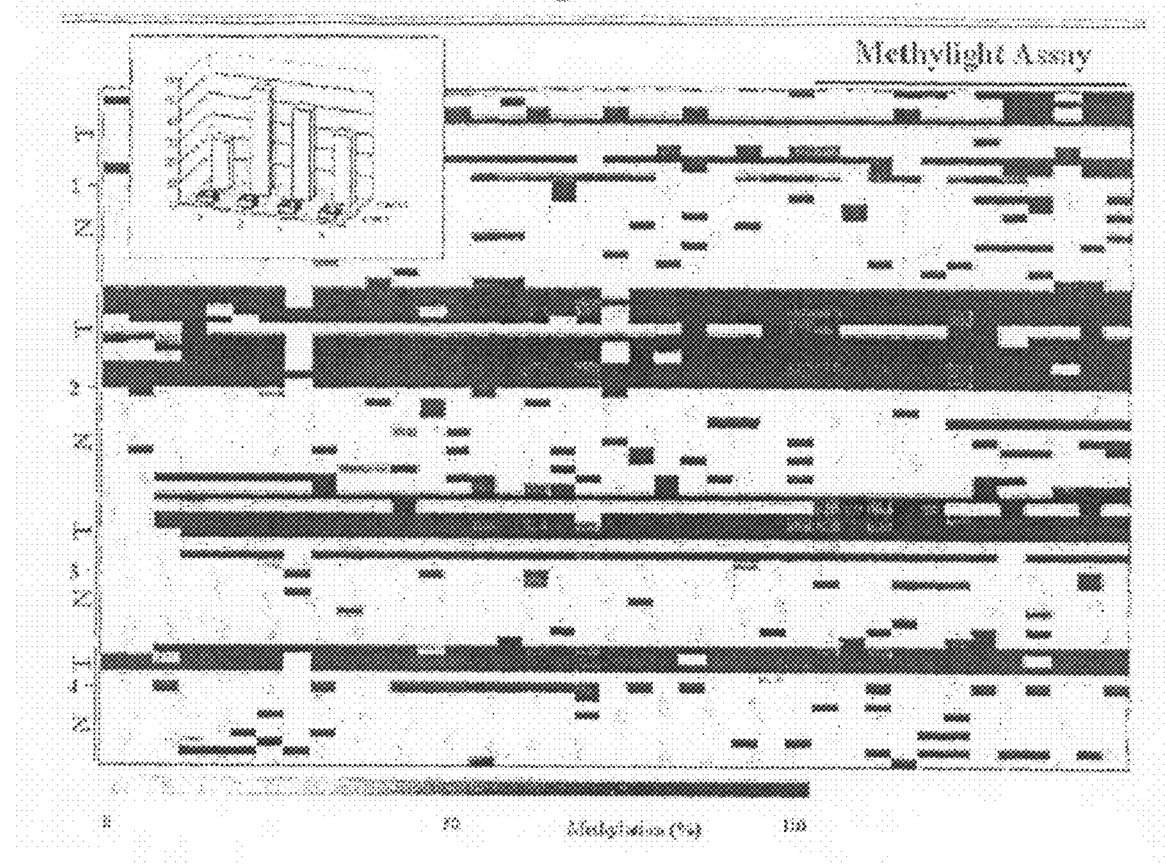
FIG. 3 shows bisulfite sequencing. Four cases of cancers with a high degree of methylation and their matched normal non-malignant colon mucosa tissues were selected (inset). ALX4 gene methylation was confirmed by sequencing of bisulfite treated genomic DNA of samples 1-4. N, normal mucosa; T, tumor, numbers 1-4 correspond to cases 1-4 in the Methylight assay (inset); Methylight assay, indicates the CpG sites that were covered by both the Methylight assay and sequencing of the respective DNA fragments.

In order to confirm the results of ALX4 gene methylation obtained by Methylight assay we also performed bisulfite sequencing on 4 matched normal and colon cancer samples. These 4 patients were selected because there was a dramatic difference in the levels of methylation of the ALX4 gene in the cancer versus the matched normal colon sample (FIG. 3). The region of the ALX4 gene that was analysed by bisulfite sequencing spanned 39 CpG sites, including the 12 CpG sites that were analysed with the Methylight assay. The DNA fragments encoding ALX4 were amplified by PCR using bisulfite treated DNA and 3-11 clones per sample were sequenced. Similar to the results obtained with the Methylight assay we found that the majority of CpG sites were methylated in the cancer samples, where as in the normal colon mucosa the CpG sites were widely unmethylated (FIG. 3). The varying degrees of methylation that were observed, however, in the cancer samples reflect the degree of contaminating non-malignant cells that were present in the DNA preparation from the cancer tissues used for methylation analysis. Overall, the results obtained by bisulfite sequencing confirmed the results of the PCR based assay, indicating that the Methylight assay correctly assesses the methylation of the ALX4 gene in colorectal cancer.

Analysis of Gene Methylation in Primary and Metastatic Colorectal Cancer

Figure 4:
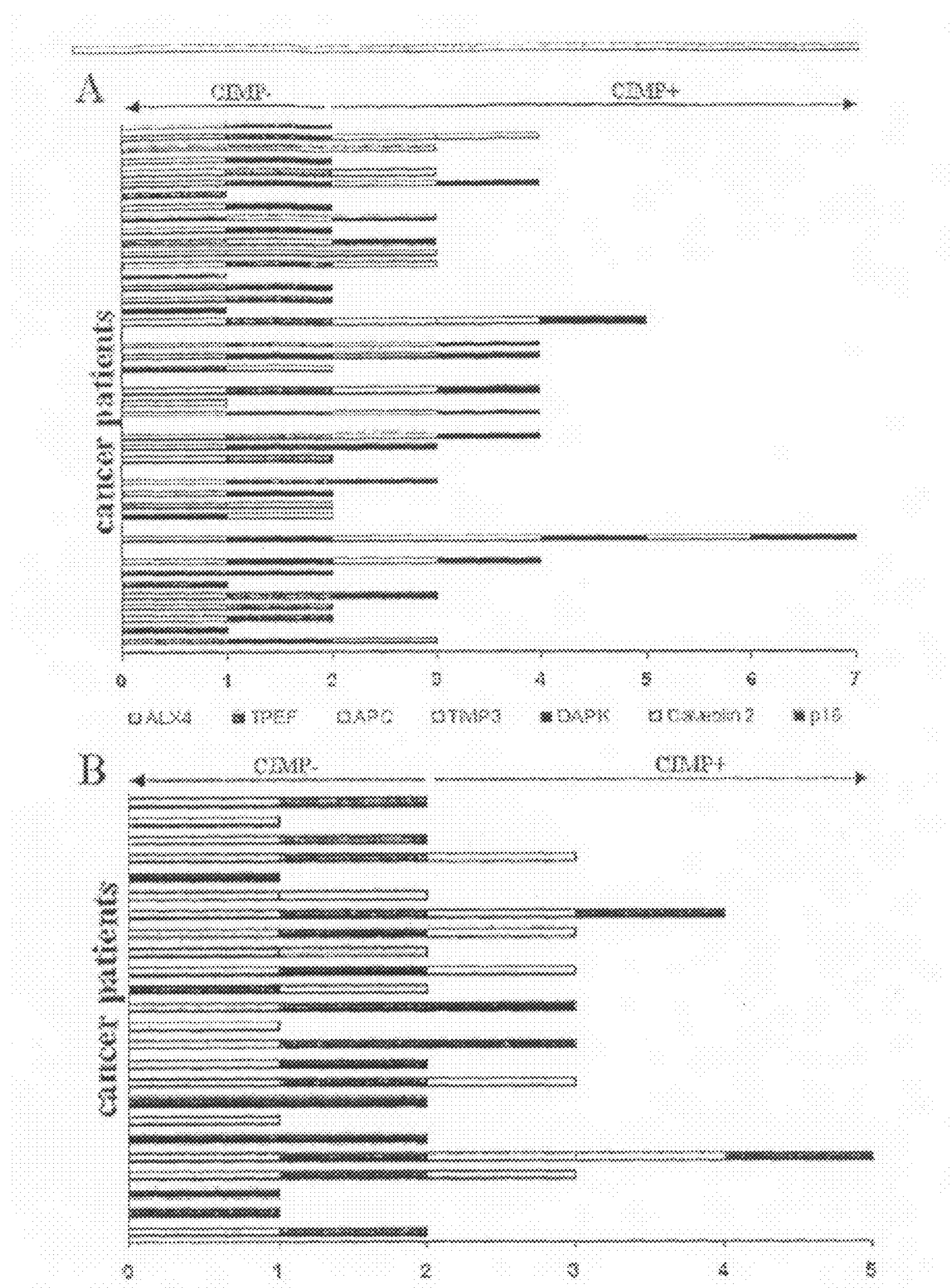
FIGS. 4A and 4B show the number of methylated genes per primary colorectal cancer (A) and metastasis (B). CIMP+ status was defined as 2 or more methylated genes per patient.

Next we analysed our tissues for gene methylation using a set of genes that had been previously be reported by other groups to be associated with either colon cancer pathogenesis or the development of cancer metastasis: TPEF, p16/INK4A, APC, caveolin-2, DAPK, TIMP3. Using Methylight assays we assessed the methylation status of ALX4 and the other 6 genes in our series of primary and metastatic colon cancers. The cut-off of methylation was chosen to be a PMR (percentage of methylated reference) of >4% (as previously reported by Eads et al.,) and all samples with a PMR >4% were classified as methylation positive ('1'), where as samples with a PMR below 4% were considered methylation negative ('0'). The results of the methylation analysis of each gene in primary and colon cancer is given in table 3. In addition, the numbers were added giving the total numbers of methylated genes per sample. Using this approach we observed at least one methylated gene in 40 of 47 primary cancers, this would indicate a sensitivity of 85.1% for the detection of cancer (FIG. 4A). In contrast, only one of 21 normal colon mucosa samples exhibited TPEF gene methylation, indicating that the specificity of this marker set would be 95.2%. Thus, the analysis of only three genes, i.e. ALX4, TPEF and p16, allowed the identification of these 40 cancers, where as the other genes did not further contribute to the detection of colon cancer. In the metastatic lesions all 24 cases exhibited at least one of these methylated gene: ALX4, TPEF or APC, accounting for a detection rate of 100% (FIG. 4B).

ALX4 contributes to the identification of CIMP in Primary and Metastatic Colon Cancer A condition termed CpG island methylator phenotype (CIMP) which is associated with microsatellite instability related to hMLH1 methylation, a proximal location in the colon and a family history of colon cancers was recently identified by Toyota et al. (CpG island methylator phenotype in colorectal cancer. Proc Natl Acad Sci USA 1999; 96:8681-8686). In our series CIMP+ cancers were observed in 20 of 47 cases (FIG. 4A). These cancers exhibited at least 3 methylated genes, which included ALX4, TPEF, APC, Caveolin-2, TIMP3 and p16. In the metastatic lesions we observed CIMP+cancers in 9 of 24 cancers. The genes found to be methylated in CIMP+metastatic lesions included ALX4, TPEF, TIMP3 and APC (FIG. 4B). Colon cancers located in either the cecum, ascending colon, colon transversum or descending colon exhibited a CIMP+ status in 14 of 24 cases, where as cancers of the sigma and/or rectum were CIMP+ in 6 of 22 cases, a difference that was also statistically significant (p=0.026). However, CTMP+ tumors were not associated with either early or advanced stages in our series, and showed no association with the degree of differentiation.

Figure 5:
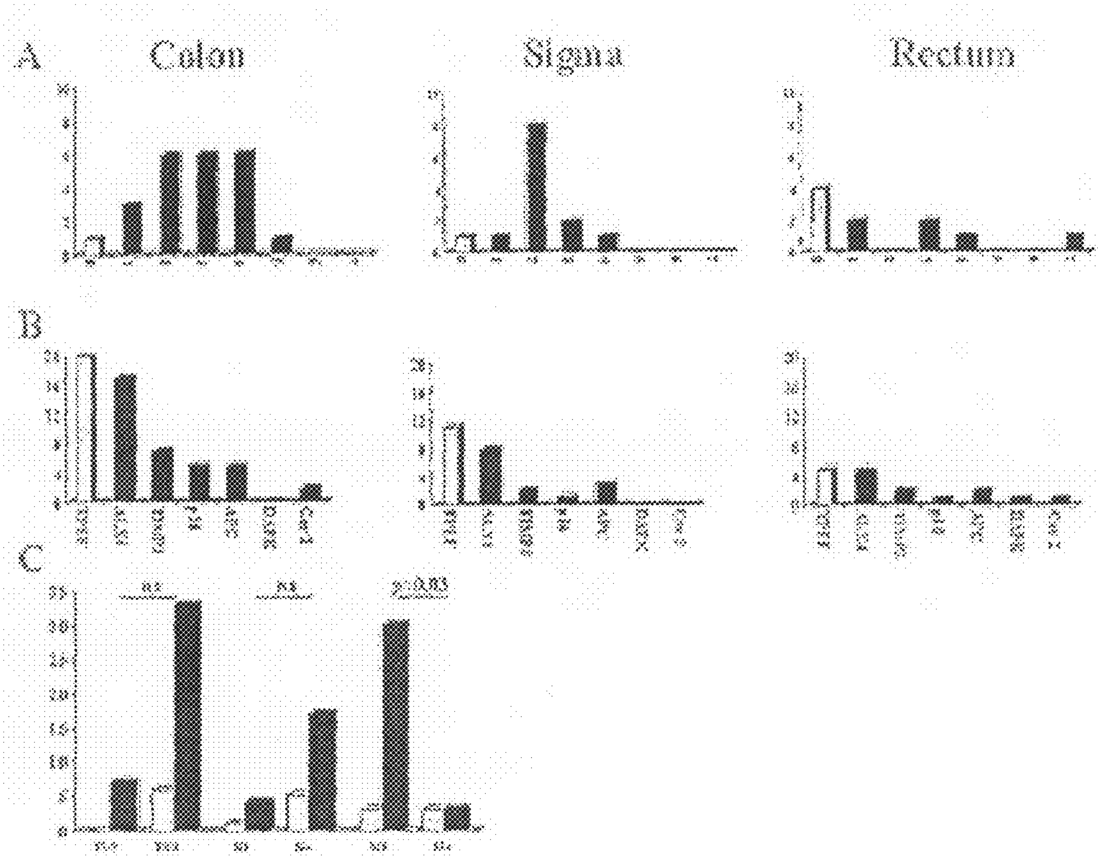
FIGS. 5A, 5B and 5C show an analysis of methylation with regard to clinicopathological features of colorectal cancers. A. In cancers of the colon and the sigma methylation was significantly more frequent than in cancers of the rectum only. y axis: number of patients; x axis: number of methylated genes B. TPEF methylation was significantly more frequent in cancers of the colon and sigma. Number of patients analysed: colon cancer: n=23, sigma cancer: n=13, rectal cancer: n=10. One patient with recurrent cancer was not included in this analysis. y axis: number of patients; x axis: number of methylated genes. C. Cancers without distant metastasis were frequently methylated, grey box: no methylation; black box: methylation of 1 to 7 genes.

Association of Gene Methylation in Colon Cancer with Clinicopathological Features of Colon Cancer In order to assess a potential association of the presence of methylation with the location of the primary tumor we classified our colorectal cancers into two groups: rectal cancers (n=10), and non-rectal cancers (n=36). Using Fisher's exact test, we found that there was a statistical significant difference in the presence of methylation with regard to the location of the primary tumor. While rectal cancers exhibited no methylation in 4 of the cases, where as methylation of 1 to 7 genes was found in 6 cases, the vast majority of colon cancers (34/36) exhibited methylation in at least one gene (p=0.014). Thus, from this analysis we can assume that methylation is significantly more frequent in proximal, i.e. non-rectal cancers of the large intestine (FIG. 5A).

We analysed not only the association between the location of the primary and the overall presence of gene methylation per patient, but also analysed each single gene with regard to this association of location and gene methylation. However, apart from TPEF, none of the other genes—including ALX4—were linked to a certain location of the primary tumor, probably because of the low number of methylated genes observed in our study. However, TPEF was more frequently methylated in colon cancers (31/36) compared to rectal cancers (5/10) (p=0.023) (FIG. 5B). The total number of methylated genes in rectal cancers (19/70) was also compared to the total number of methylated genes in colon cancer (89/252), however, this difference did not reach statistical significance (p=0.0513).

While methylation is considered an early step in the process of colorectal cancer pathogenesis, we assessed the presence of methylation in the cancers with regard to the stage of the cancers. While none of our patients was in the UICC stage I, 20 patients presented with UICC stage II cancer, 13 with stage III and 13 with stage IV colorectal cancer. Interestingly, the number of patients without gene methylation increased with the UICC stage, in that patients with UICC stage II had at least 1 methylated gene compared to the more advanced stages, however this observation was not statistically significant. However, while we found no association between the T stage and the presence of methylation, the presence of distant metastasis (M+ stage) was associated with significantly less methylated cancers compared to tumors without distant metastasis. Thus, while 3 of 6 cancers with distant metastasis did not show any gene methylation, cancers without distant metastasis (M0) presented with at least one methylated gene in 30 of 33 cases (p=0.033) (FIG. 5C). Again, the detailed analysis of every single gene with regard to the association with distant metastasis did not identify a single gene that was associated with the presence of distant metastasis, again maybe due to the limited number of cases analysed.

Discussion

ALX4 gene methylation was identified by MS AP-PCR in our study and we confirmed the presence of ALX4 methylation in a larger series of primary and metastatic colon cancers using the Methylight assay and bisulfite sequencing. ALX4 gene methylation was observed in 30 of 47 primary cancers and in none of the normal colon mucosa tissue samples. Furthermore, ALX4 was frequently methylated in the liver metastasis of a second set of patients with colorectal cancers. In the one female patient in which primary colon cancer and liver metastasis were resected at the same time we found a high degree of ALX4 gene methylation in the liver metastasis as opposed to the primary cancer, indicating that methylation of ALX4 may occur 'de novo' in the metastatic cancer cells even in the absence of methylation in the primary cancer cells.

In order to further assess the role of ALX4 gene methylation in primary and metastatic colon cancer, we analysed the presence of methylation of 6 other genes that have previously been linked either to colon cancer pathogenesis or metastatic development in our series of colon cancer and metastatic cancer tissues: TPEF/HPP1, p16/INK4A, APC, caveolin-2, DAPK and TIMP3. While TPEF and ALX4 exhibited a similar high frequency of methylation in primary colon cancer, p16 and APC were less frequently methylated. Of the 47 analysed primary colon cancers 40 exhibited at least one of the three methylated genes ALX4, TPEF or p16, indicating that a methylation based diagnostic test including these three genes may achieve a detection rate of 85.1%; since only one normal case exhibited a significant degree of methylation of the TPEF gene specificity would be 95.2%.

The cancers were then grouped according to the location of the primary cancer into rectal and non-rectal cancers. Overall gene methylation was more frequently present in non-rectal cancers compared to cancers of the rectum, an observation that has been reported by other groups as well. However, ALX4 gene methylation alone—in contrast to TPEF—was not associated with either location of the primary tumor, most probably due to the limited number of cases analysed in our study. Furthermore, since gene methylation has been considered to be an early event in the pathogenesis of this and other cancers, we assessed the frequency of methylation in each UICC stage and in cancers grouped according to the size of the primary tumor (T), presence of lymph nodes (N) or distant metastasis (M). However, colorectal cancers without distant metastasis frequently exhibited gene methylation, which contrasts with previous reports that gene hypermethylation may be associated with a poor prognosis in this and other cancers.

Recently Toyota et al. (CpG island methylator phenotype in colorectal cancer. Proc Natl Acad Sci USA 1999; 96:8681-8686.) reported the presence of multiple methylated genes in colon cancer, a condition they termed CpG island methylator phenotype (CIMP). In their analysis two types of methylation were identified: Type A methylation referred to the age-related methylation of CpG islands in tumors and the normal colon mucosa. In contrast, some genes exhibited methylation only in colon cancers which was classified as type C methylation. Interestingly, most CIMP+ cancers were associated with microsatellite instability related to hMLH1 methylation, a proximal location and a family history of colon cancers. In our series CIMP+ cancers were observed in 20 of 47 cases and were located primarily in the proximal colon cancer, an association which has already been reported by Toyota et al. and Rijnsoever et al. (CpG island methylator phenotype in colorectal cancer. Proc Natl Acad Sci USA 1999; 96:8681-8686. and Characterisation of colorectal cancers showing hypermethylation at multiple CpG islands. Gut 2002; 51:797-802). However, our CIMP+ tumors were not associated with either early or advanced stages in our series, which is similar to the findings reported by Toyota et al. In contrast to our study, Rijnsoever et al. reported that in their analysis CIMP+ colon cancers were poorly differentiated, a finding that was not observed in our and other studies and may be due to the larger patient group that was analysed in their study.

To our knowledge our study is the first to also address the role of gene methylation in metastatic colorectal cancers using a panel of 7 genes—including ALX4—that were analysed by the highly sensitive Methylight™ assay. Using this assay we found several genes to be methylated in both metastatic lesions and primary cancers, as well as genes that were neither methylated in metastasis nor in primary colorectal cancers. Apart from this observation, APC gene methylation increased in metastatic lesions compared to primary cancers. Based on these findings, we can classify the patterns of methylation in liver metastasis in three groups: class I genes: high degree of methylation in primary tumor and liver metastasis (ALX4, TPEF, p16), class II genes: higher degree of methylation in metastasis compared to primary tumor (APC) and class genes III: no methylation in either primary tumor or metastasis (caveolin-2, DAPK, TIMP3). Interestingly, all 24 metastases exhibited at least one methylated gene of the class I genes, indicating that this set of genes may be valuable for the methylation specific detection of liver metastasis in colon cancer. Interestingly, the two genes that exhibited a very high degree of methylation in the primary colon cancers, are also frequently methylated in the liver metastasis of colon cancer (ALX4, TPEF). From our analysis we assume that methylation of these genes occurs early in these cancers and that they remain methylated in the progression of the disease. However, the high frequency of methylation detected in the primary cancers and metastatic lesions makes them ideal candidates for a methylation-based diagnostic tool for localized and metastatic colorectal cancer.

In summary, using MS AP-PCR we identified the methylation of ALX4 in colorectal cancers and further analysis revealed that ALX4 gene methylation is a frequent event in colorectal cancer pathogenesis. Together with a further set of genes, ALX4 allows the identification of primary and metastatic colorectal cancers indicating that methylation based diagnostic tests may be helpful in the identification of this and other malignancies and, thus, may improve the detection and overall prognosis of patients with these cancers.

TABLE 1

List of primers and probes used for Methylight analysis

| Gene | forward primer (5'-3') | reverse primer (5'-3') | probe sequence (5'-3') |
|---|---|---|---|
| ALX4 | CGCGGTTTCGATTTTAATGC (SEQ ID NO: 21) | ACTCCGACTTAACCCGACGAT (SEQ ID NO: 22) | 6FAM-CGACGAAATTCCTAACGCAACCGCTTAA-BHQ1 (SEQ ID NO: 23) |
| Caveolin 2 | TTTCGGATGGGAACGGTGTA (SEQ ID NO: 24) | CTCCCACCGCCGTTACC (SEQ ID NO: 25) | 6FAM-CCCGTCCTAACCGTCCGCCCT-BHQ1 (SEQ ID NO: 26) |
| DAPK | TCGTCGTCGTTTCGGTTAGTT (SEQ ID NO: 27) | CCCTCCGAAACGCTATCGA (SEQ ID NO: 28) | 6FAM-CGACCATAAACGCCAACGCCG-BHQ1 (SEQ ID NO: 29) |
| TPEF | TTTTTTTTTCGGACGTCGTTG (SEQ ID NO: 30) | CCTCTACATACGCCGCGAAT (SEQ ID NO: 31) | 6FAM-AATTACCGAAAACATCGACCGA-BHQ1 (SEQ ID NO: 32) |
| p16/INK4A | TGGAATTTTCGGTTGATTGGTT (SEQ ID NO: 33) | AACAACGTCCGCACCTCCT (SEQ ID NO: 34) | 6FAM-ACCCGACCCCGAACCGCG-BHQ1 (SEQ ID NO: 35) |
| APC | GAACCAAAACGCTCCCCAT (SEQ ID NO: 36) | TTATATGTCGGTTACGTGCGTTTATAT (SEQ ID NO: 37) | 6FAM-CCCGTCGAAAACCCGCCGATTA-BHQ1 (SEQ ID NO: 38) |
| TIMP3 | GCGTCGGAGGTTAAGGTTGTT (SEQ ID NO: 39) | CTCTCCAAAATTACCGTACGCG (SEQ ID NO: 40) | 6FAM-AACTCGCTCGCCCGCCGAA-BHQ1 (SEQ ID NO: 41) |
| Caveolin | TTTCGGATGGGAACGGTGTA (SEQ ID NO: 24) | CTCCCACCGCCGTTACC (SEQ ID NO: 25) | 6FAM-CCCGTCCTAACCGTCCGCCCT-BHQ1 (SEQ ID NO: 26) |

TABLE 2

Genes and sequences according to the invention.

| Gene name | Genomic SEQ ID NO | Methylated treated SEQ ID NOs: | Unmethylated treated SEQ ID NOs: |
|---|---|---|---|
| APC | 1 | 5 & 6 | 13 & 14 |
| ALX4 | 2 | 7 & 8 | 15 & 16 |
| TPEF | 3 | 9 & 10 | 17 & 18 |
| p16 | 4 | 11 & 12 | 19 & 20 |
| DAPK | 45 | 48 & 49 | 54 & 55 |
| TIMP3 | 46 | 50 & 51 | 56 & 57 |
| Caveolin 2 | 47 | 52 & 53 | 58 & 59 |

TABLE 3

Summary of results from analysis of gene methylation in primary cancer and metastasis.

| Gene | Normal (n = 21) | Tumor (n = 47) | Metastasis (n = 24) | Class |
|---|---|---|---|---|
| ALX4 | 0/21 | 30/47* | 16/24 | I |
| TPEF | 1/21 | 36/47* | 19/24 | I |
| p16 | 0/21 | 15/47# | 6/24 | I |
| APC | 0/21 | 10/47# | 10/24$ | II |
| TIMP3 | 1/21 | 11/47 | 2/24 | III |
| DAPK | 0/21 | 1/47 | 0/24 | III |
| Caveolin 2 | 0/21 | 5/47 | 1/24 | III |

The invention claimed is:

1. A method for identifying increased likelihood of colorectal cancer in a human subject comprising:

obtaining a biological sample comprising colorectal cells from the subject;

determining methylation levels of ALX4 and TPEF in the sample;

comparing the methylation level of ALX4 and TPEF in the sample with the methylation level in normal colorectal cells; and identifying the subject as having increased likelihood of colorectal cancer based on a higher degree of methylation in the sample compared to the normal colorectal cells.

2. The method of claim 1, comprising:

contacting genomic DNA or a fragment thereof, obtained from the sample, with one reagent or a plurality of reagents for distinguishing between methylated and non methylated CpG dinucleotide sequences within at least one target sequences of the genomic DNA or fragment thereof, wherein the target sequence comprises, or hybridizes under stringent conditions to, at least 16 contiguous nucleotides of a sequence selected from the group consisting of SEQ ID NOS: 7, 8, 9, 10, 15, 16, 17 and 18, said the contiguous nucleotides comprising at least one CpG dinucleotide sequence; and determining, based at least in part on the distinguishing, the methylation state of at least one target CpG dinucleotide sequence, or an average, or a value reflecting an average methylation state of a plurality of target CpG dinucleotide sequences, thereby identifying increased likihood of colorectal cancer.

3. The method of claim 2, wherein distinguishing between methylated and non methylated CpG dinucleotide sequences within the target sequence comprises converting unmethylated cytosine bases within the target sequence to uracil or to another base that is detectably dissimilar to cytosine in terms of hybridization properties.

4. The method of claim 1, wherein the biological sample is selected from the group consisting of cell lines, histological slides, biopsies, paraffin-embedded tissue, bodily fluids, stool, blood, and combinations thereof.

5. The method of claim 2, wherein distinguishing between methylated and non methylated CpG dinucleotide sequences within the at least one target sequence comprises use of at least one nucleic acid molecule or peptide nucleic acid (PNA) molecule comprising, in each case a contiguous sequence at least 9 nucleotides in length that is complementary to, or hybridizes under moderately stringent or stringent conditions to a sequence selected from the group consisting of SEQ ID NOS:7, 8, 9, 10, 15, 16, 17 and 18, and complements thereof.

6. The method of claim 1, comprising:

extracting or otherwise isolating genomic DNA from the sample;

treating the isolated genomic DNA, or a fragment thereof, with one or more reagents to convert cytosine bases that are unmethylated in the 5-position thereof to uracil or to another base that is detectably dissimilar to cytosine in terms of hybridization properties;

contacting the treated genomic DNA, or the treated fragment thereof, with an amplification enzyme and at least two primers comprising, in each case a contiguous sequence of at least 9 nucleotides that is complementary to, or hybridizes under stringent conditions to a sequence selected from the group consisting of SEQ ID NOS: 7, 8, 9, 10, 15, 16, 17 and 18, and complements thereof, wherein the treated genomic DNA or the fragment thereof is either amplified to produce at least one amplificate, or is not amplified; and determining, based on a presence or absence of, or on a property of said the amplificate, the methylation state of at least one CpG dinucleotide of SEQ ID NOS: 2 and 3, or an average, or a value reflecting an average methylation state of a plurality of CpG dinucleotides of SEQ ID NOS: 2 and 3, wherein identification of increased likihood of colorectal cancer is afforded.

7. The method of claim 6, wherein treating the genomic DNA, or the fragment thereof, comprises use of a reagent selected from the group consisting of bisulfite, hydrogen sulfite, and disulfite.

8. The method of claim 6, wherein contacting or amplifying comprises use of at least one method selected from the group consisting of: use of a heat-resistant DNA polymerase as the amplification enzyme; use of a polymerase lacking 5'-3' exonuclease activity; use of a polymerase chain reaction (PCR); and generation of a amplificate nucleic acid molecule carrying a detectable labels.

9. The method of claim 8, wherein the nucleic acid molecule or peptide nucleic acid molecule is in each case modified at the 5'-end thereof to preclude degradation by an enzyme having 5'-3' exonuclease activity.

10. The method of claim 8, wherein the nucleic acid molecule or peptide nucleic acid molecule is in each case lacking a 3' hydroxyl group.

11. The method of claim 10, wherein the amplification enzyme is a polymerase lacking 5'-3' exonuclease activity.

12. The method of claim 6, wherein determining comprises hybridization of at least one nucleic acid molecule or peptide nucleic acid molecule in each case comprising a contiguous sequence at least 9 nucleotides in length that is complementary to, or hybridizes under stringent conditions to a sequence selected from the group consisting of SEQ ID NOS:7, 8, 9, 10, 15, 16, 17 and 18, and complements thereof.

13. The method of claim 12, further comprising extending at least one such hybridized nucleic acid molecule by at least one nucleotide base.

14. The method of claim 6, wherein determining comprises sequencing of the amplificate.

15. The method of claim 6, wherein contacting or amplifying comprises use of methylation-specific primers.

16. The method of claim 2, wherein distinguishing between methylated and non methylated CpG dinucleotide sequences within the target sequence comprises the use of methylation sensitive restriction enzymes.

* * * * *